(12) United States Patent
Harrington

(10) Patent No.: US 11,554,239 B2
(45) Date of Patent: *Jan. 17, 2023

(54) HEAT AND MOISTURE EXCHANGER FOR A PATIENT INTERFACE

(71) Applicant: ResMed Pty Ltd, Bella Vista (AU)

(72) Inventor: Matthew Rolf Harrington, Gosford (AU)

(73) Assignee: ResMed Pty Ltd, Bella Vista (AU)

( * ) Notice: Subject to any disclaimer, the term of this patent is extended or adjusted under 35 U.S.C. 154(b) by 260 days.

This patent is subject to a terminal disclaimer.

(21) Appl. No.: 17/084,741

(22) Filed: Oct. 30, 2020

(65) Prior Publication Data

US 2021/0046274 A1  Feb. 18, 2021

Related U.S. Application Data

(63) Continuation of application No. 15/930,597, filed on May 13, 2020, which is a continuation of application
(Continued)

(30) Foreign Application Priority Data

Jul. 29, 2013 (AU) .............................. 2013902810
Aug. 7, 2013 (NZ) ....................................... 613874

(51) Int. Cl.
*G06V 10/00* (2022.01)
*A61M 16/10* (2006.01)
(Continued)

(52) U.S. Cl.
CPC .... *A61M 16/1045* (2013.01); *A61M 16/0057* (2013.01); *A61M 16/026* (2017.08);
(Continued)

(58) Field of Classification Search
CPC ............ A61M 16/1045; A61M 16/026; A61M 16/0057; A61M 16/06; A61M 16/16;
(Continued)

(56) References Cited

U.S. PATENT DOCUMENTS 3,326,214 A   6/1967 Mccoy
4,458,679 A   7/1984 Ward
(Continued)

FOREIGN PATENT DOCUMENTS

CN   1893996 A   1/2007
CN   10310787 A   11/2008
(Continued)

OTHER PUBLICATIONS

Extended European Search Report dated Dec. 10, 2020 issued in European Application No. 20162081.2 (9 pages).
(Continued)

*Primary Examiner* — Amir Alavi
(74) *Attorney, Agent, or Firm* — Nixon & Vanderhye P.C.

(57) ABSTRACT

A patient interface for supplying a flow of breathable gas to the airways of a patient may comprise a heat and moisture exchanger (HME). The HME may be positioned in a flow path of the flow of breathable gas. The HME may absorb heat and moisture from gas exhaled by the patient and the incoming flow of breathable gas to be supplied to the patient's airways may be heated and moisturized by the heat and moisture held in the HME.

26 Claims, 60 Drawing Sheets

Related U.S. Application Data

No. 14/908,280, filed as application No. PCT/AU2014/050154 on Jul. 29, 2014, now Pat. No. 10,695,521.

(51) Int. Cl.
   *A61M 16/06* (2006.01)
   *A61M 16/16* (2006.01)
   *A61M 16/00* (2006.01)

(52) U.S. Cl.
   CPC ............ *A61M 16/06* (2013.01); *A61M 16/16* (2013.01); *A61M 16/0683* (2013.01); *A61M 16/107* (2014.02); *A61M 16/109* (2014.02); *A61M 16/1055* (2013.01); *A61M 2016/0027* (2013.01); *A61M 2016/0036* (2013.01); *A61M 2205/21* (2013.01); *A61M 2205/3365* (2013.01); *A61M 2205/3368* (2013.01); *A61M 2205/3653* (2013.01); *A61M 2205/52* (2013.01); *A61M 2205/8206* (2013.01)

(58) Field of Classification Search
   CPC .............. A61M 16/107; A61M 16/109; A61M 16/1055; A61M 2016/0027; A61M 2016/0036; A61M 2205/21; A61M 2205/3365; A61M 2205/3368; A61M 2205/3653; A61M 2205/52; A61M 2205/8206
   See application file for complete search history.

(56) References Cited

U.S. PATENT DOCUMENTS

| | | | |
|---|---|---|---|
| 4,771,770 A | 9/1988 | Artemenko | |
| 4,782,832 A | 11/1988 | Trimble et al. | |
| 4,944,310 A | 7/1990 | Sullivan | |
| 5,022,394 A | 6/1991 | Chmielinski | |
| 5,320,096 A | 6/1994 | Hans | |
| 5,559,173 A | 9/1996 | Campo et al. | |
| 5,570,684 A | 11/1996 | Behr | |
| 5,595,173 A | 1/1997 | Dodd | |
| 5,617,913 A | 4/1997 | Degregoria et al. | |
| 5,701,891 A | 12/1997 | Groenke | |
| 6,478,026 B1 | 11/2002 | Wood | |
| 6,532,959 B1 | 3/2003 | Berthon-Jones | |
| 6,561,190 B1 | 5/2003 | Kwok | |
| 6,581,594 B1 | 6/2003 | Drew et al. | |
| 7,302,950 B2 | 12/2007 | Berthon-Jones et al. | |
| 7,721,732 B2 | 5/2010 | Fu et al. | |
| 7,866,944 B2 | 1/2011 | Kenyon et al. | |
| 7,934,501 B2 | 5/2011 | Bagby | |
| 8,381,723 B2 * | 2/2013 | DiBlasi ............... | A61M 16/021 128/200.24 |
| 8,636,479 B2 | 1/2014 | Kenyon et al. | |
| 8,638,014 B2 | 1/2014 | Sears et al. | |
| 8,677,999 B2 * | 3/2014 | Allum .................. | A61M 16/20 128/204.25 |
| 10,471,230 B2 * | 11/2019 | Harwood .......... | A61M 16/0875 |
| 10,695,521 B2 * | 6/2020 | Harrington ........... | A61M 16/16 |
| 10,751,495 B2 * | 8/2020 | Klee .................. | A61M 16/06 |
| 10,869,977 B2 * | 12/2020 | Chang ............... | A61M 16/0051 |
| 11,203,668 B2 | 8/2021 | Duveen et al. | |
| 11,123,514 B2 * | 9/2021 | Sardesai ............. | A61M 16/024 |
| 11,273,276 B2 * | 3/2022 | Cheng ............... | A61M 16/0683 |
| 11,338,103 B2 * | 5/2022 | Blanch .............. | A61M 16/0683 |
| 11,351,324 B2 * | 6/2022 | Dantanarayana ... | A61M 16/208 |
| 11,357,943 B2 * | 6/2022 | Bentley ............. | A61M 16/0683 |
| 11,406,781 B2 * | 8/2022 | Davidson .......... | A61M 16/0875 |
| 2008/0230068 A1 | 9/2008 | Rudolph | |
| 2008/0283053 A1 | 11/2008 | Zucchi | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2011/0023874 A1 | 2/2011 | Bath et al. | |
| 2011/0108036 A1 | 5/2011 | Thomas | |
| 2011/0214676 A1 | 9/2011 | Allum et al. | |
| 2011/0297152 A1 | 12/2011 | Duveen | |
| 2012/0097156 A1 | 4/2012 | Bowman et al. | |
| 2012/0167879 A1 | 7/2012 | Bowman | |
| 2012/0266873 A1 | 10/2012 | Lalonde | |
| 2012/0325205 A1 | 12/2012 | Allum et al. | |
| 2012/0325218 A1 | 12/2012 | Brambilla et al. | |
| 2013/0184602 A1 | 7/2013 | Brambilla | |
| 2013/0190643 A1 | 7/2013 | Brambilla | |
| 2014/0276177 A1 | 9/2014 | Brambilla et al. | |
| 2016/0022948 A1 | 1/2016 | Martin et al. | |
| 2016/0175552 A1 | 6/2016 | Harrington | |
| 2020/0269005 A1 | 8/2020 | Harrington et al. | |

FOREIGN PATENT DOCUMENTS

| | | |
|---|---|---|
| EP | 0 205 072 B1 | 8/1991 |
| EP | 1 516 643 A1 | 3/2005 |
| JP | 61-280871 | 12/1986 |
| JP | 2002-521103 | 7/2002 |
| JP | 2006-122268 A | 5/2006 |
| JP | 2006-136461 | 6/2006 |
| JP | 2008-507305 | 3/2008 |
| JP | 2012-514512 A | 6/2012 |
| JP | 2013-508087 | 3/2013 |
| WO | WO 98/04310 A1 | 2/1998 |
| WO | WO 98/34665 A1 | 8/1998 |
| WO | WO 00/04958 | 2/2000 |
| WO | WO 00/78381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2011/058371 A1 | 5/2011 |
| WO | 2012/048364 A1 | 4/2012 |
| WO | 2012/177562 A1 | 12/2012 |
| WO | 2012/177566 A1 | 12/2012 |
| WO | WO 2012/171072 A1 | 12/2012 |
| WO | WO 2013/020167 A1 | 2/2013 |
| WO | 2015/052681 A1 | 4/2015 |

OTHER PUBLICATIONS

Office Action dated Dec. 21, 2020 issued in Japanese Application No. 2019-235101 with English translation (19 pages).
First Office Action issued in related Japanese Application No. 2016-530272 dated Jul. 2, 2018, with English translation, (11 pages).
First Examination Report issued in New Zealand Application No. 613874, dated Aug. 9, 2013, 3 pages.
Second Office Action issued in related Chinese Application No. 201480053828.1 with English translation, dated Nov. 8, 2017, 15 pages.
First Examination Report issued in related New Zealand Application No. 734694, dated Sep. 8, 2017, 3 pages.
First Office Action issued in related Chinese Application No. 201480053828.1 with English translation, dated Feb. 28, 2017, 16 pages.
European Search Report issued in related European Application No. 14832657.2, dated Mar. 3, 2017, 10 pages.
First Examination Report issued in related New Zealand Patent Application No. 631077, dated Mar. 11, 2016, 2 pages.
International Search Report for PCT/AU2014/050154 dated Nov. 12, 2014, 6 pages.
Written Opinion of the ISA for PCT/AU2014/050154 dated Nov. 12, 2014, 12 pages.
Written Opinion of the IPEA for PCT/AU2014/050154 dated Jul. 20, 2015, 12 pages.
International Preliminary Report on Patentability for PCT/AU2014/050154 dated Nov. 3, 2015, 100 pages.
West, John B., "Respiratory Physiology", Lippincott Williams & Wilkins, 9th edition published 2012, 8 pages.

(56) References Cited

OTHER PUBLICATIONS

Brochure for "Dräger Medical E-vent N" with English translation, Nov. 10, 2003, 4 pages.

Jacob Maag, Carsten Lassen, Ulla Kristine Brandt, Jesper Kjolholt, Lise Molander og Sonja Hagen Mikkelsen; Identification and assessment of alternatives to selected phthalates; COWI A/S, Denmark; 2010.

Office Action dated Mar. 22, 2022 issued in Japanese Application No. 2021-83847 with translation (11 pages).

* cited by examiner

| | Flute height (mm) | take-up factor | Number of flutes per meter |
|---|---|---|---|
| A-FLUTE | 4.5-4.7 | 1.55±5% | 105-125 |
| B-FLUTE | 2.1-2.9 | 1.33±5% | 150-185 |
| C-FLUTE | 3.5-3.7 | 1.44±5% | 120-145 |
| E-FLUTE | 1.1-1.4 | 1.27±5% | 290-340 |
| F-FLUTE | 0.7-1.0 | 1.23±5% | 370-435 |
| G-FLUTE | 0.5-0.55 | 1.18±5% | 526-555 |
| N-FLUTE | 0.4-0.45 | 1.12±5% | 588-625 |
| O-FLUTE | 0.3-0.35 | 1.01±5% | 333-250 |

FIG. 13C

|  |  | Unit | Tested HME (Flute F) | Optimal HME (Flute F) | Min HMX (Flute C) | Min HMX (Flute E) | Max HMX (Flute N) | Max HMX (Flute O) |
|---|---|---|---|---|---|---|---|---|
| HME Paper | Grade | gsm | 65 | 65 | 65 | 65 | 65 | 65 |
|  | Paper thickness | mm | 0.08 | 0.08 | 0.08 | 0.08 | 0.08 | 0.08 |
|  | Flute pitch | mm | 2.5 | 2.5 | 7.5 | 3.2 | 1.6 | 3.4 |
|  | Flute height | mm | 0.85 | 0.85 | 3.6 | 1.25 | 0.43 | 0.33 |
| HME Stack | Height | mm | 20 | 15 | 15 | 15 | 15 | 15 |
|  | Width | mm | 38 | 38 | 38 | 38 | 38 | 38 |
|  | Depth | mm | 11 | 8 | 8 | 8 | 8 | 8 |
|  | Stack Preload | % | 6% | 32% | 0% | 0% | 50% | 50% |
| Summary | Layers in stack |  | 25 | 26 | 4 | 12 | 70 | 92 |
|  | Total Corrugations |  | 380 | 395 | 20 | 143 | 1613 | 1019 |
|  | Corrugation Perimeter | mm | 5.4 | 5.4 | 17.9 | 7.1 | 3.4 | 6.9 |
|  | Total Surface Area | mm2 | 45447 | 34357 | 5718 | 16287 | 88681 | 112430 |
|  | Total Volume | mm3 | 8360 | 4560 | 4560 | 4560 | 4560 | 4560 |
|  | Surface Area per unit volume | m2/m3 | 5.4 | 7.5 | 1.3 | 3.6 | 19.4 | 24.7 |
|  | Impedance (@100L/min) | cmH2O | 0.47 | 1.6 |  |  |  |  |

FIG. 13D

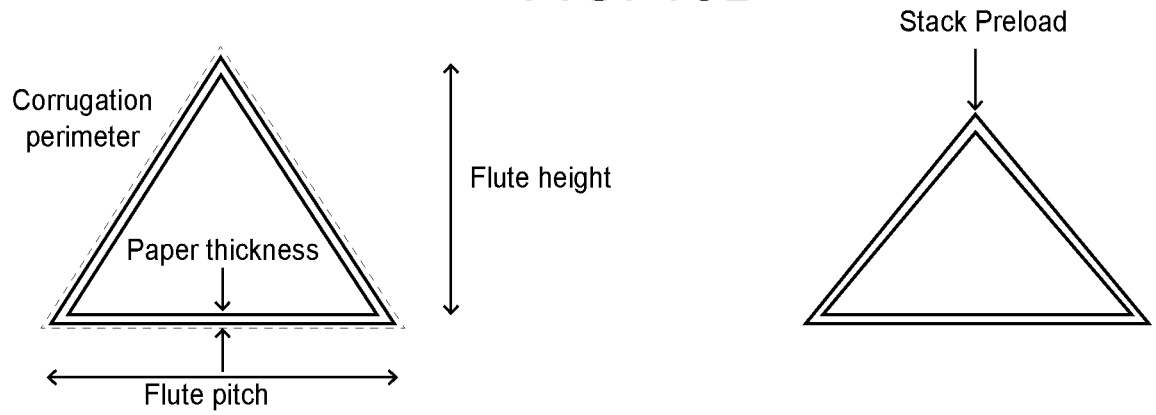

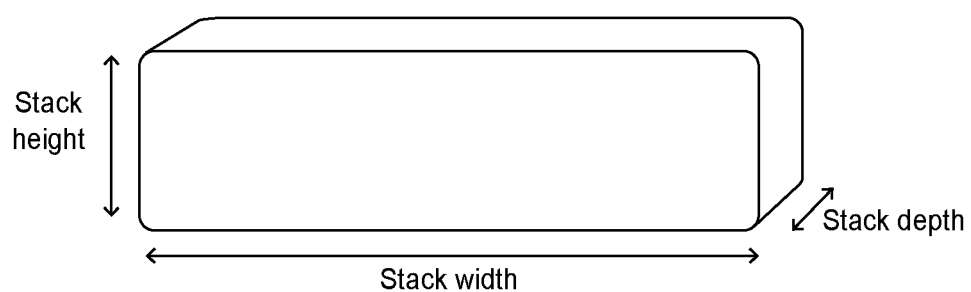

FIG. 13E

HEAT AND MOISTURE EXCHANGER FOR A PATIENT INTERFACE

1 CROSS-REFERENCE TO RELATED APPLICATIONS his application is a continuation of U.S. Application Ser. No. 15/930,597, filed May 13, 2020, now pending, which is a continuation of U.S. application Ser. No. 14/908,280, filed Jan. 28, 2016, now U.S. Pat. No. 10,695,521, which is the U.S. national phase of International Application No. PCT/AU2014/050154 filed Jul. 29, 2014 which designated the U.S. and claims priority to Australian Patent Application No. AU 2013902810, filed Jul. 29, 2013, and New Zealand Patent Application No. NZ 613874, filed Aug. 7, 2013, the entire contents of each of which are hereby incorporated by reference.

2 BACKGROUND OF THE TECHNOLOGY

2.1 Field of the Technology

The present technology relates to one or more of the detection, diagnosis, treatment, prevention and amelioration of respiratory-related disorders. In particular, the present technology relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by nasal CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours. This discomfort may lead to a reduction in patient compliance with therapy. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of nasal CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may unintentionally leak. Furthermore, if the shape of the seal-forming portion does not match that of the patient, it may crease or buckle in use, giving rise to unintentional leaks.

Another type of seal-forming portion may comprise a friction-fit element, e.g. for insertion into a naris, however some patients find these uncomfortable.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534. However these may be uncomfortable for some.

Another technique is the use of one or more straps and stabilising harnesses. Many such harnesses suffer from being one or more of ill-fitting, bulky, uncomfortable and awkward to use.

2.2.3.1.3 Vent Technologies

Some forms of patient interface systems may include a vent to allow the washout of exhaled carbon dioxide. The vent may allow a flow of gas from an interior space of the patient interface, e.g. the plenum chamber, to an exterior of the patient interface, e.g. to ambient. The vent may comprise an orifice and gas may flow through the orifice in use of the mask. Many such vents are noisy. Others may block in use and provide insufficient washout. Some vents may be disruptive of the sleep of a bed-partner 1100 of the patient 1000, e.g. through noise or focused airflow.

ResMed Limited has developed a number of improved mask vent technologies. See WO 19981034,665; WO 2000/078,381; U.S. Pat. No. 6,581,594; US Patent Application; US 2009/0050156; US Patent Application 2009/0044808.

Table of noise of prior masks (ISO 17510-2:2007, 10 cm $H_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10 cm $H_2O$)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 cm$H_2O$).

| RPT Device name | A-weighted sound power level dB(A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |

-continued

| RPT Device name | A-weighted sound power level dB(A) | Year (approx.) |
| --- | --- | --- |
| S9 AutoSet | 26.5 | 2010 |
| S9 AutoSet with H5i Humidifier | 28.6 | 2010 |

One known RPT device used for treating sleep disordered breathing is the S9 Sleep Therapy System, manufactured by ResMed. Another example of an RP device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisde™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

2.2.3.3 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). As a result, a medical humidifier may be small for bedside placement, and it may be configured to only humidify and/or heat the flow of air delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patient.

2.2.4 Heat and Moisture Exchanger (HME)

Heat and moisture exchangers are generally made up of foam, paper, or a substance capable of acting as a condensation and absorption surface. The material may carry hygroscopic salts to improve the water-retaining capacity. Suitable salts include calcium chloride.

HMEs may be utilized in RPT therapy, such as in PAP therapy, to partially recover heat and moisture present in exhaled gas from a patient's airways. This heat and moisture can be retained and recycled to the patient in a passive manner as a flow of breathable gas passes through the HME prior to inspiration. Thus, the use of HME's can provide the needed moisture and humidity (generally recognized as >10 mg/l) to most patients during PAP therapy to minimize any detrimental effects associated with PAP therapy with non-humidified ambient air whilst avoiding the need for a heated humidifier system. The use of a HME rather than a heated humidifier may also lower the possibility of occlusion caused by condensation in air delivery tubes.

The use of a HME in PAP therapy can avoid the need for additional power required with heated humidifiers and may reduce the need for extra associated components. This may reduce the manufacturing costs and also reduce the overall size of the CPAP therapy unit.

A problem common with the use of HMEs in CPAP therapy relates to the ability of the HME to provide sufficient heat and moisture while also minimizing flow impedance and maintaining comfortable and safe levels of CO2 washout. Flow impedance may affect patient breathing effort (work of breathing) and also impacts event (apnoea, hypopnoea, snore) detection algorithms so in many cases it is sought to be minimized. Furthermore, consideration should also be given to heat and moisture loss from venting to ensure that the HME is functioning to counteract this loss.

Current configurations of HME's in RPT therapy have shown negligible patient humidification, have issues with flow impedance, and/or $CO_2$ washout. For example, placing the HME unit within the elbow, around the exhaust vent or on the flow generator side of the therapy system has shown issues with impedance, and/or $CO_2$ washout with negligible patient humidification (hygroscopic) benefit. In this configuration the vent flow is the dominant flow through the HME. The vent flow being the flow from the patient or the flow generator that flows through the HME and directly out through the vent. Moreover, current designs of HME's do not allow for sufficient moisture exchange during patient exhalation to provide sufficient humidification levels to the patient. Thus, there is a need to provide superior configurations and designs for HME use in RPT therapy, such as PAP therapy, to achieve desired patient humidification whilst having acceptable impedance on the flow of therapy and $CO_2$ washout.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology comprises a patient interface for delivering a flow of breathable gas to an entrance of a patient's airways including at least an entrance of a patient's nares, said patient interface comprising a HME comprising at least one corrugated structure. The corrugated structure may comprise a plurality of corrugations or flutes through the HME along a surface of the corrugated structure, wherein the corrugated structure retains moisture from a flow of expiratory gas, and wherein the retained moisture is provided to the flow of breathable gas for humidification.

Moisture may include both liquid and vapour forms. The term 'corrugation' as referred to here is also commonly referred to as a flute and is used interchangeably. The plurality of corrugations increase the surface area of the corrugated structure within a fixed volume, which allows for an increased interaction between the surface of the HME and the air exhaled from the patient. This allows for increased heat and moisture exchange between the patient and the HME and ultimately may improve the humidification performance of the HME within the patient interface to the desired level. Furthermore, the increased humidification performance allows a smaller HME to function to a desired performance level, thereby occupying a smaller volume in the patient interface. The volume occupied by the HME can influence flow impedance, effecting $CO_2$ washout and/or resulting in therapeutic pressure loss delivered to the patient during PAP therapy. Thus, having an increased surface area per unit volume of the corrugated HME material for moisture exchange allows for a reduction on the impact of the HME on flow impedance. Moreover, the corrugations allow for greater access of the flow of breathable gas to the heat and moisture exchange surfaces of the HME thereby providing a HME with a high surface area per unit volume that is capable of providing superior humidification to the patient.

Another aspect of one form of the present technology is the HME, wherein the HME is orientated such that a plurality of channels defined, partially or completely, by the corrugations of the HME are substantially parallel to the flow path of the flow of breathable gas. The orientation of the channels allows for the flow of breathable gas to flow directly through the HME along the surface of the moisture exchange layer, thereby reducing the impact of the HME on flow impedance.

Another aspect of one form the present technology is a HME that may further comprise a substantially planar base structure, and wherein the corrugated structure may be engaged to the base structure to form a layer. The corrugated structure may comprise an upper and a lower folded portion and each lower folded portion may be engaged to the base structure. The base structure may form a supporting planar base in which the corrugated structure may extend vertically therefrom to form the layer. Alternatively, the layer may further comprise a substantially planar top structure such that the corrugated structure is disposed between the top and base structures to form a concertina layer. The HME may be comprised of the single concertina layer. The top and base structures may provide structural support to the corrugated structure and maintain the channels formed by the corrugations to allow the flow of breathable gas through the HME along a surface of the corrugated structure. The top and/or base structure may be formed of a moisture non-absorbent material. Alternatively, the top and/or base structure may be formed of the same material as the corrugated structure. The weight of the top and/or base structure may be between 15-100 g/m². The thickness of the top and/or base structure impacts the rigidity of the structures and hence their ability to provide structural support. However, there is a trade-off that exists between maximising the thickness of the top and/or base structure to provide support and minimising the thickness to reduce the impact of the HME of flow impedance. The overall thickness of the HME is a crucial factor that alters the density and surface area per unit volume of the HME. These factors in turn impact on the overall humidification performance of said HME.

In another form of the present technology, the HME may be formed of a plurality of layers forming a predetermined three-dimensional shape adapted to fit within a plenum chamber of the patient interface. Each layer comprises a corrugated structure and at least a supporting substantially planar base structure. Patient interfaces come in varying shapes and sizes. Thus, the HME must conform to the varying inner volume of the patient interface in order to fit within its inner walls. Shaping a HME into a desired three-dimensional shape to fit within a patient interface in the appropriate orientation is difficult. Moreover, having the HME fit in the correct orientation while maintaining its efficacy in humidification and reducing the impact of the HME on flow impedance adds a further level of complexity. Generally, materials used in the manufacture of HME's cannot be moulded to produce the desired three-dimensional shapes while maintaining the ability to humidify the flow of gas. Thus, forming a HME from a plurality of layers in a desired three-dimensional shape may provide flexibility in shaping the HME while maintaining its humidification performance. The HME of the present technology may be formed by stacking the plurality of layers. The layers may be vertically stacked along a vertical axis of the HME. Stacking layers of HME material allows the HME to be formed into the desired three-dimensional shape while positioning each layer in the appropriate orientation to maximise performance. The plurality of channels formed by the corrugated structures within each layer may be substantially vertically aligned to the plurality of channels of a corrugated structure in an adjacent layer to maximise the flow of breathable gas through the channels for moisture exchange. Each layer may be formed by laser cutting portions thereof to shape the layer into a predetermined three-dimensional shape. Alternatively, the whole HME may be shaped by laser cutting it to a predetermined three-dimensional shape. The layers may also be formed from different sizes and/or shapes and combined to form a HME of overall desired three-dimensional shape. Having layers of different sizes and shapes allows the formation of the HME into irregular shapes to fit within the plenum chamber of a patient interface.

In another form of the present technology, the HME may also be shaped to avoid contact with a patient's face. The HME may comprise an inwardly curved portion to avoid contact with the patient's nose or mouth. Positioning, the HME in close proximity to the entrance of a patient's airways ensures that the capture of expired moisture is maximised. However, contact to a patient's face should be avoided or at least minimised to prevent discomfort. Thus, it is desirable to shape the HME to follow the facial profile of a patient to position the HME in close proximity to the entrance of a patient's airways while avoiding or at least minimising contact with the patient. For example, the HME may be curved to follow and avoid the profile of the patient's face within the patient interface.

In another form of the present technology, the HME is structured to have a predetermined surface area per unit volume of between 4-14 $m^2/m^3$. The surface area per unit volume is directly correlated to the humidification performance of the HME. That is, having a high surface area per unit volume allows for an increased moisture exchange between the HME and the source of humidity to capture moisture. Furthermore, an HME with a high surface area per unit volume allows for the minimisation of volume the HME occupies within the plenum chamber. The volume occupied by the HME within the plenum chamber can influence flow impedance, effecting CO2 washout and therapeutic pressure delivery to the patient. Thus, having a HME with a high surface area per unit volume allows for a reduced impact of the HME on flow impedance. One way to reduce the surface area per unit volume is to introduce corrugations within the HME. Furthermore, the HME may be formed in a plurality of layers, wherein each of the layers comprises a corrugated structure. The corrugated structures form a plurality of channels and allow the flow of breathable gas through the channels along a surface of the HME. In effect, the corrugations and channels increase a surface area per unit volume of the HME.

In another form of the present technology, the HME is selected to have a water absorbency rate of between 50-100 mm/10 min. A faster water absorbency rate allows for faster moisture exchange by the HME. This allows for an overall improved moisture uptake by the HME and subsequently faster moisture redelivery from the HME to the patient. The water absorbency rate may be modified by altering the amount of HME material available within a fixed volume. Moreover, the water absorbency rate is also impacted by the surface area of the HME that is available for moisture exchange. Thus, the HME may be selected to maximise the amount of HME material within a predetermined volume, while trying to maximise the surface area per unit volume of the HME available for moisture exchange. Moreover, the water absorbency rate may also be increased by the addition of biocompatible additives such as drying additives. For example, $CaCl_2$) may be added to the HME.

Another aspect of one form of the present technology is directed towards a HME structured to have a flow impedance of between 0-2.5 cm of $H_2O$ at a predetermined flow rate of 100 L/min. The flow impedance may be between 0-1.6 cm of $H_2O$ at the predetermined flow rate. The flow rate is the flow of breathable gas delivered to the patient interface. The HME comprising at least one corrugated structure comprising a plurality of corrugations, the plurality of corrugations forming a plurality of channels to allow the flow of breathable gas through the HME along a surface of the corrugated structure. The plurality of channels may reduce the flow impedance of the HME on the flow of breathable gas to the predetermined flow impedance level. The plurality of channels may also reduce the sheet density of the corrugated structure to a predetermined sheet density to reduce the flow impedance to within the predetermined range. The HME may be structured to have at least one corrugated structure having a predetermined density of between 0.02-0.4 g/cm³. Moreover, the obstruction may be reduced by increasing the number of channels to a predetermined number. The flow impedance may also be reduced to within the predetermined range by increasing the pitch of each corrugation or flute to between 1 to 4 mm. Pitch may be understood to mean the width of a channel defined by the corrugations. The pitch of each corrugation or flute is between 1.7-3.5 mm. The flow impedance may also be decreased to within the desired range by increasing a total volume of the plurality of channels in a flow path of the flow of breathable gas. It may also be advantageous to reduce the flow impedance of the HME to the flow of expiratory gas to allow a level of $CO_2$ washout from the patient interface sufficient to prevent significant inspiration of $CO_2$ that may cause breathing discomfort. It is however, also desirable to maintain the humidification performance of the HME on the flow of breathable gas to increase breathing comfort. To increase humidification performance to a predetermined level may require a minimum amount of HME material be present within the HME. Thus, a balance is desirable between the reduction on the level of flow impedance on the flow of expiratory gas caused by the HME and its maintenance of humidification performance.

Another aspect of one form of the present technology is directed towards a HME for removable engagement to a patient interface for delivery of a flow of breathable gas to an entrance of a patient's airways including at least an entrance of a patient's nares, wherein the HME may comprise a rigid frame circumferentially surrounding a peripheral surface of the HME, wherein the frame may be configured to removably engage to an inner surface of a plenum chamber of the patient interface to position the HME in a flow path of the flow of breathable gas. The rigid HME frame may provide structural support to the HME and provide a removably engageable portion to engage within the patient interface. The rigid frame comprises at least one engaging member for engaging to an inner surface of a plenum chamber of the patient interface. The engaging member may comprise a clip for engaging to an inner surface of the plenum chamber. Alternatively, the engaging member may be in the form selected from a group consisting of an adhesively engageable portion, a clip, a resilient flange, a hook and a loop.

Another aspect of one form of the present technology is directed towards the HME frame further comprising a moisture retaining reservoir to retain and resupply additional moisture to the HME material of the HME. For example, the reservoir may resupply the retained moisture to a layer of the HME. In addition to the retention of moisture by the HME, an additional reservoir for retaining moisture may be provided to the frame. For example, a portion of the HME frame may be formed by a moisture absorbent material. This material may be a high density sponge. Moisture can be wicked by the high density sponge frame from the HME and resupplied to the HME to provide supplemental moisture.

Another aspect of one form of the present technology is directed towards a patient interface for delivery of a flow of breathable gas to an entrance of a patient's airways including at least an entrance of a patient's nares, said patient interface comprising a HME configured to separate a plenum chamber of the patient interface into a first anterior chamber and a second posterior chamber. The HME may be positioned in the plenum chamber to humidify the flow of breathable gas flowing from the first anterior chamber to the second posterior chamber. The second posterior chamber may comprise a seal-forming structure for sealing on a portion of the patient's face. The first anterior chamber may comprise an inlet for receiving the flow of breathable gas into the first anterior chamber and a vent for washout of the flow of expiratory gas from the first anterior chamber. This position of the HME in this configuration may be advantageous as it ensures that expiratory gases from a patient flow through the HME for moisture retention prior to washing out through the vent. In addition, the HME may be positioned to ensure that the flow of breathable gas flowing from the inlet flows through the HME to redeliver the retained moisture to the patient. Alternatively, it is also possible to position an additional vent in the posterior plenum chamber to offset $CO_2$ build up within this volume. For example, in the case of a full face mask, the additional volume in the posterior plenum chamber (i.e., dead space volume) in comparison to smaller masks may lead to unwanted excessive $CO_2$ build up occurring within this space. To mitigate this effect, it is possible to position an additional vent proximal to the patient's airways, on the posterior or patient side of the plenum chamber relative to the HME. Positioning a vent on the posterior side of the HME may aid in venting of the HME humidified flow of breathable gases prior to delivery to the patient. To compensate for this venting of humidified air, the overall humidification performance may be maintained by increasing the ability of the HME to humidify the flow of breathable gas within a predetermined volume of the plenum chamber. The inlet may be adapted to removably engage to a conduit for the delivery of the flow of breathable gas into the inlet. The vent may be configured for regulating the washout of expiratory gas at a substantially constant flow rate. The patient interface may further comprise a vent adaptor comprising the vent and the inlet. The vent adaptor may also be adapted to detachably engage to the remainder of the patient interface to form the plenum chamber. The vent adaptor may removably engage to the remainder of the patient interface by resilient clips. The anterior portion of the vent adaptor may also form at least one wall of the first anterior chamber. The vent adaptor may comprise walls forming a housing portion for housing the HME. The housing portion may be configured to locate the HME into the plenum chamber. The vent adaptor may ensure that the vent and inlet are positioned on an anterior side of the HME while the entrance of the patient's airways may be positioned on a posterior side of the HME in use. The patient interface also may comprise a cushion assembly comprising the aperture and the seal forming structure.

Another aspect of one form of the present technology is a method of manufacturing a HME for humidifying a flow of breathable gas delivered by a patient interface, the HME having a desired flow impedance. The method comprising corrugating at least one portion of the HME to form a plurality of channels to allow the flow of breathable gases through the HME and along a surface of the corrugated structure and adjusting the number of corrugations forming channels to increase a flow rate of the flow of breathable gas through the channels to achieve the desired flow impedance.

Another aspect of one form of the present technology is a method of manufacturing a patient interface for delivering a flow of breathable gas to an entrance of a patient's airways, the patient interface comprising a HME with a desired humidification performance for humidifying a flow of breathable gas. The method may further comprise manufacturing a patient interface, determining the volume of a plenum chamber of the patient interface for delivering a flow of breathable gas to a patient, corrugating at least one portion of the HME to form a plurality of channels to allow the flow of breathable gases through the HME and along a surface of the corrugated structure, adjusting the number of corrugations forming channels to increase a surface area per unit of the HME based on the volume of the plenum chamber to achieve the desired added absolute humidity, and/or removably or permanently fixing the HME to within the plenum chamber of the patient interface in a flow path of the flow of breathable gas.

Another aspect of one form of the present technology is a method of manufacturing a HME with an increased surface area per unit volume to achieve a desired humidification performance for humidifying a flow of breathable gas, the method may comprise determining the desired humidification performance, corrugating at least one portion of the HME to form a plurality of channels to allow the flow of breathable gases through the HME and along a surface of the corrugated structure, adjusting the number of corrugations forming channels to increase a surface area per unit volume of the HME, and/or stacking the HME into corrugated layers to further increase a surface area per unit volume of the HME to achieve the desired humidification performance.

Another aspect of one form of the present technology is a method of manufacturing for increasing the humidification performance of a HME to humidify a flow of breathable gas delivered by a patient interface to a desired level, the method may comprise determining the required humidification performance of the HME, laser cutting a plurality of channels through the HME to increase a surface area per unit volume to increase the humidification performance of the HME, and/or increasing the number of channels by laser cutting until the desired humidification performance is achieved.

Another aspect of one form of the present technology is a patient interface that is moulded or otherwise constructed with a clearly defined perimeter shape which is intended to match that of an intended wearer.

An aspect of one form of the present technology is a portable RPT device that may be carried by a person, e.g. around the home of the person.

An aspect of one form of the present technology is a patient interface that may be washed in a home of a patient, e.g. in soapy water, without requiring specialised cleaning equipment. An aspect of one form of the present technology is a humidifier tank that may be washed in a home of a patient, e.g. in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receives a supply of air at positive pressure from a RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 1A:
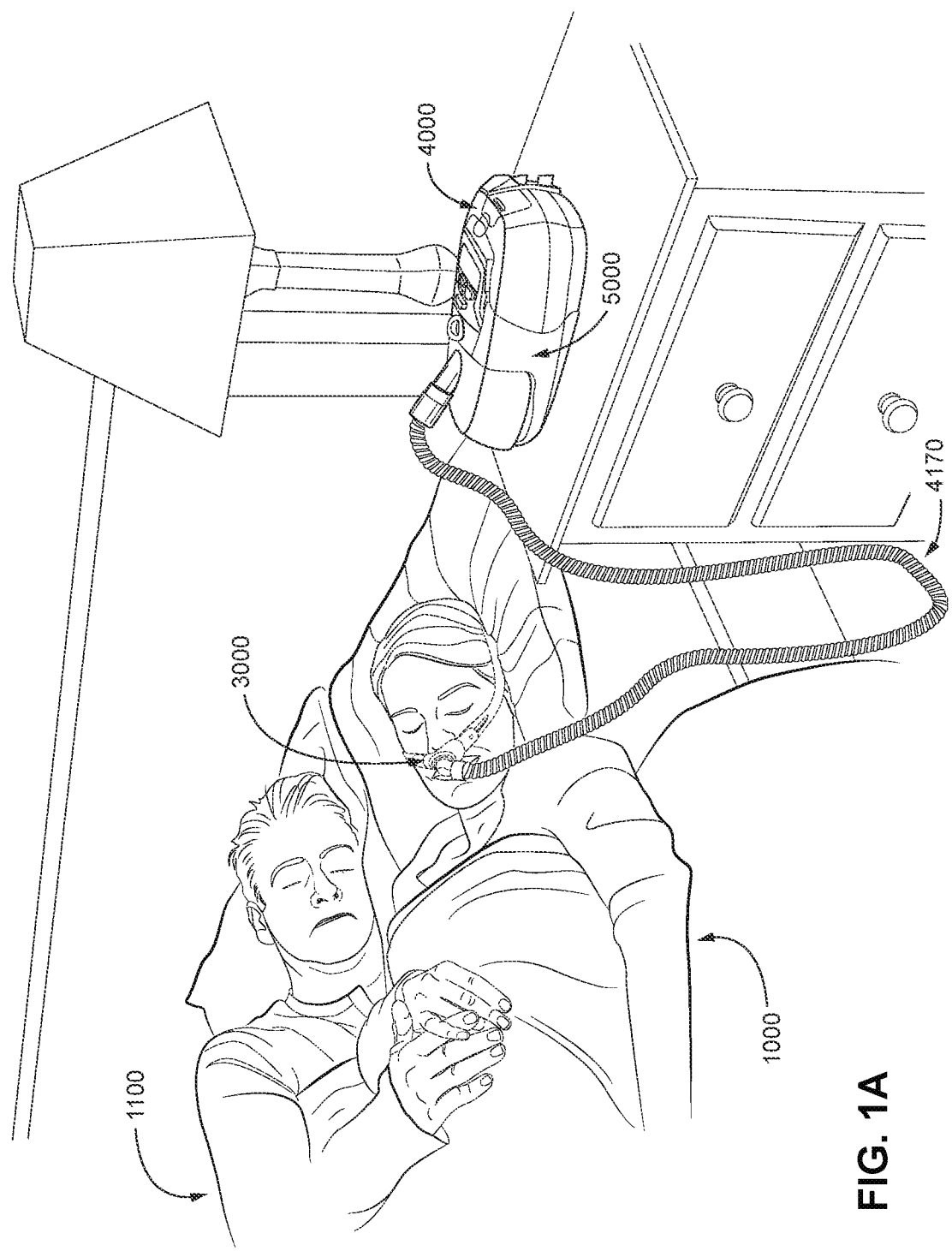
FIG. 1B shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receives a supply of air at positive pressure from a RPT device 4000. Air from the RPT device is humidified in a humidifier 5000, and passes along an air circuit 4170 to the patient 1000.
FIG. 1D shows a patient 1000 undergoing polysomnography (PSG).
Figure 1B:
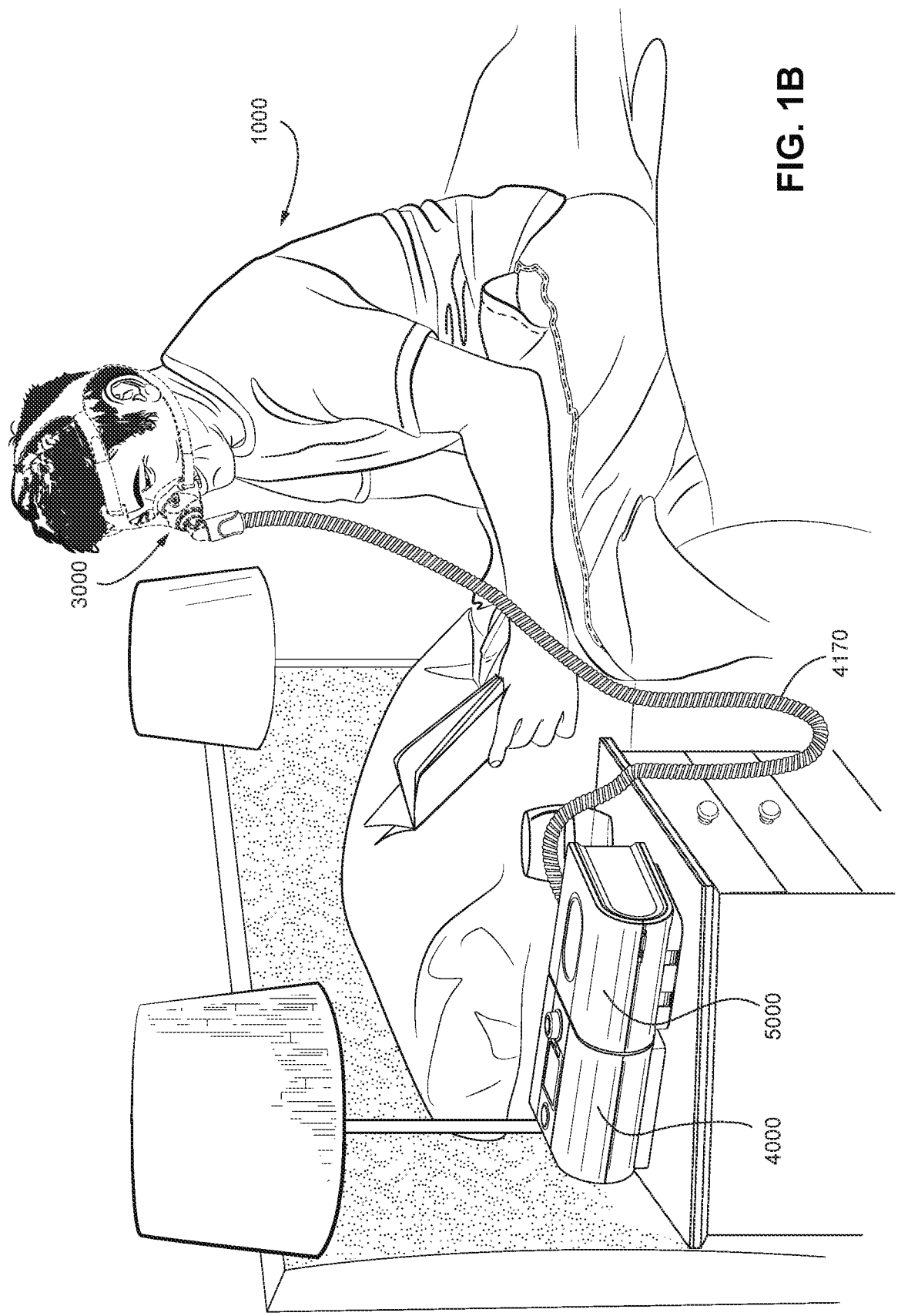
Figure 1C:
Figure 1D:
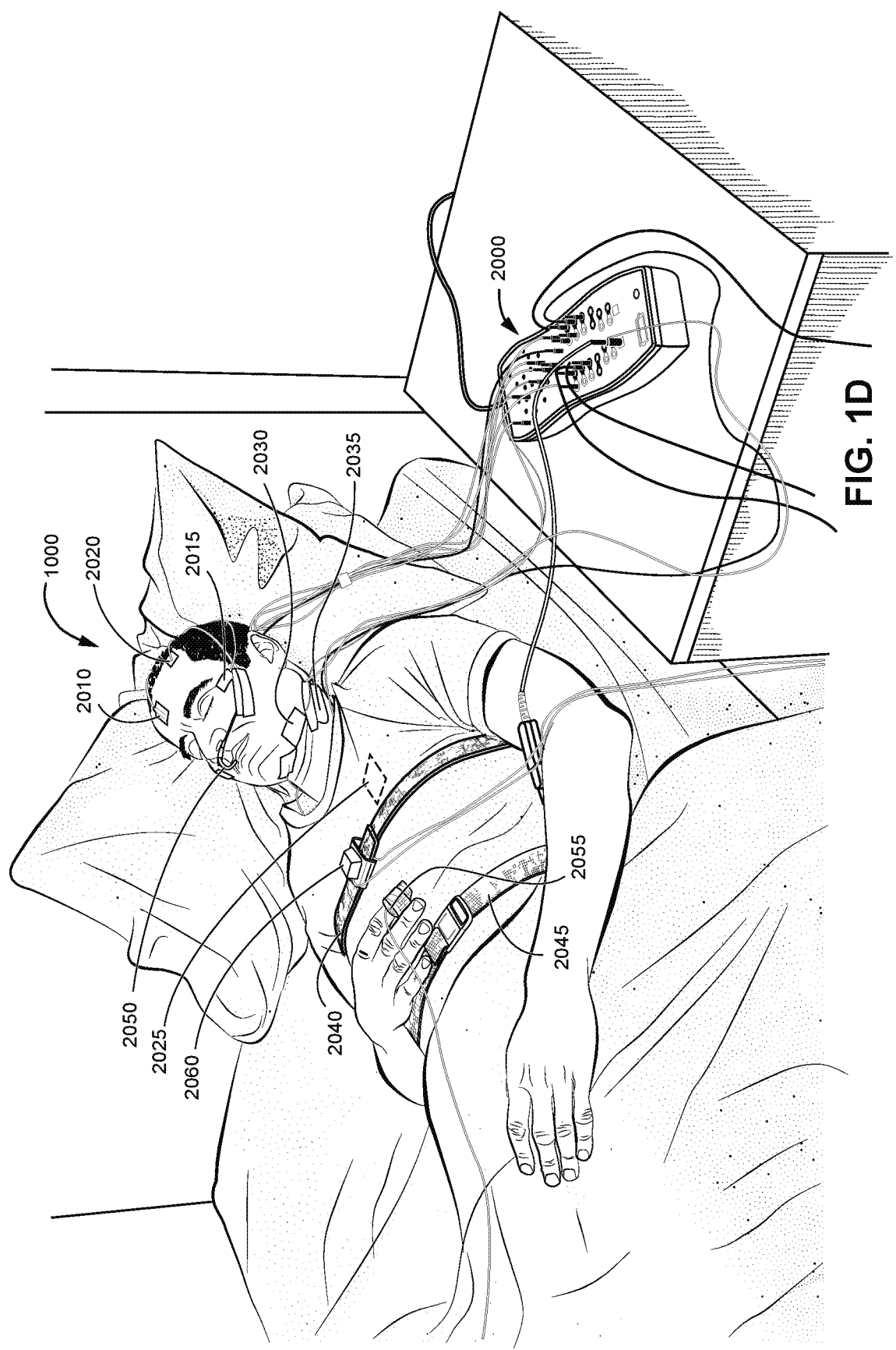
Figure 2A:
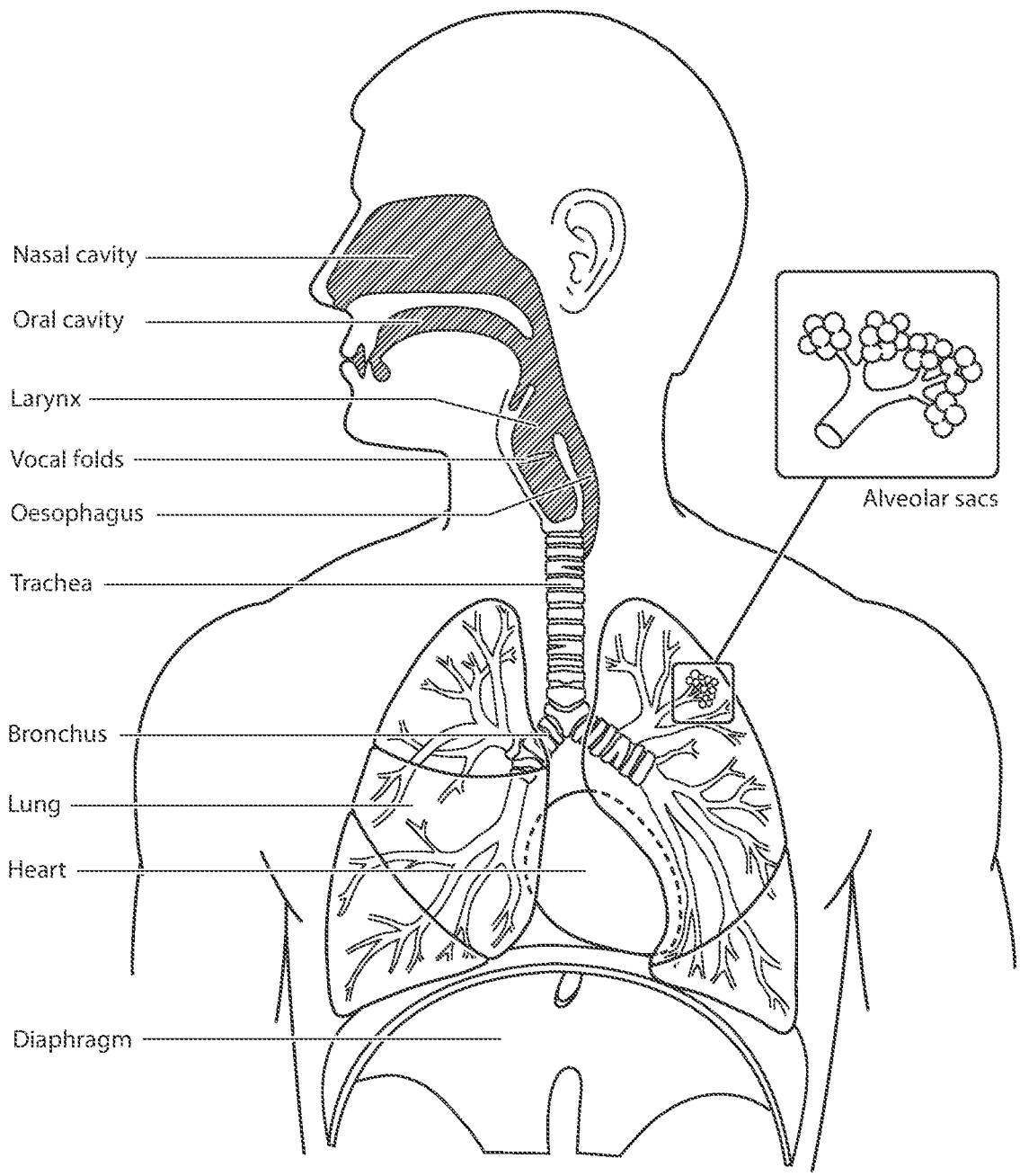

FIG. 2A shows an overview of a human respiratory system including the nasal and oral cavities, the larynx, vocal folds, oesophagus, trachea, bronchus, lung, alveolar sacs, heart and diaphragm.

Figure 2B:
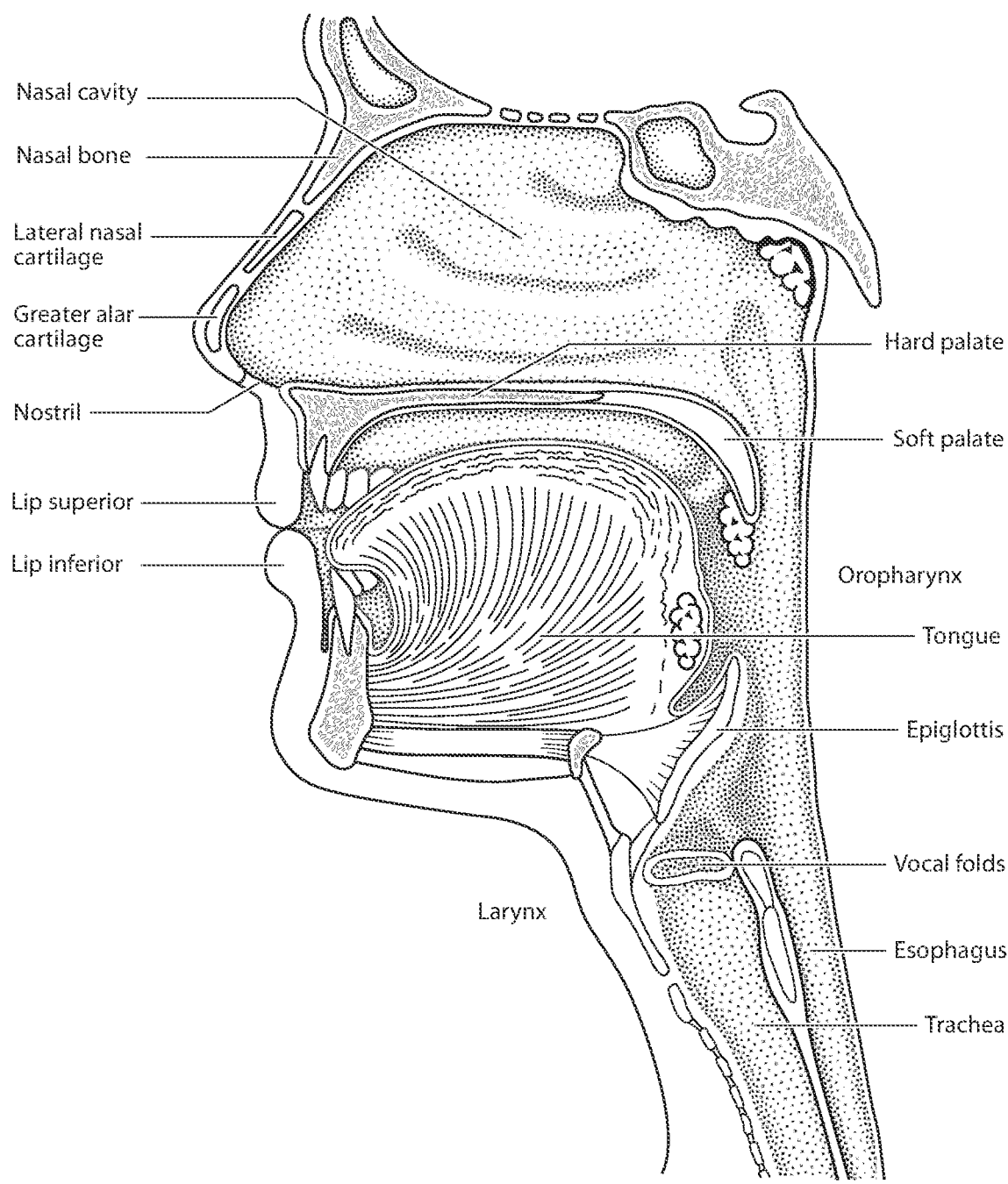

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
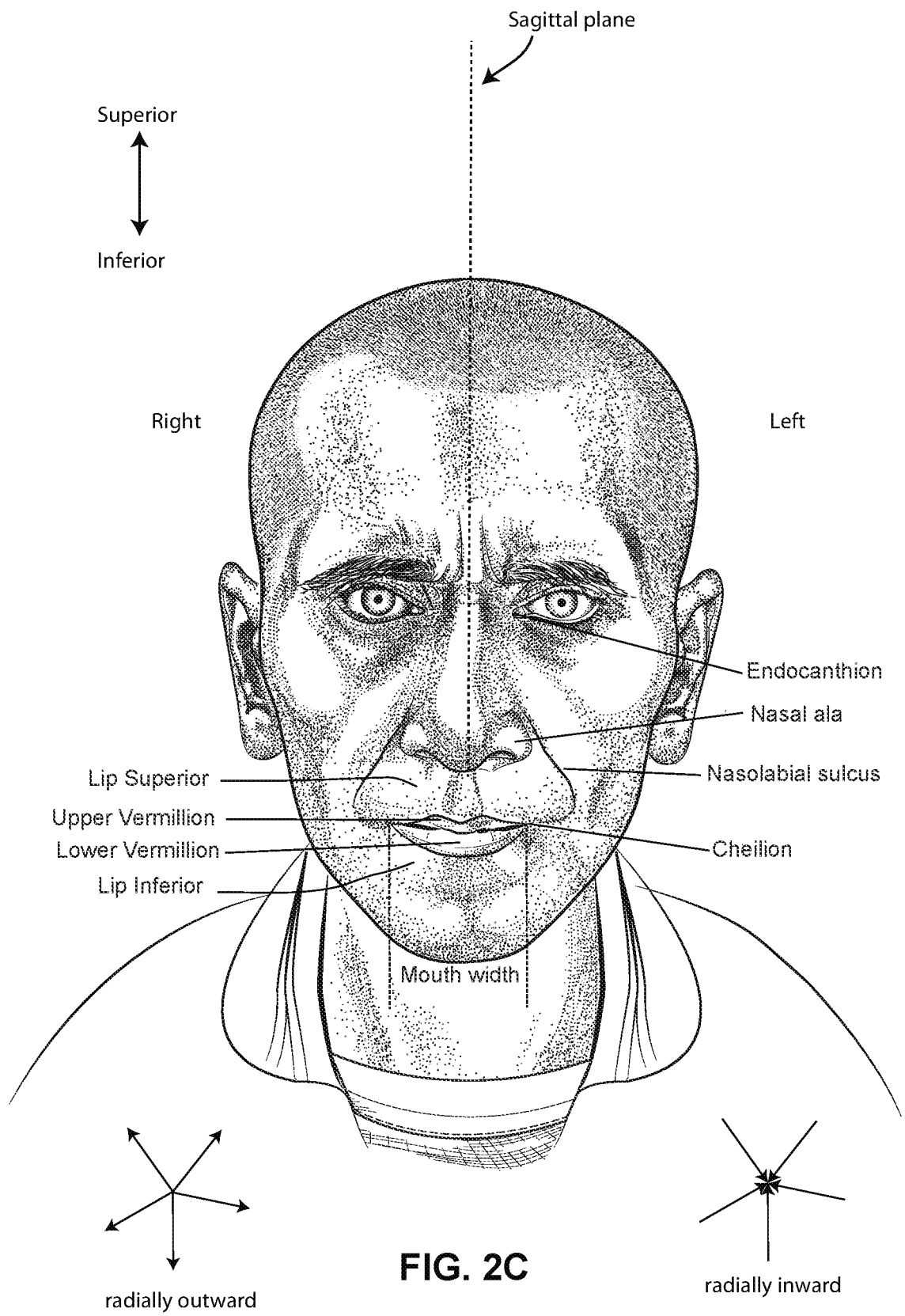

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
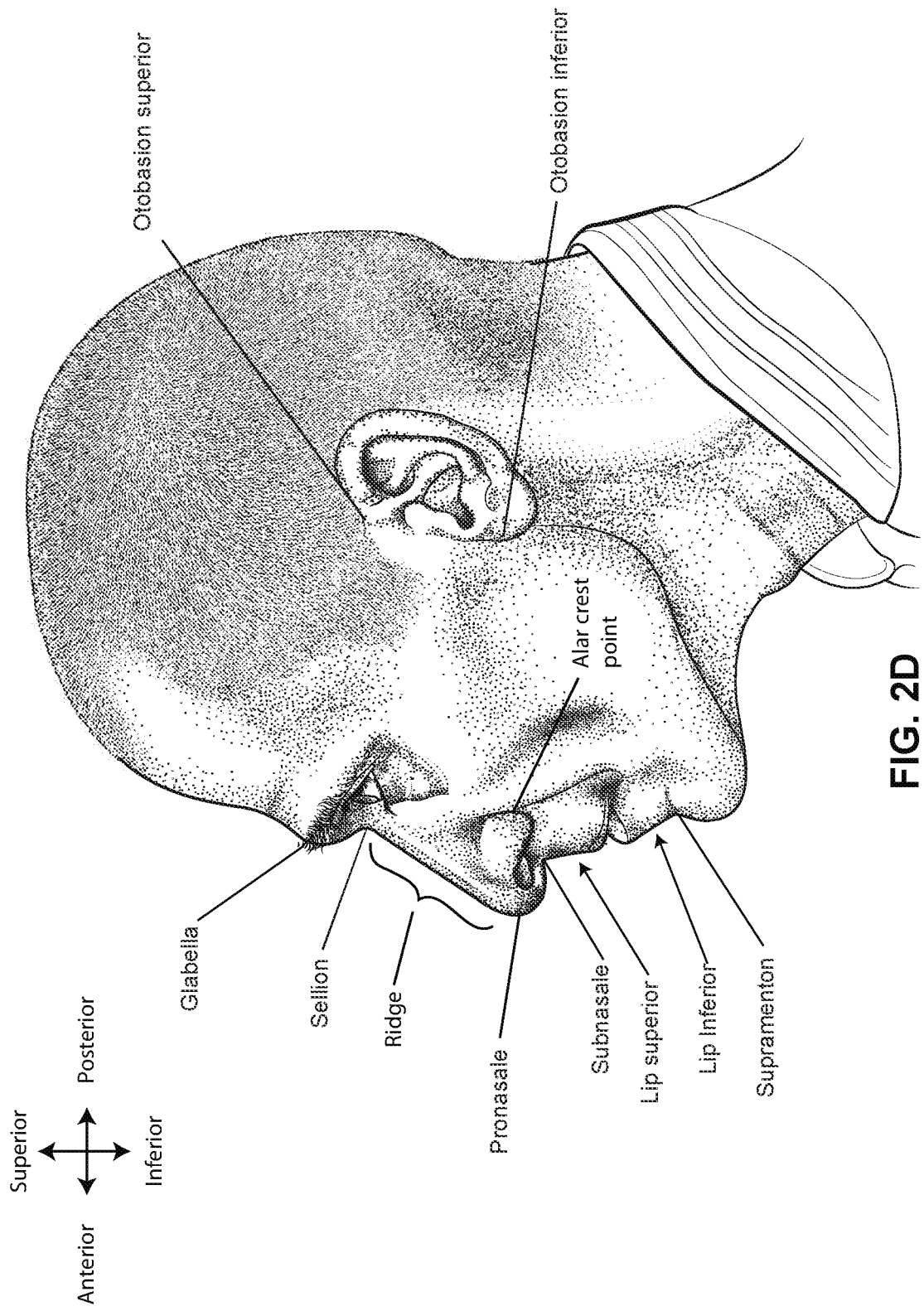

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
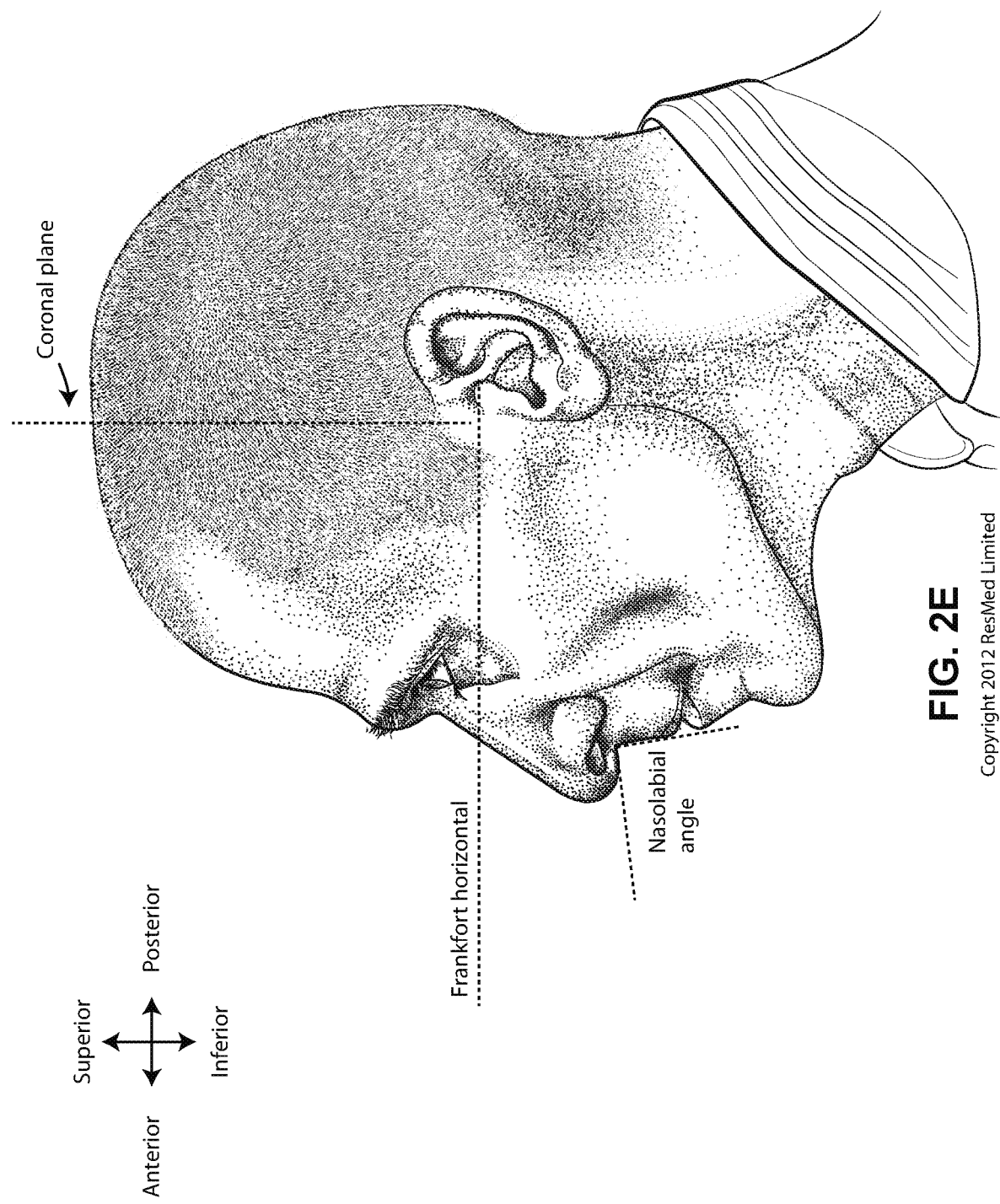

FIG. 2E is a further side view of a head. The approximate locations of the Frankfort horizontal and nasolabial angle are indicated. The coronal plane is also indicated.

Figure 2F:
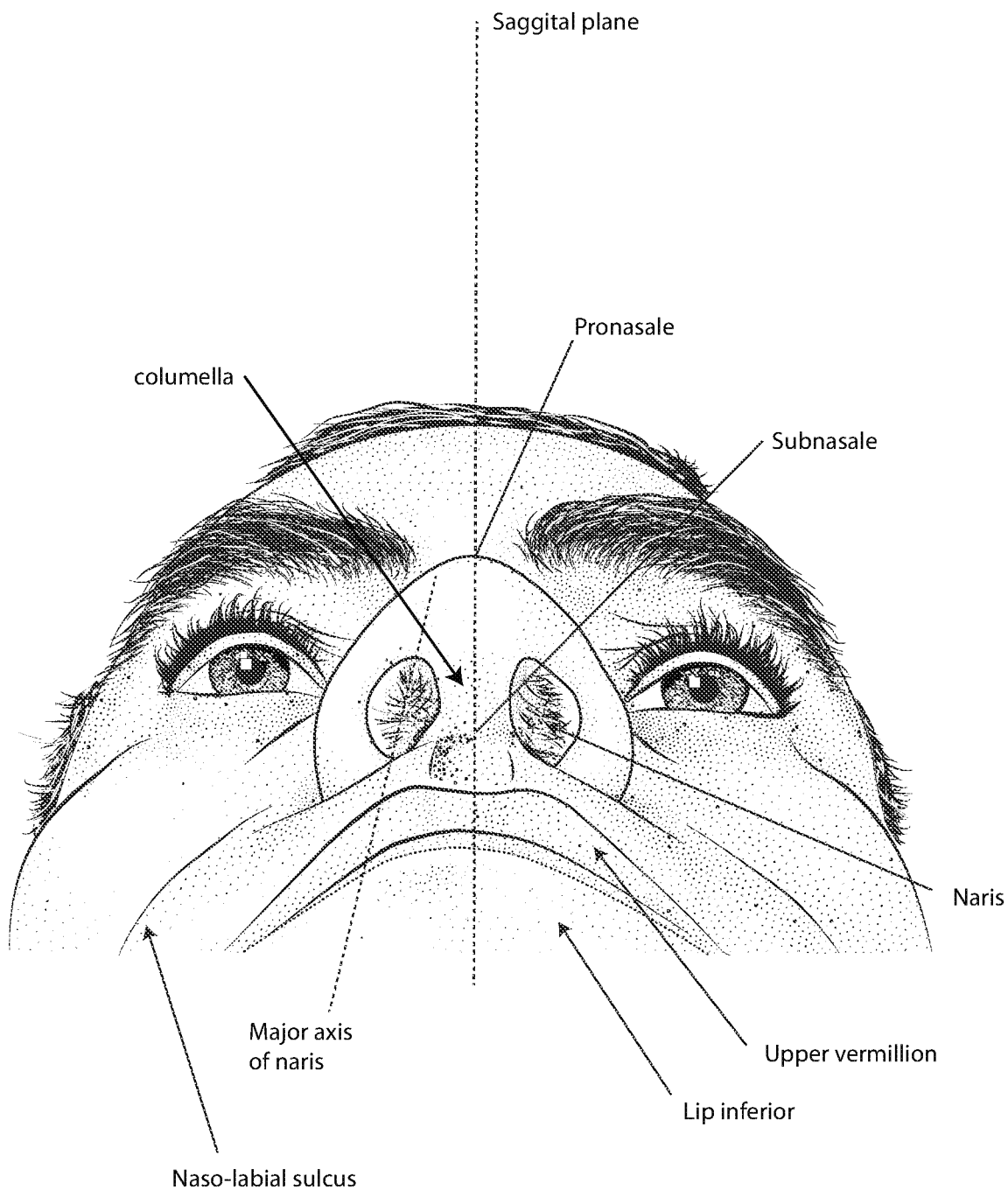

FIG. 2F shows a base view of a nose with several features identified including naso-labial sulcus, lip inferior, upper Vermilion, naris, subnasale, columella, pronasale, the major axis of a naris and the sagittal plane.

Figure 2I:
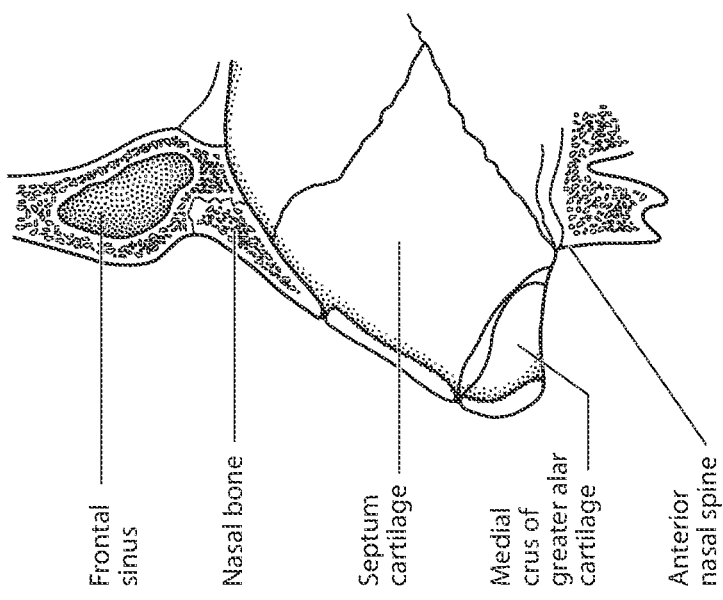
Figure 2H:
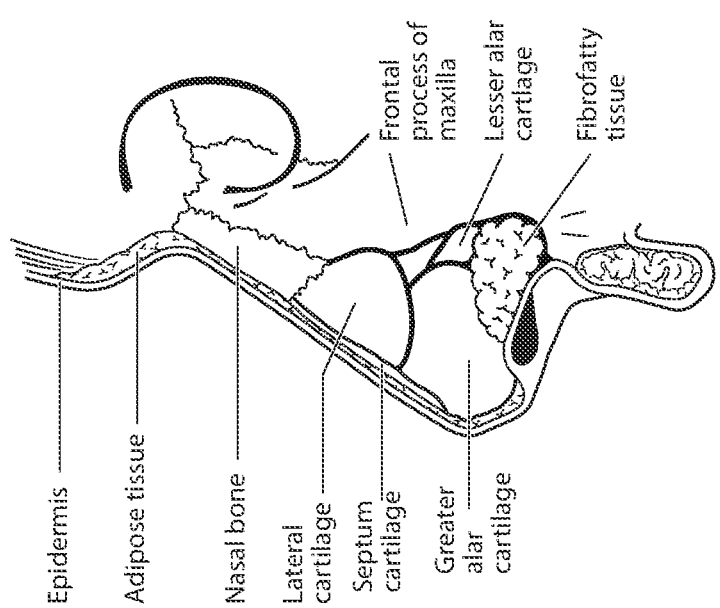
Figure 2G:
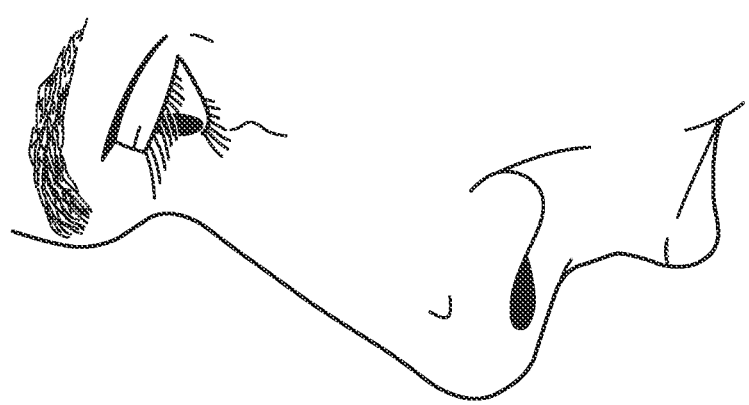

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
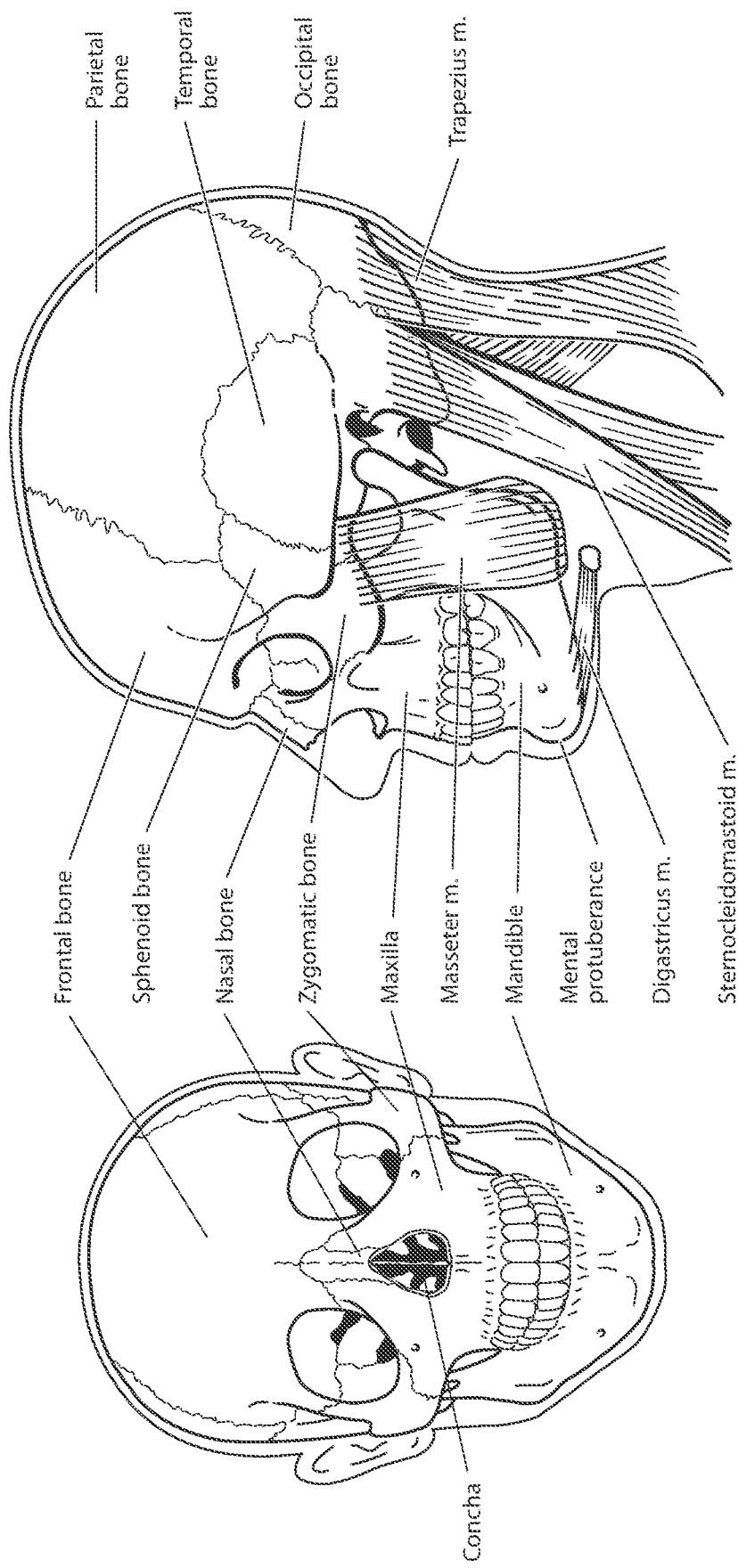

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
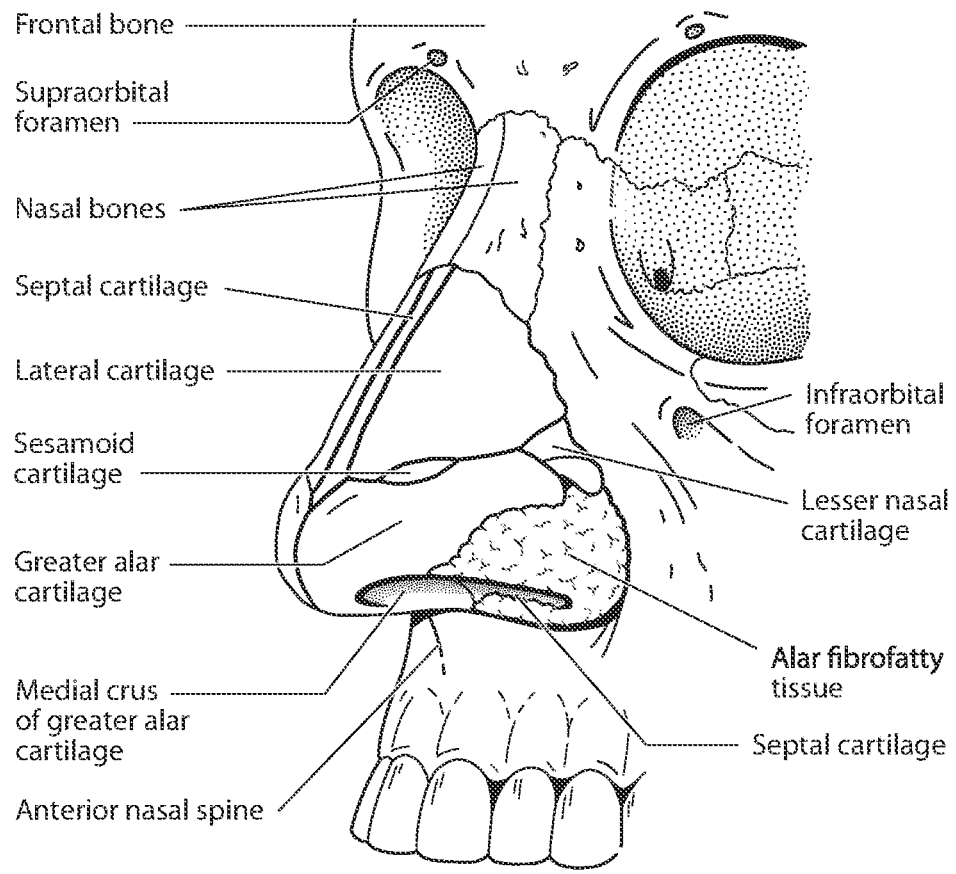

FIG. 2L shows an anterolateral view of a nose.

4.3 Patient Interface

Figure 3A:
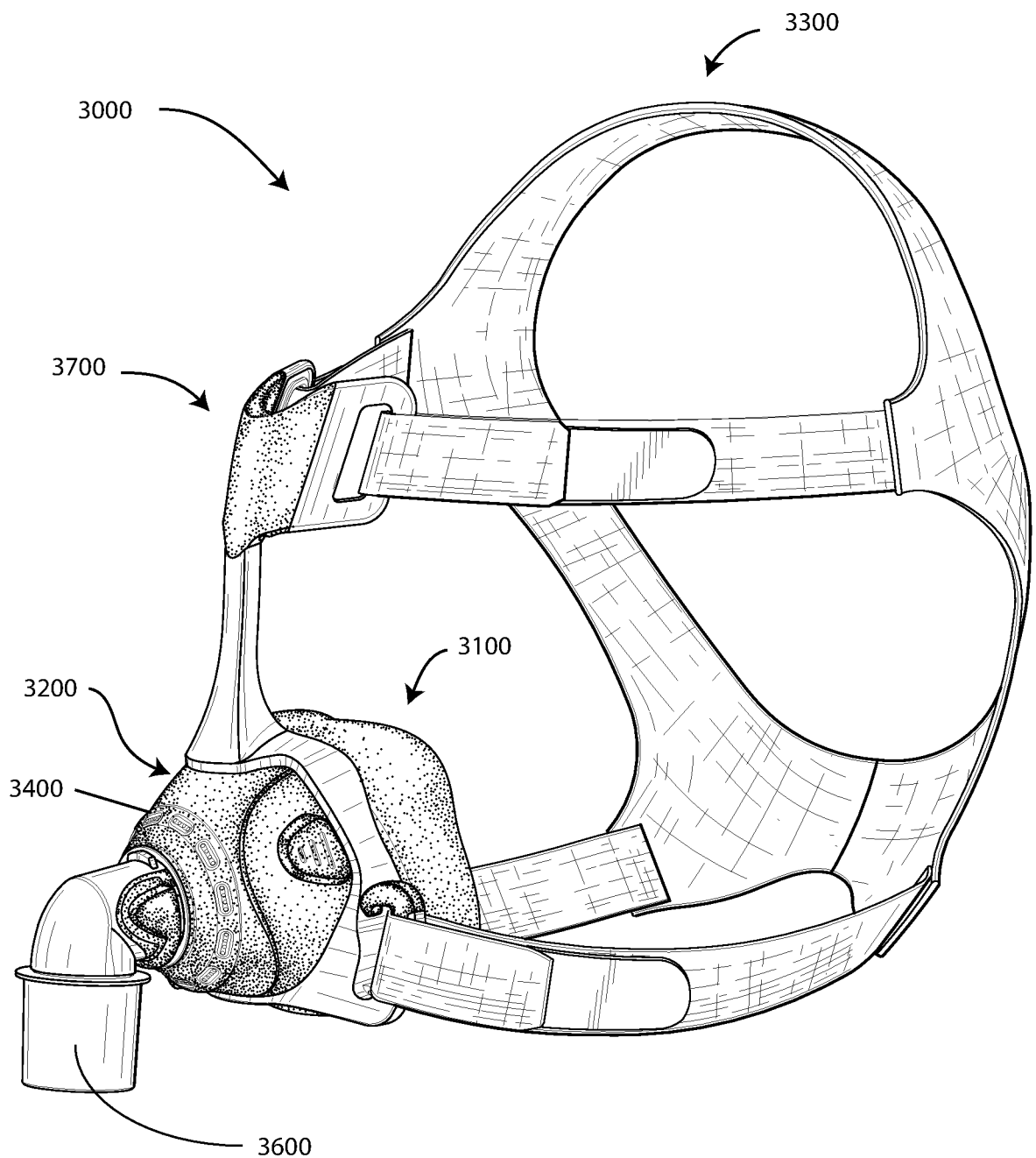

FIG. 3A shows a patient interface in the form of a nasal mask in accordance with one form of the present technology.

4.4 RPT Device

Figure 4A:
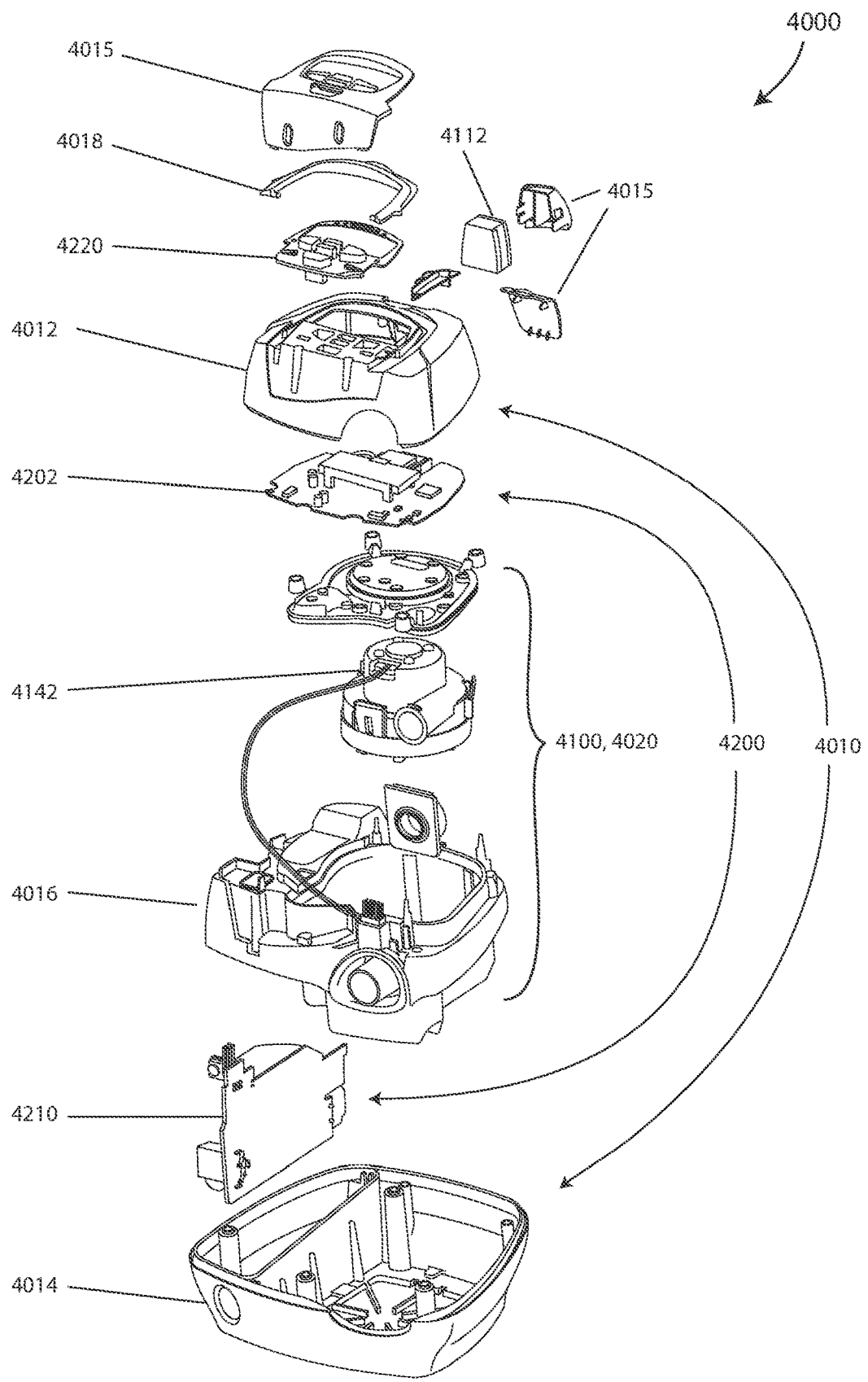

FIG. 4A shows a RPT device in accordance with one form of the present technology.

Figure 4B:
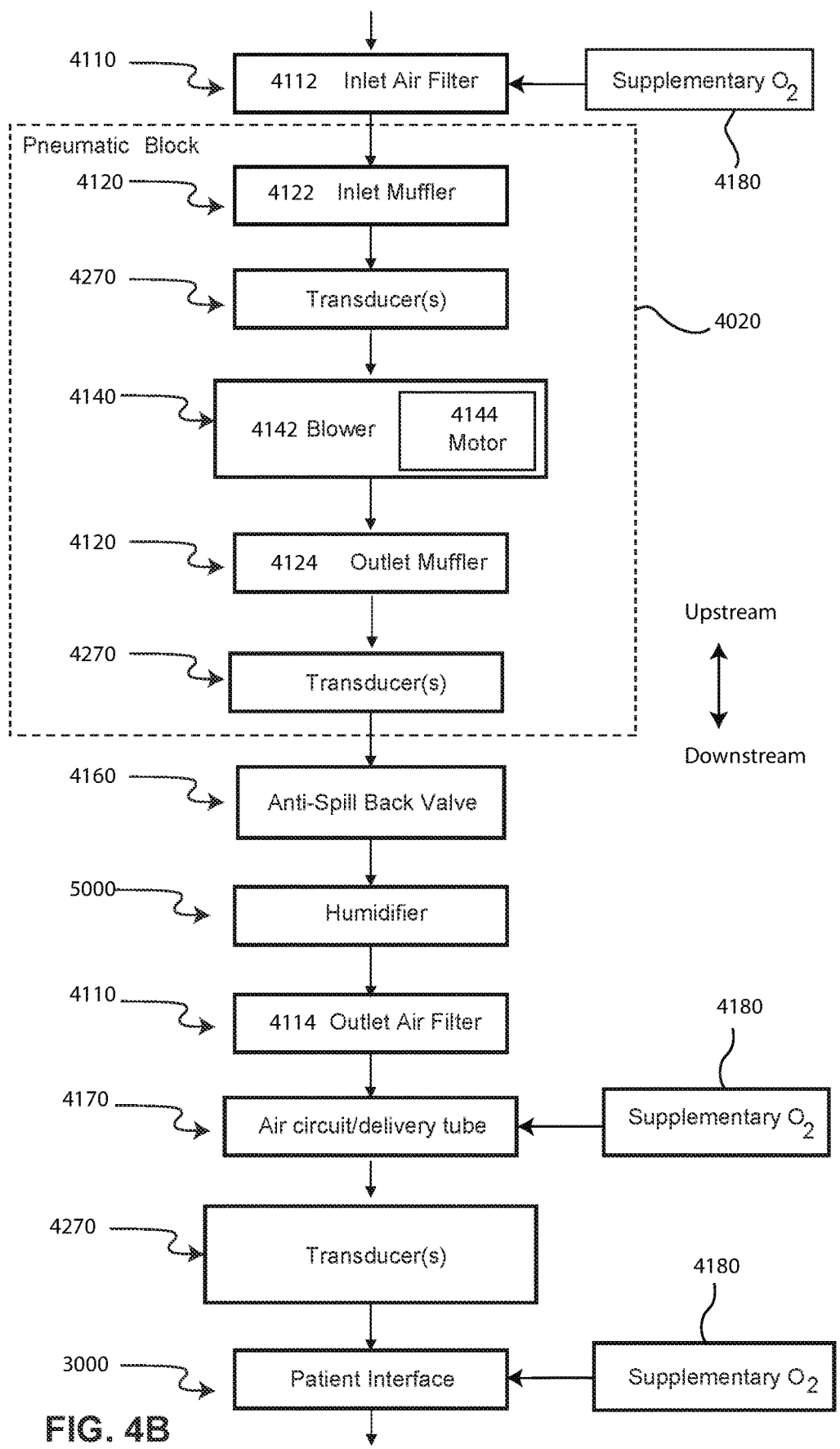

FIG. 4B shows a schematic diagram of the pneumatic path of a RPT device in accordance with one form of the present technology. The directions of upstream and downstream are indicated.

Figure 4C:
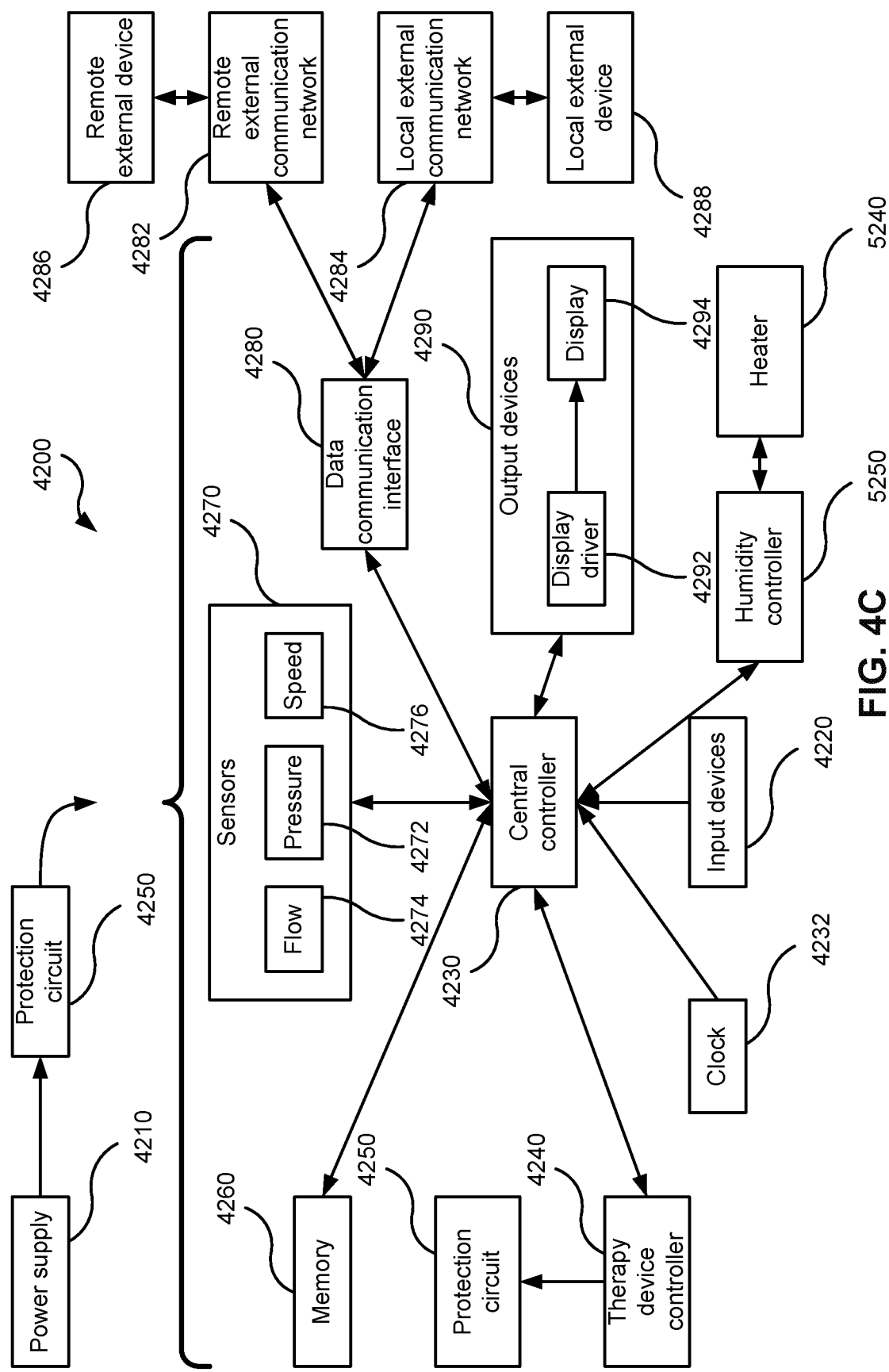

FIG. 4C shows a schematic diagram of the electrical components of a RPT device in accordance with one aspect of the present technology.

Figure 4D:
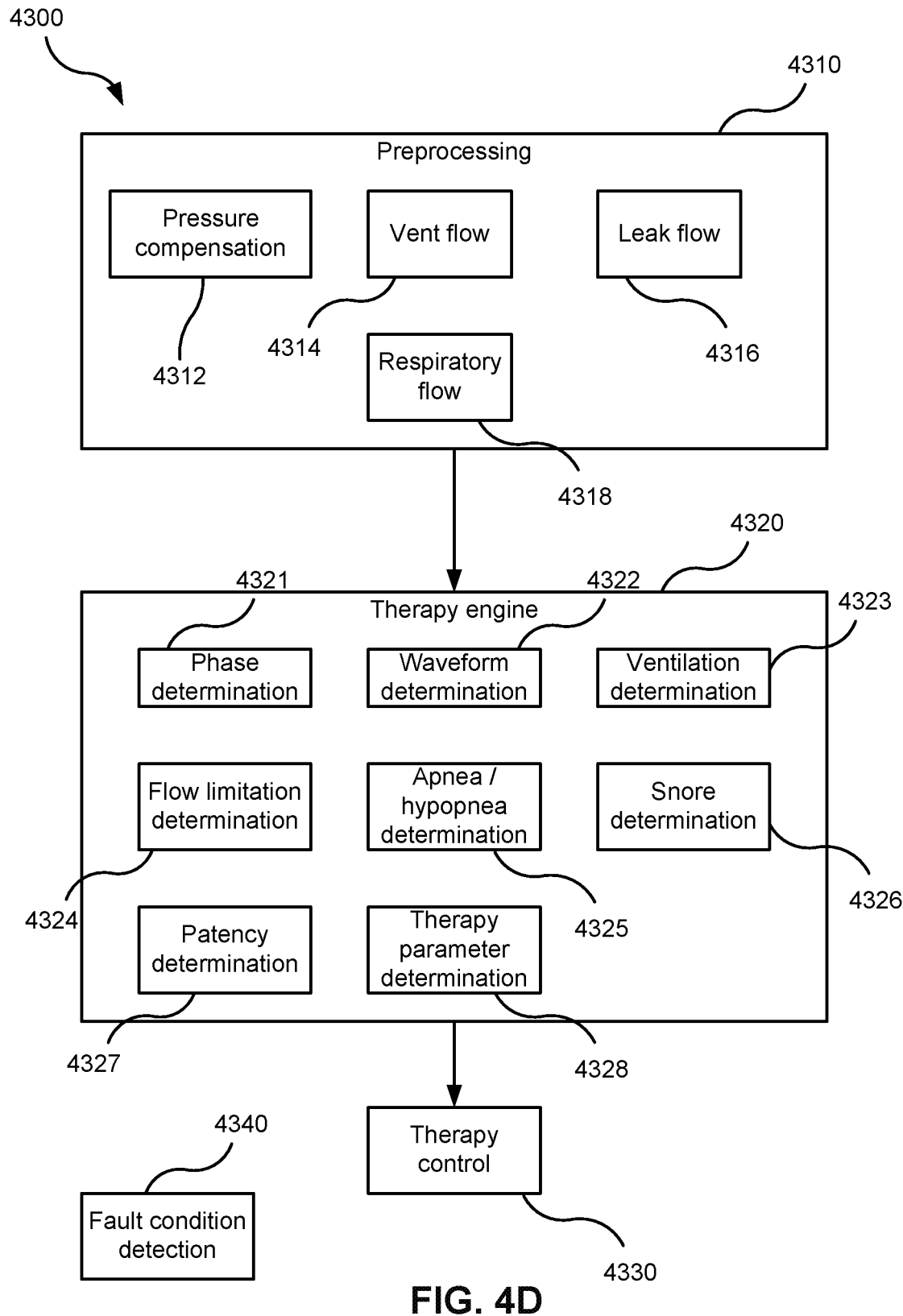

FIG. 4D shows a schematic diagram of the algorithms implemented in a RPT device in accordance with an aspect of the present technology. In this figure, arrows with solid lines indicate an actual flow of information, for example via an electronic signal.

Figure 4E:
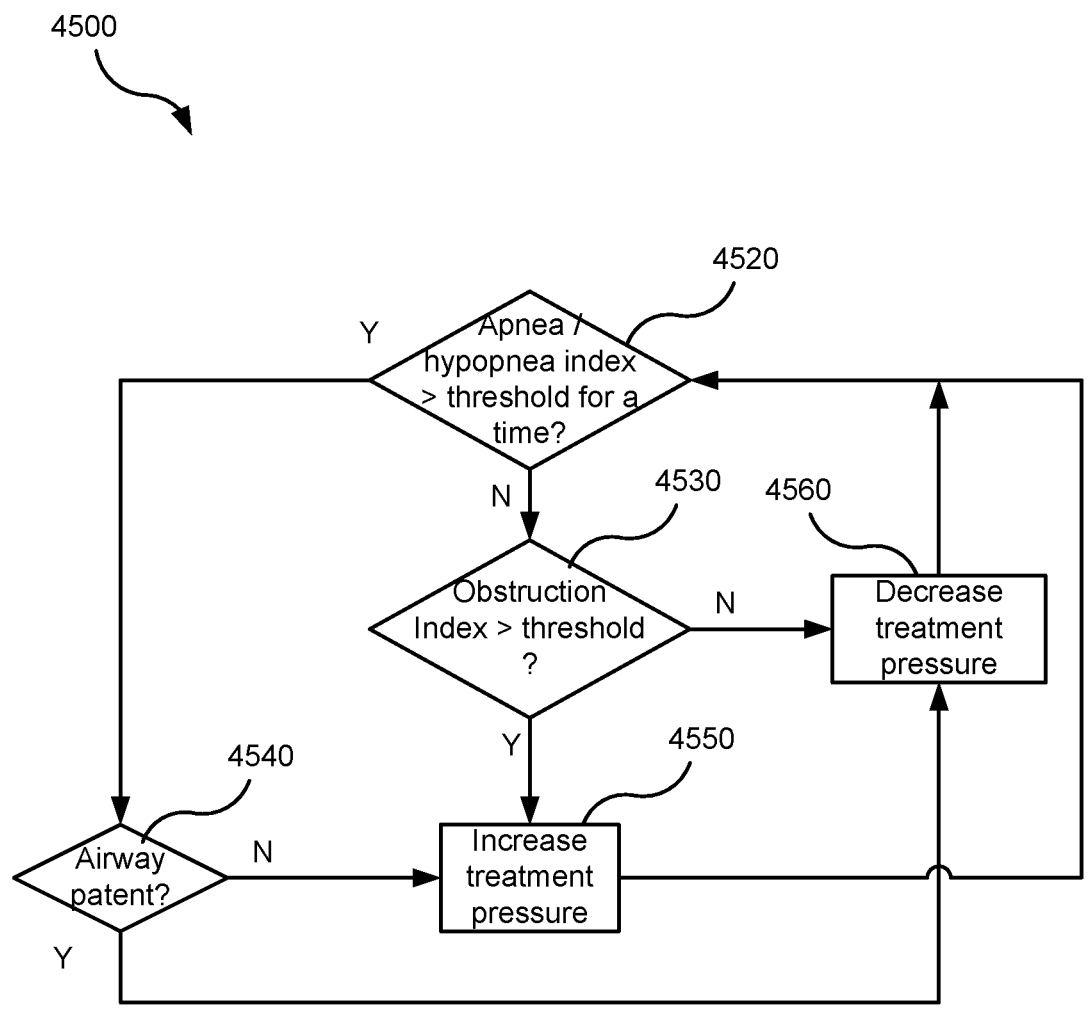

FIG. 4E is a flow chart illustrating a method carried out by the therapy engine module of FIG. 4d in accordance with one aspect of the present technology.

4.5 Humidifier

Figure 5A:
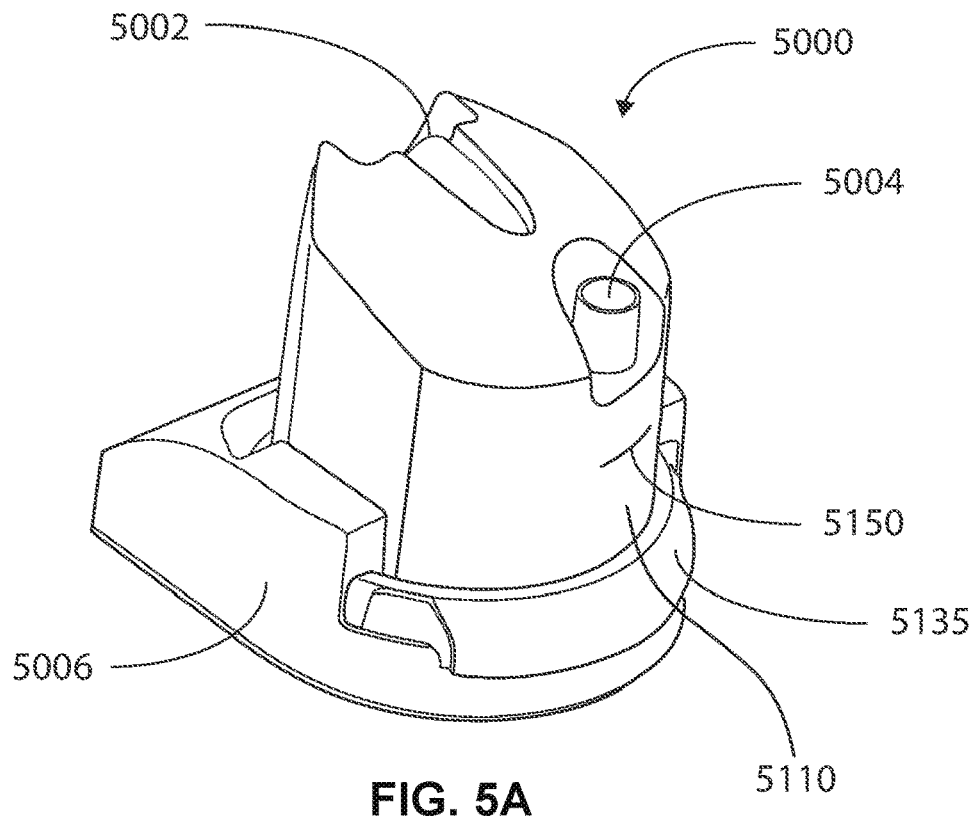

FIG. 5A shows an isometric view of a humidifier in accordance with one aspect of the present technology.

Figure 5B:
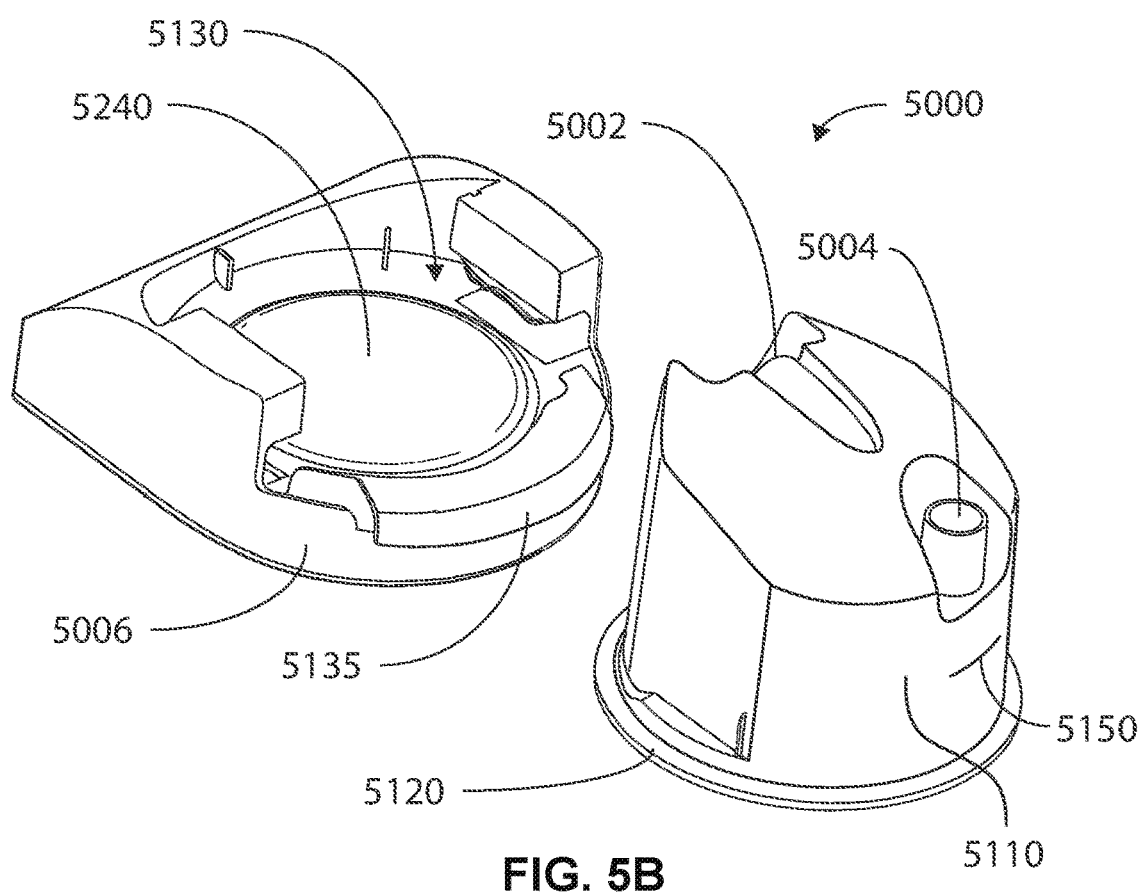

FIG. 5B shows an isometric view of a humidifier in accordance with one aspect of the present technology, showing a humidifier reservoir 5110 removed from the humidifier reservoir dock 5130.

Figure 5C:
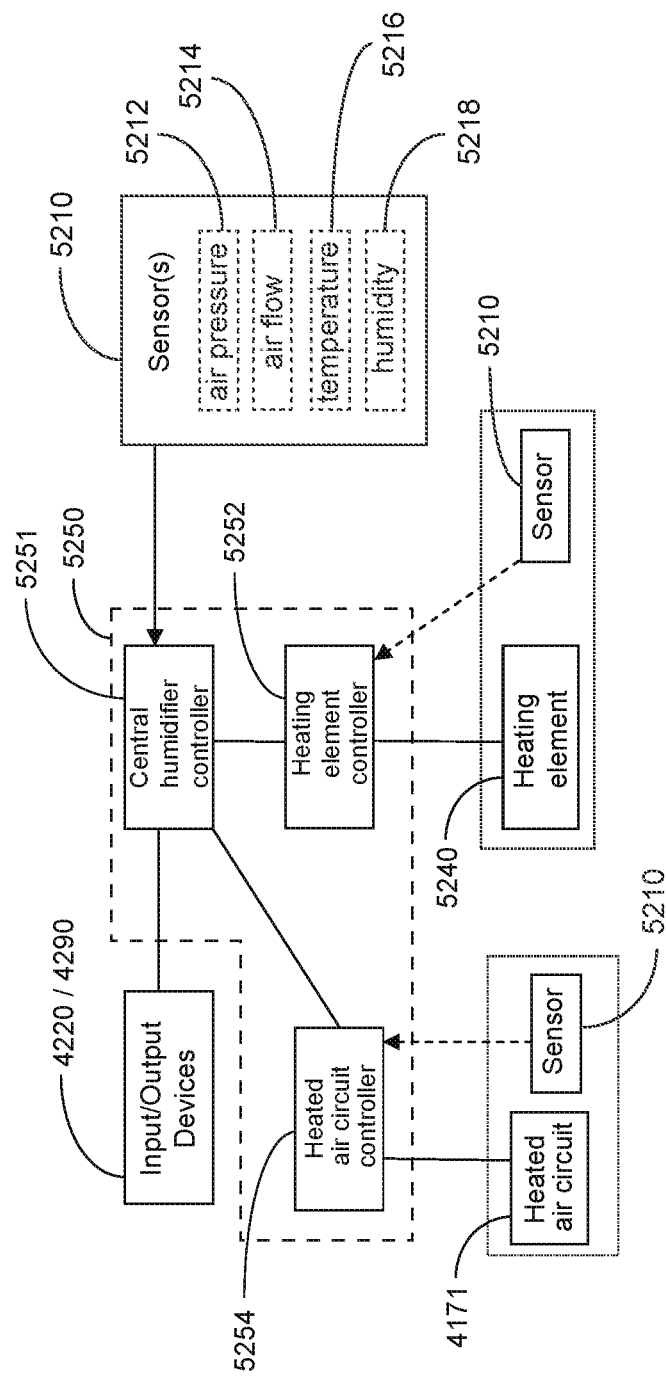

FIG. 5C shows a schematic of a humidifier in accordance with one aspect of the present technology.

4.6 Breathing Waveforms

Figure 6A:
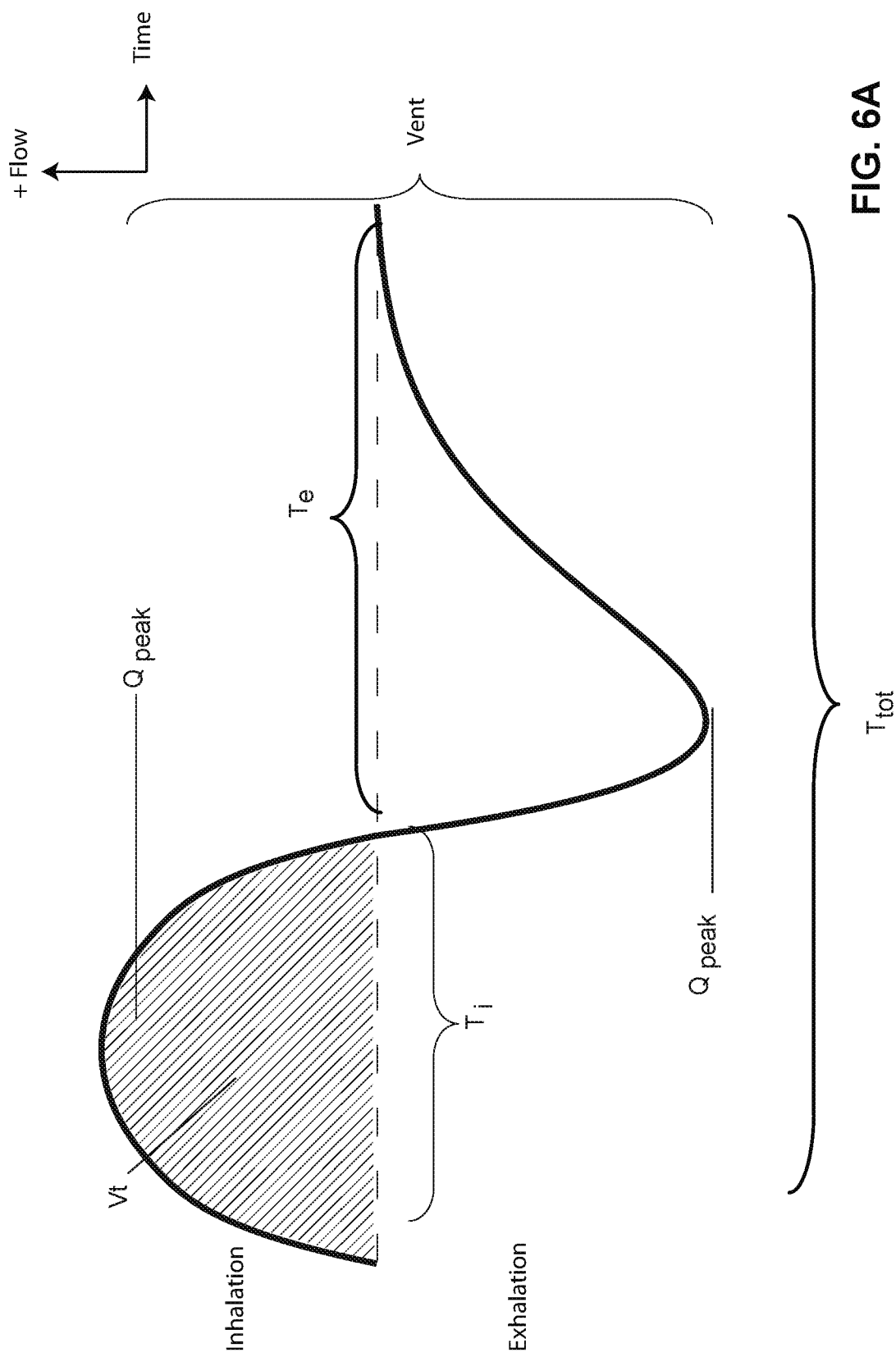

FIG. 6A shows a model typical breath waveform of a person while sleeping.

Figure 6B:
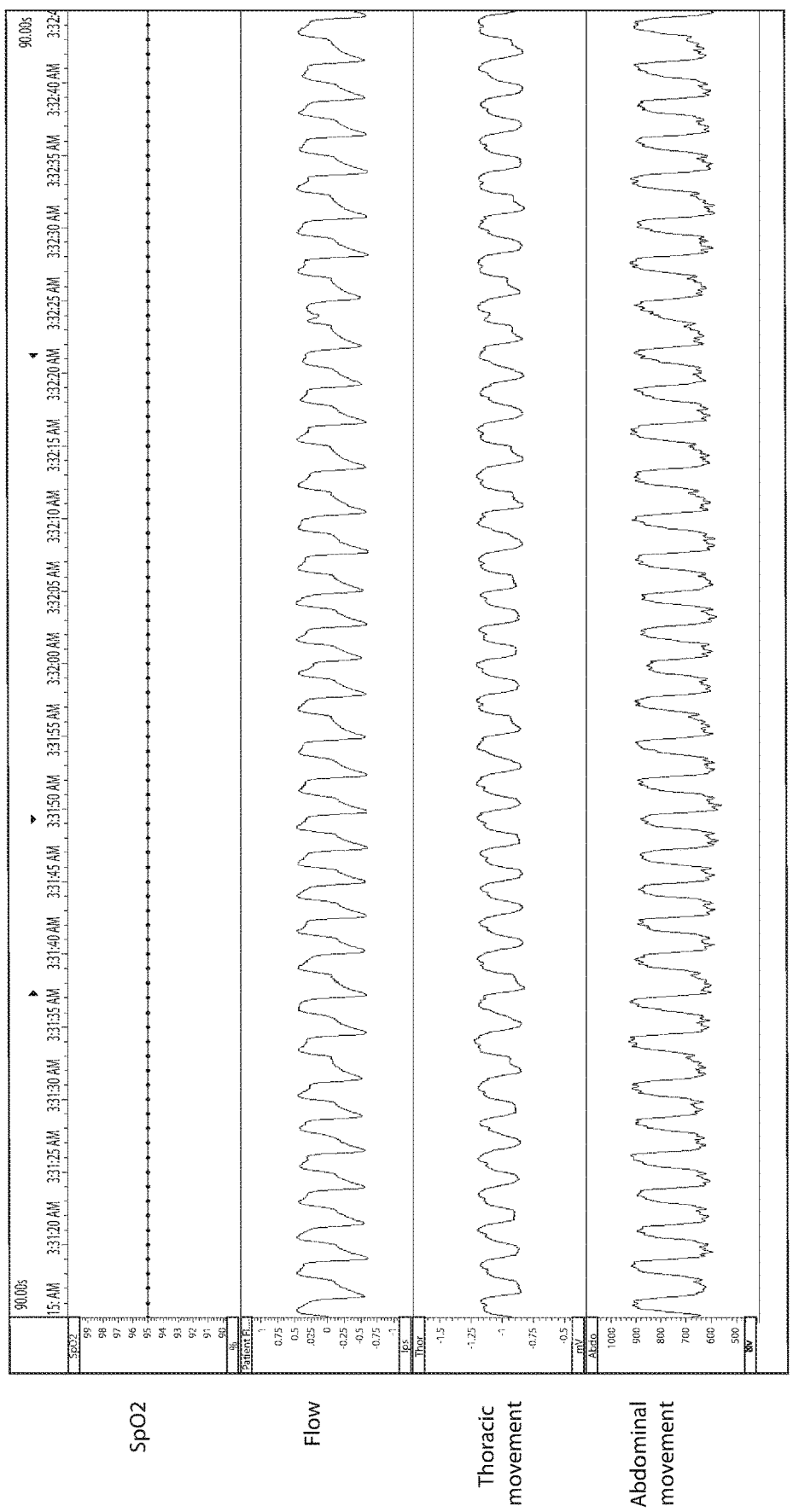

FIG. 6*b* shows a patient during Non-REM sleep breathing normally over a period of about ninety seconds.

Figure 6C:
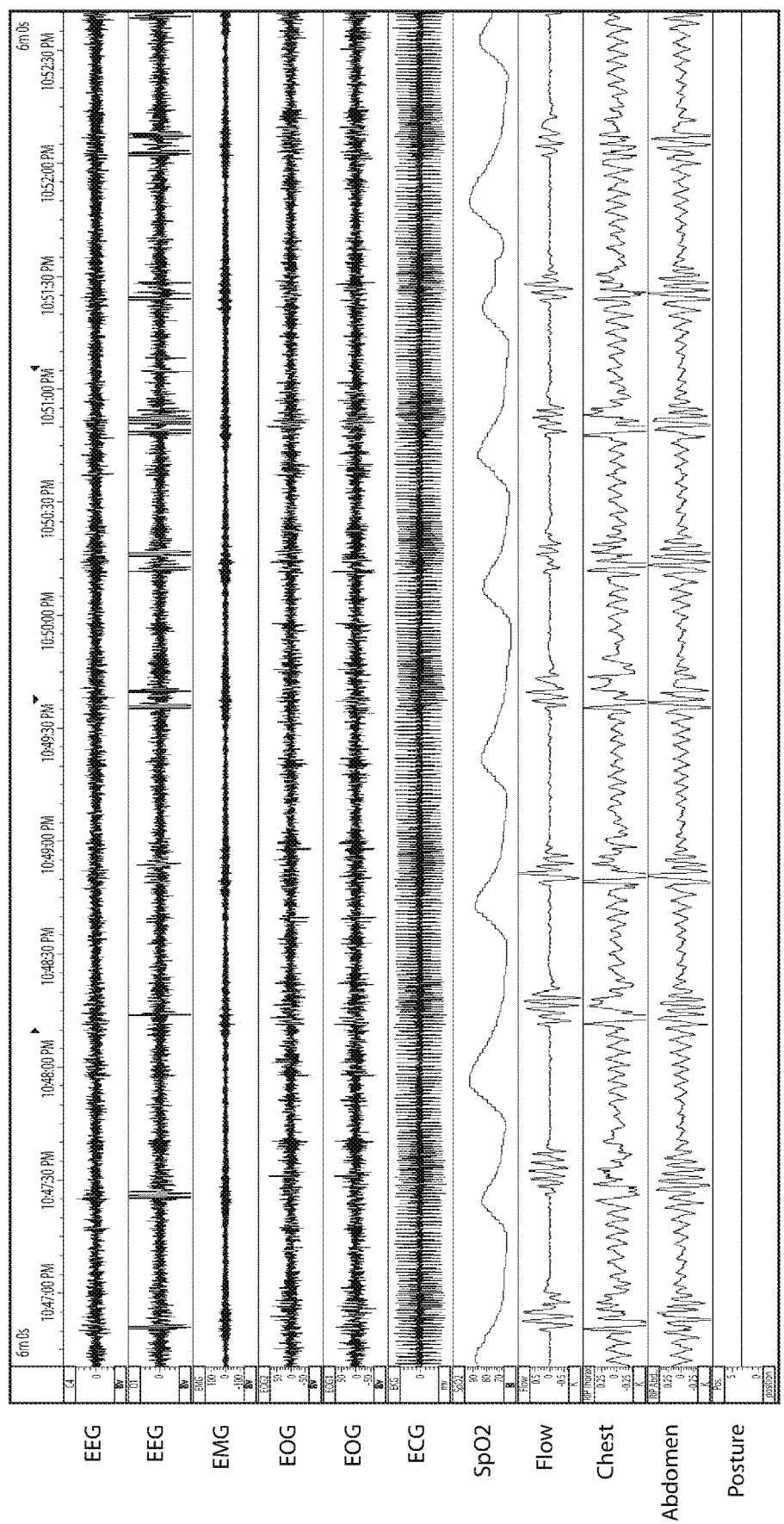

FIG. 6C shows polysomnography of a patient before treatment.

Figure 6D:
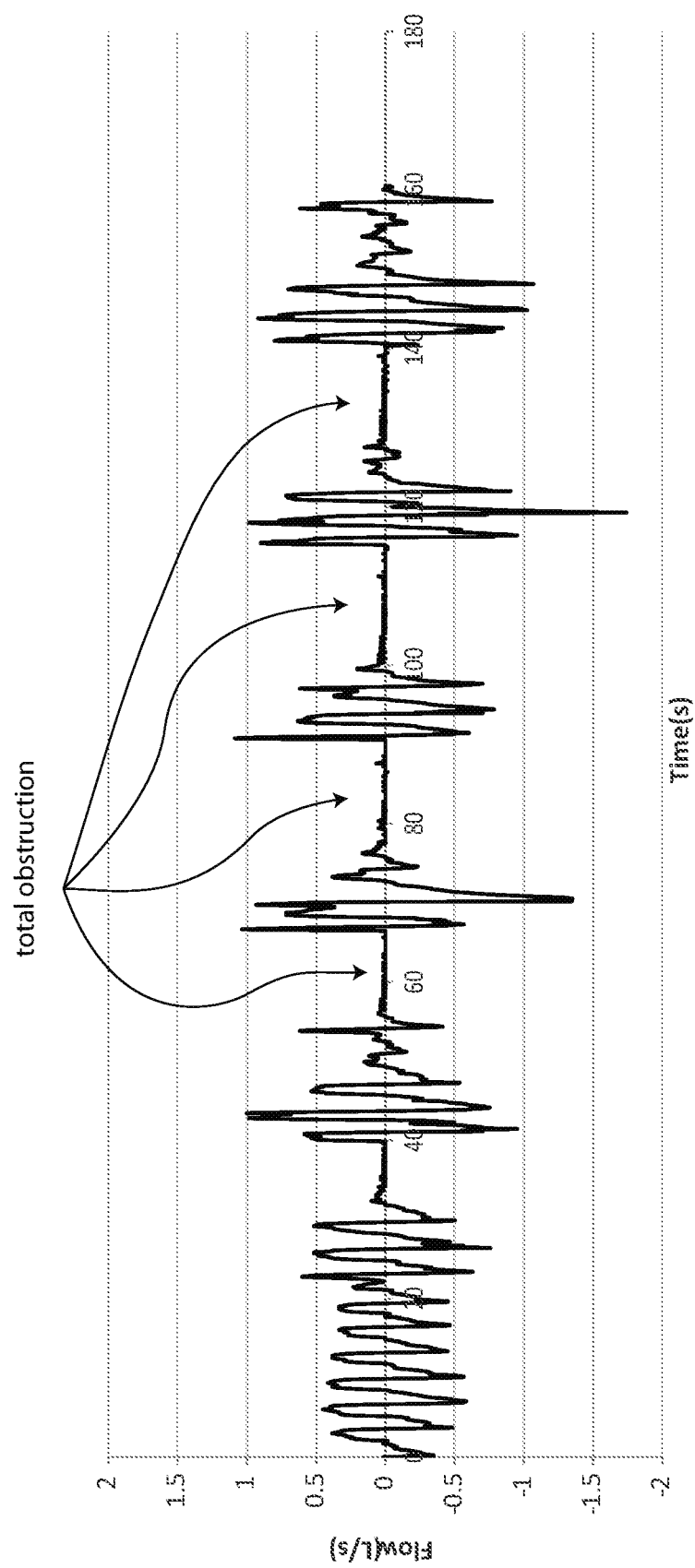

FIG. 6D shows patient flow data where the patient is experiencing a series of total obstructive apneas.

Figure 6E:
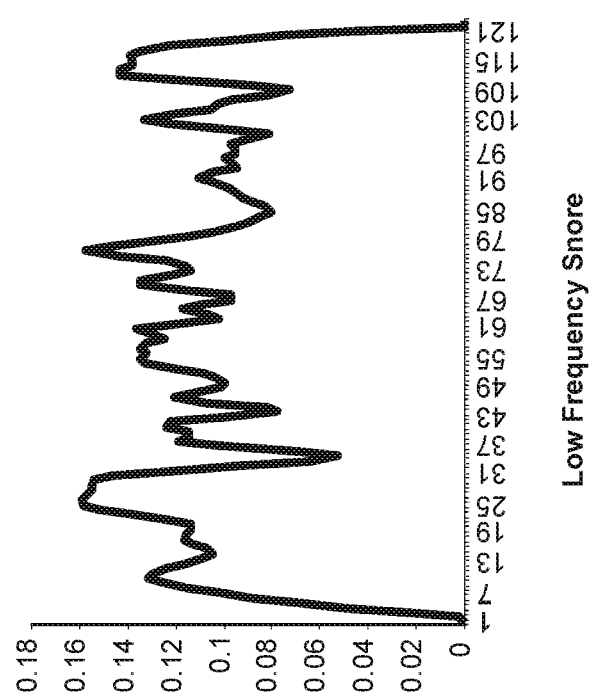

FIG. 6E shows a scaled inspiratory portion of a breath where the patient is experiencing low frequency inspiratory snore.

4.7 Heat and Moisture Exchanger

Figure 7A:
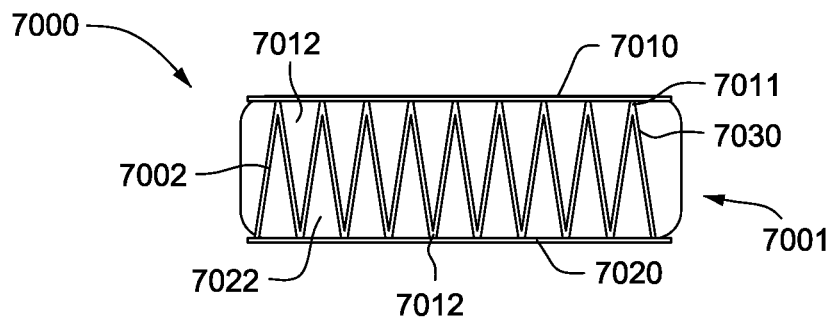

FIG. 7A shows a cross sectional view of a HME 7000 comprising a single layer 7001 in accordance with one aspect of the present technology.

Figure 7B:
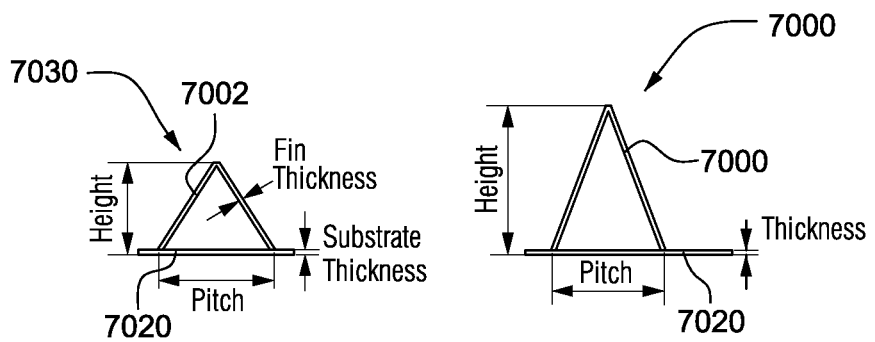

FIG. 7B shows examples of a single corrugation 7030 of a HME 7000 in accordance with one aspect of the present technology.

Figure 7C:
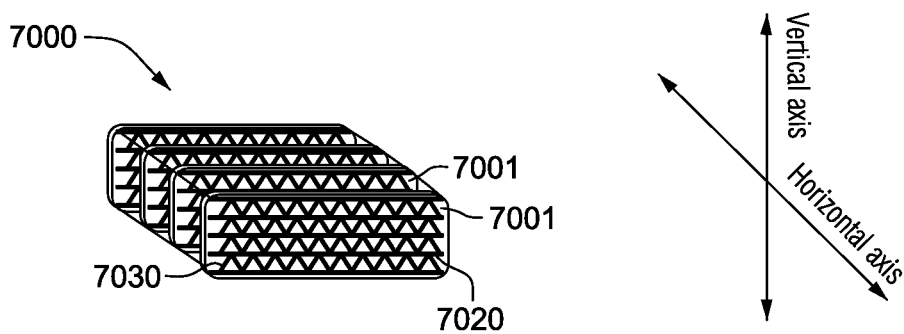

FIG. 7C is a schematic diagram showing a HME 7000 comprising a plurality of layers 7001 stacked along both a vertical and horizontal axis.

Figure 7D:
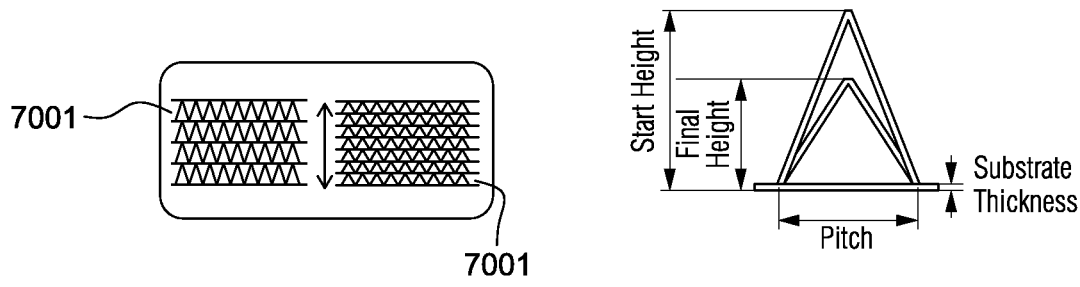

FIG. 7D is a diagram that illustrates a HME under preload to compress the corrugations in a fixed volume such that the number of layers 7001 is increased within the fixed volume.

Figure 8A:
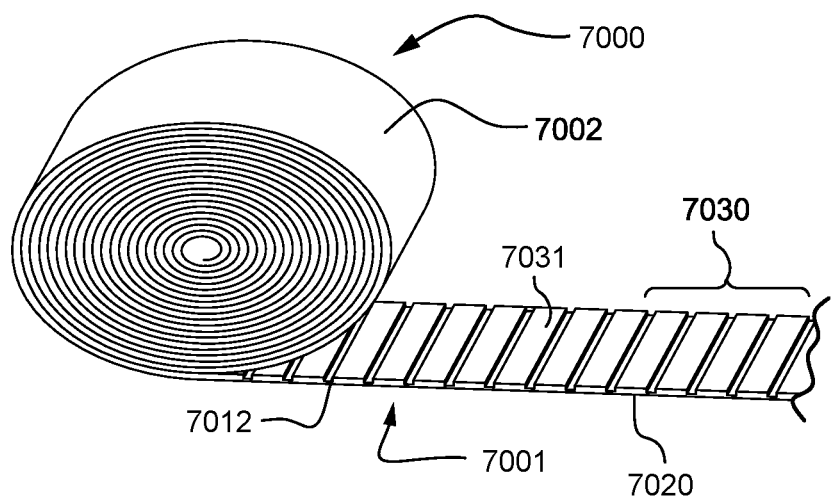

FIG. 8A displays a corrugated structure 7002 comprising a plurality of corrugations 7030, wherein the corrugated structure is rolled to form a HME 7000.

Figure 8B:
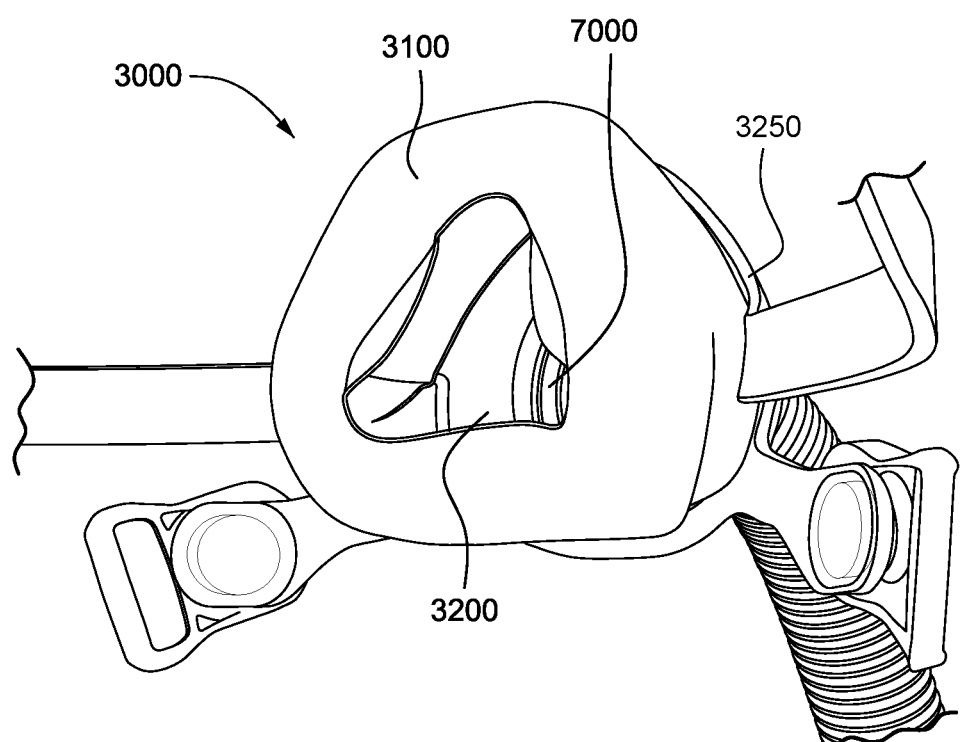

FIG. 8B shows an example of a patient interface 3000 comprising a HME 7000 positioned within the plenum chamber 3200 according to the present technology.

Figure 8C:
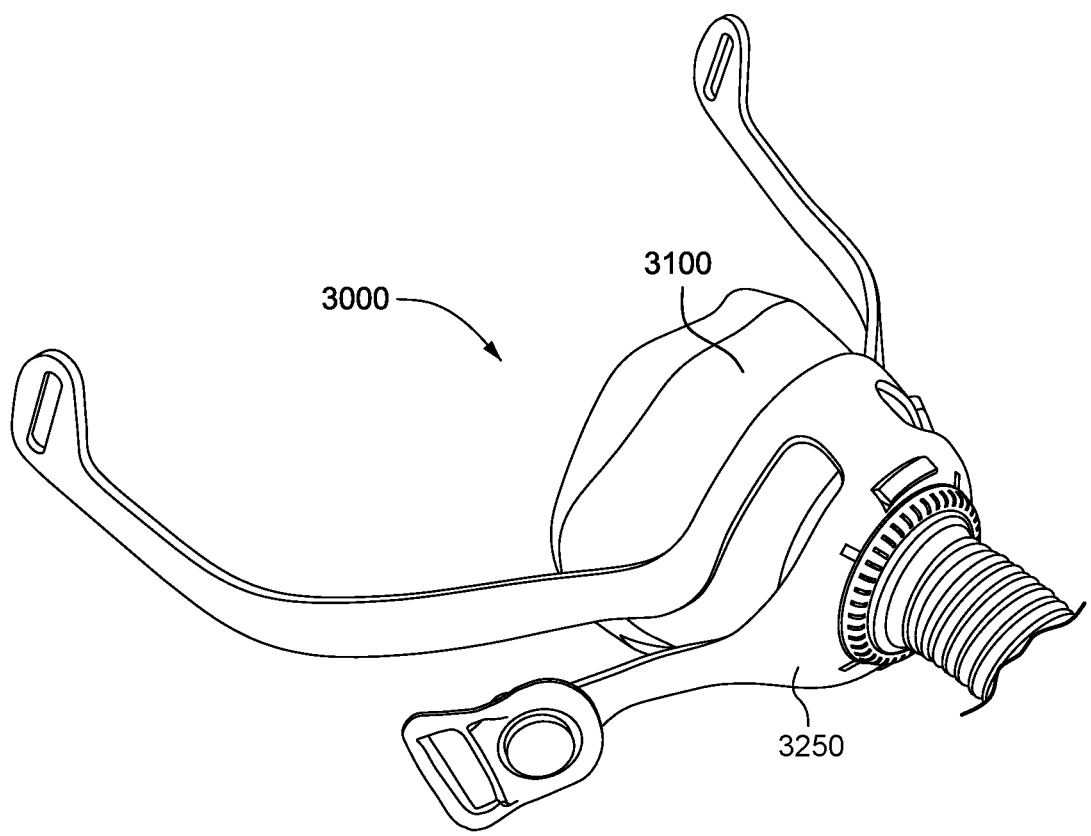

FIG. 8C shows an example of a patient interface 3000 comprising a HME 7000 positioned within the plenum chamber 3200 according to the present technology.

Figure 8D:
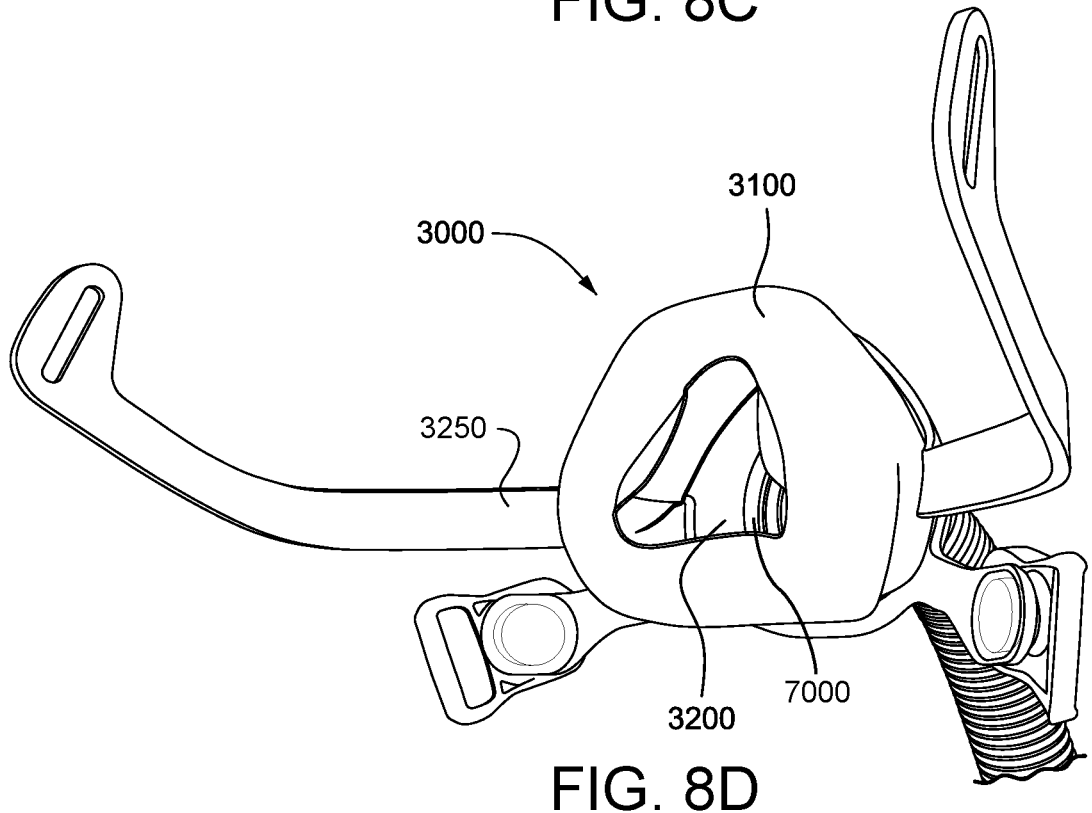

FIG. 8D shows an example of a patient interface 3000 comprising a HME 7000 positioned within the plenum chamber 3200 according to the present technology.

Figure 9A:
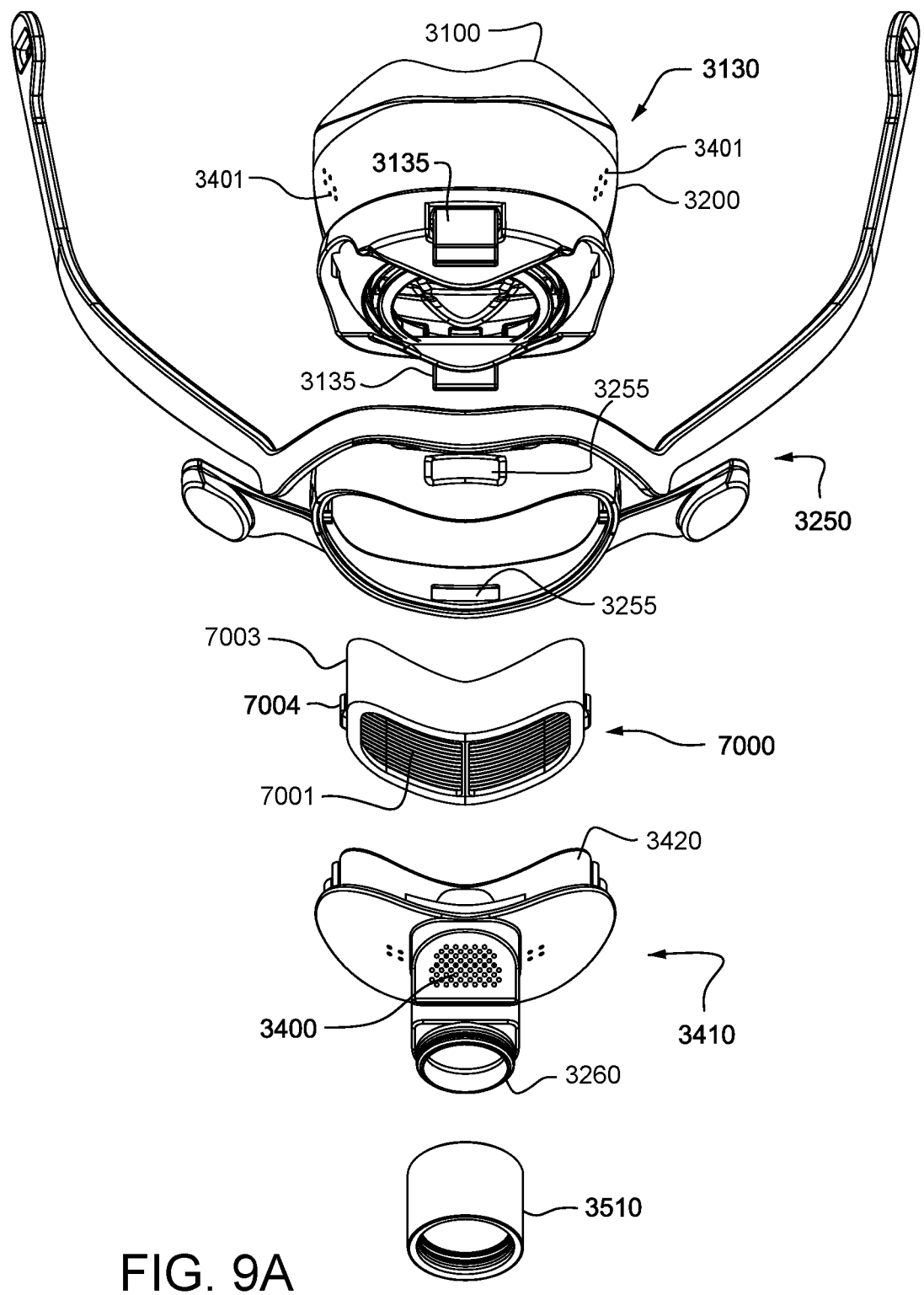

FIG. 9A displays an exploded view of another patient interface 3000 comprising a HME 7000 and housed within a vent adaptor 3410 according to the present technology.

Figure 9B:
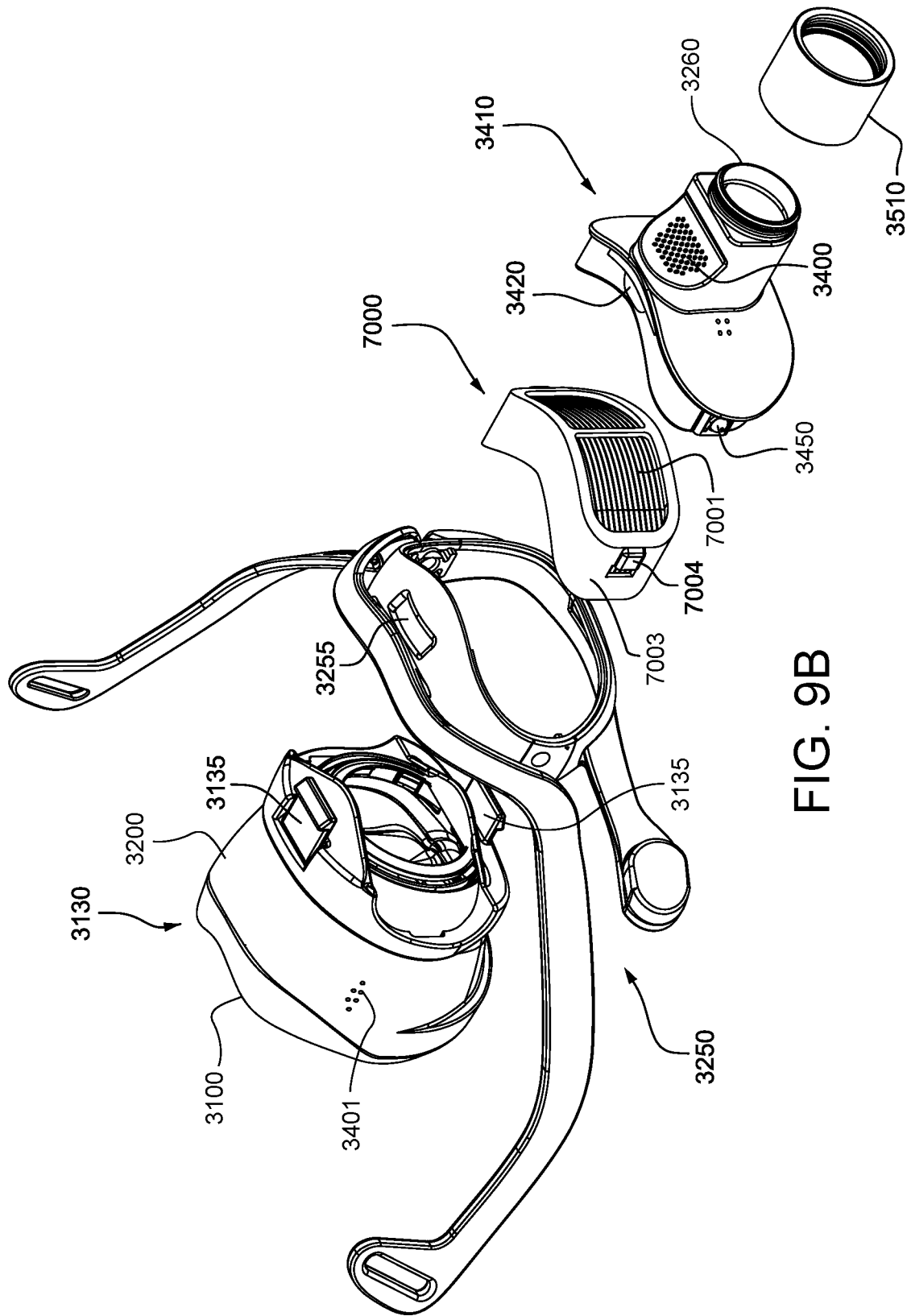

FIG. 9B displays an exploded view of another patient interface 3000 comprising a HME 7000 and housed within a vent adaptor 3410 according to the present technology.

Figure 9C:
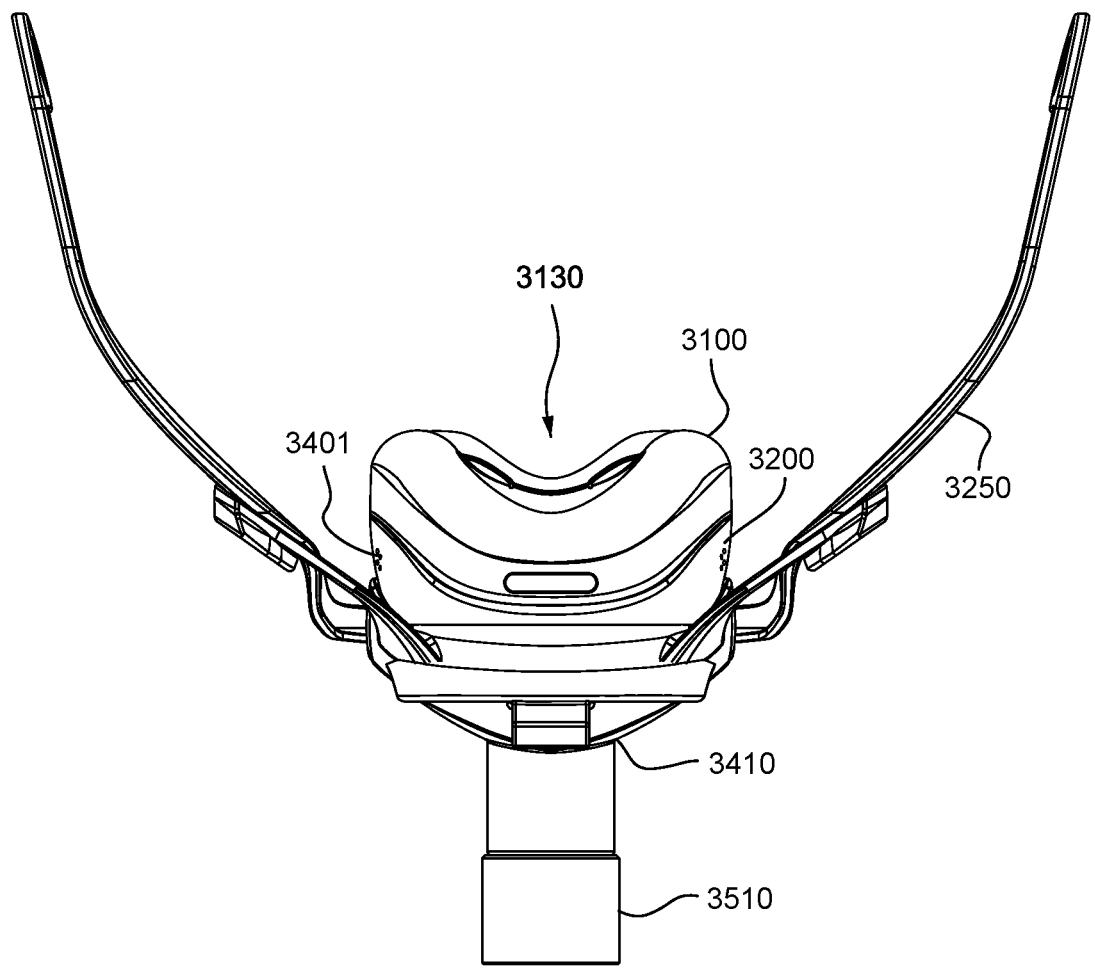

FIG. 9C displays a top view of a further example of a patient interface 3000 in accordance with the present technology.

Figure 9D:
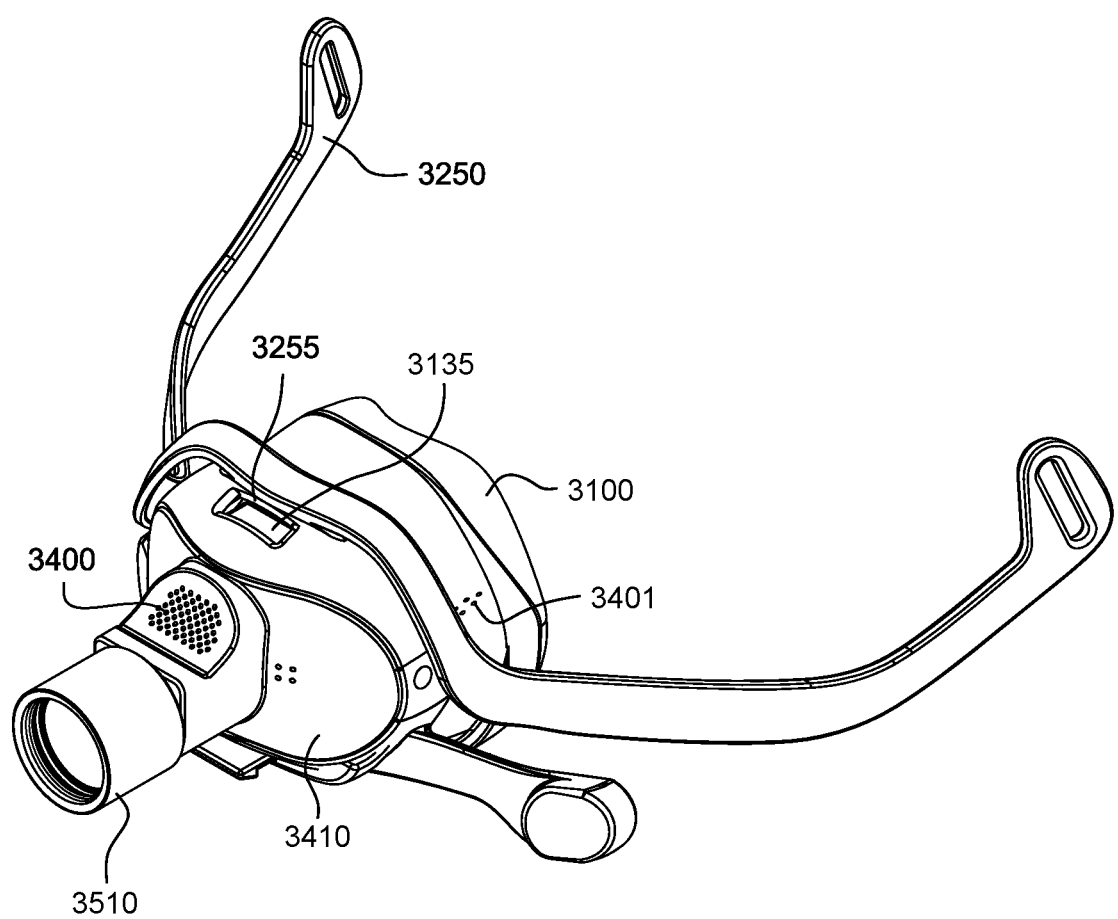

FIG. 9D displays a perspective view of a further example of a patient interface 3000 in accordance with the present technology.

Figure 9E:
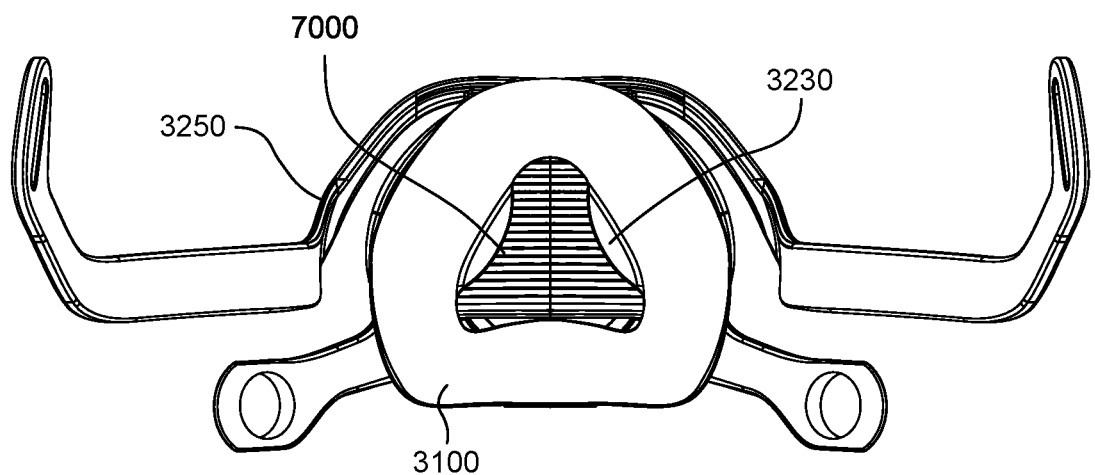

FIG. 9E displays a posterior view of a further example of a patient interface 3000 in accordance with the present technology.

Figure 9F:
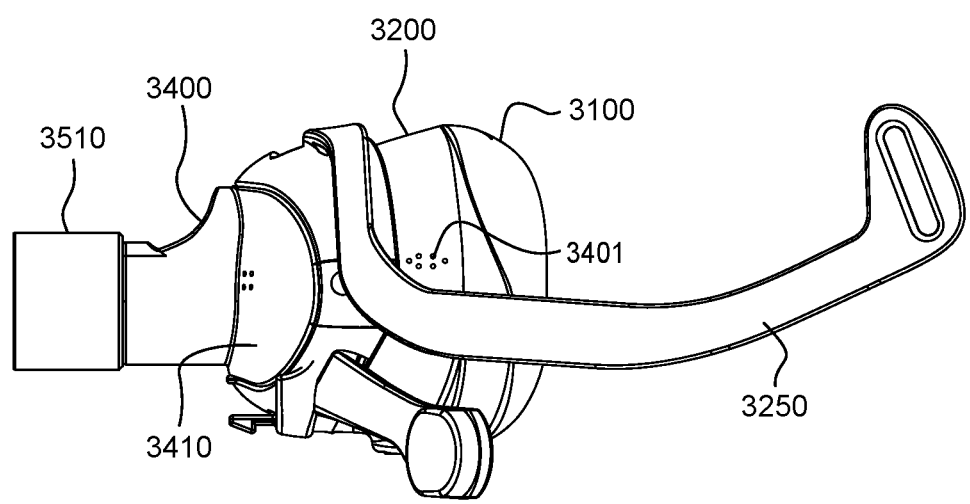

FIG. 9F displays a side view of a further example of a patient interface 3000 in accordance with the present technology.

Figure 9G:
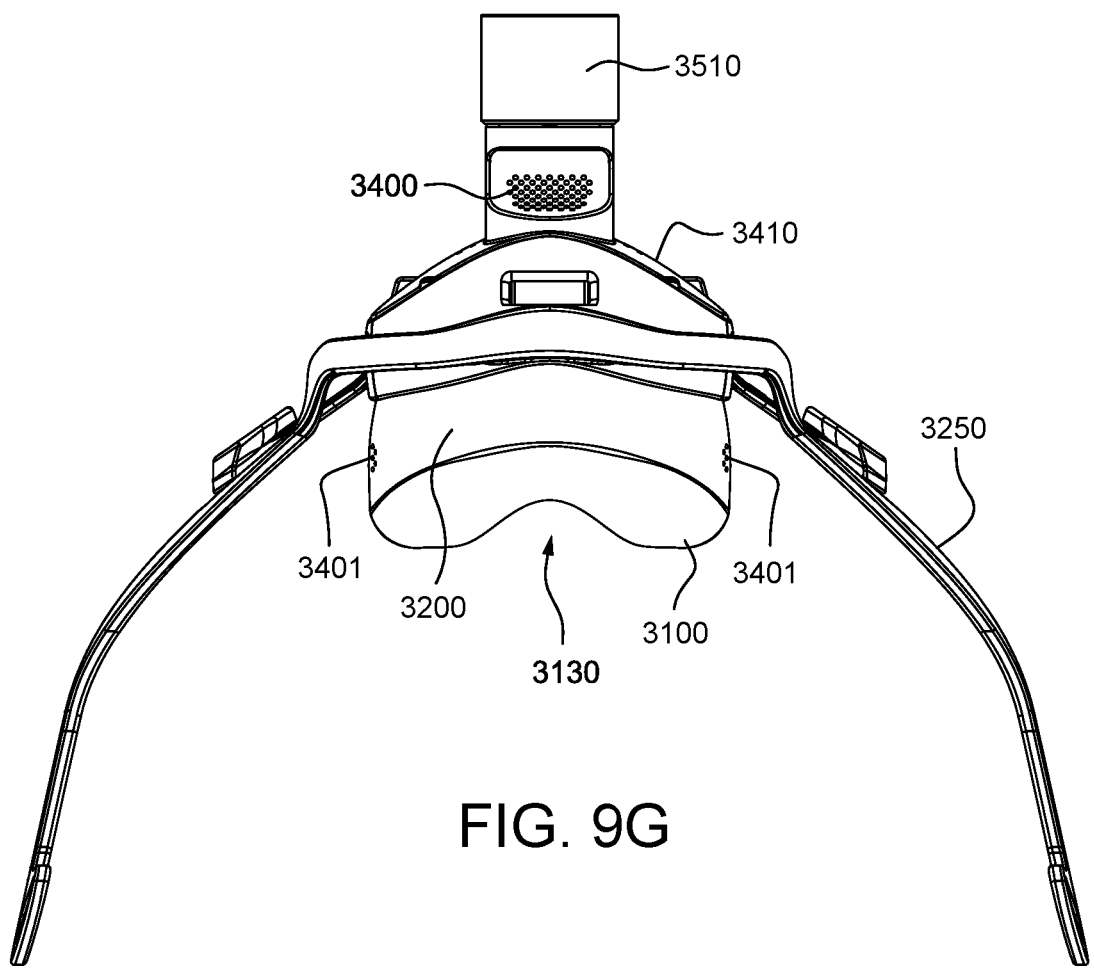

FIG. 9G displays a bottom view of a further example of a patient interface 3000 in accordance with the present technology.

Figure 9H:
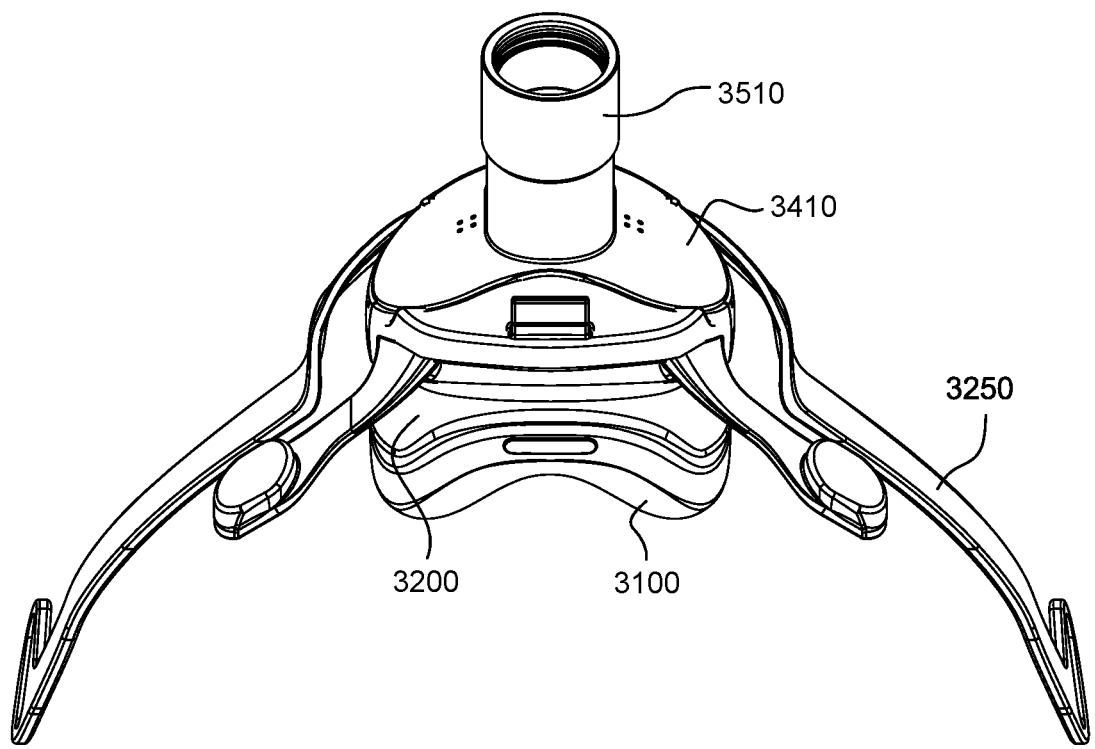

FIG. 9H displays a bottom perspective view of a further example of a patient interface 3000 in accordance with the present technology.

Figure 9I:
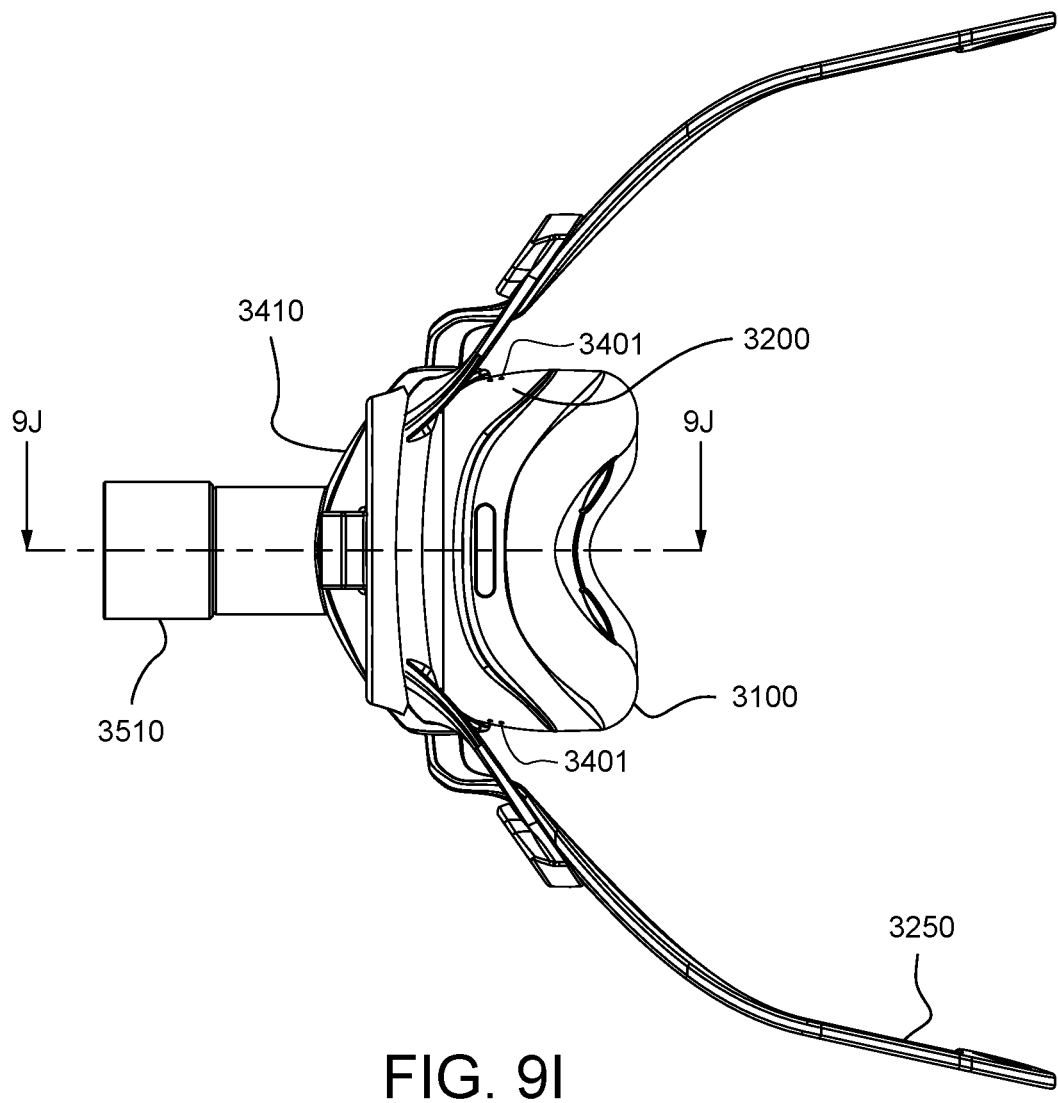

FIG. 9I displays a bottom perspective view of a further example of a patient interface 3000 in accordance with the present technology.

Figure 9J:
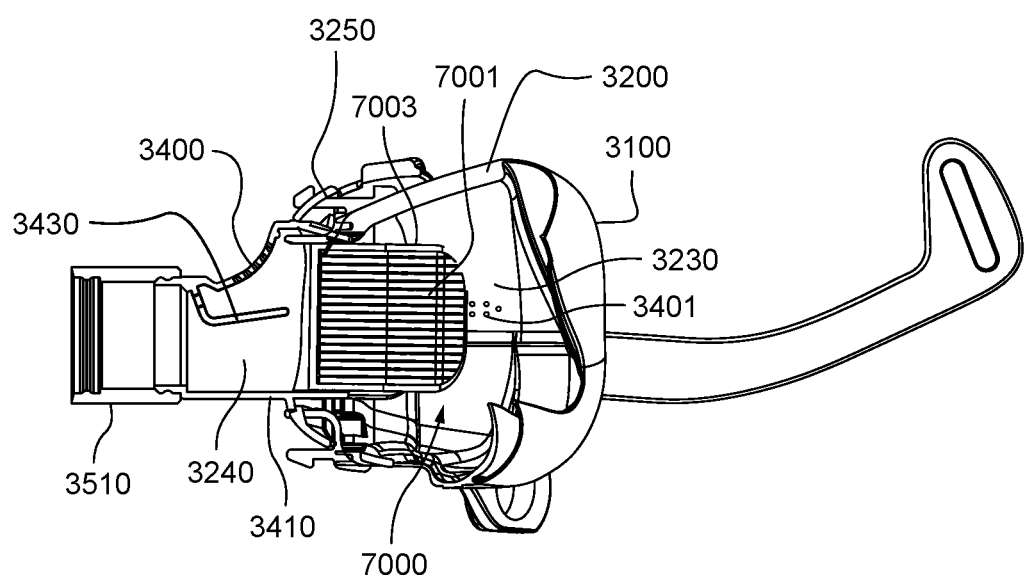

FIG. 9J displays a cross sectional view of a further example of a patient interface 3000 taken through line 9J-9J of FIG. 9 in accordance with the present technology.

Figure 10A:
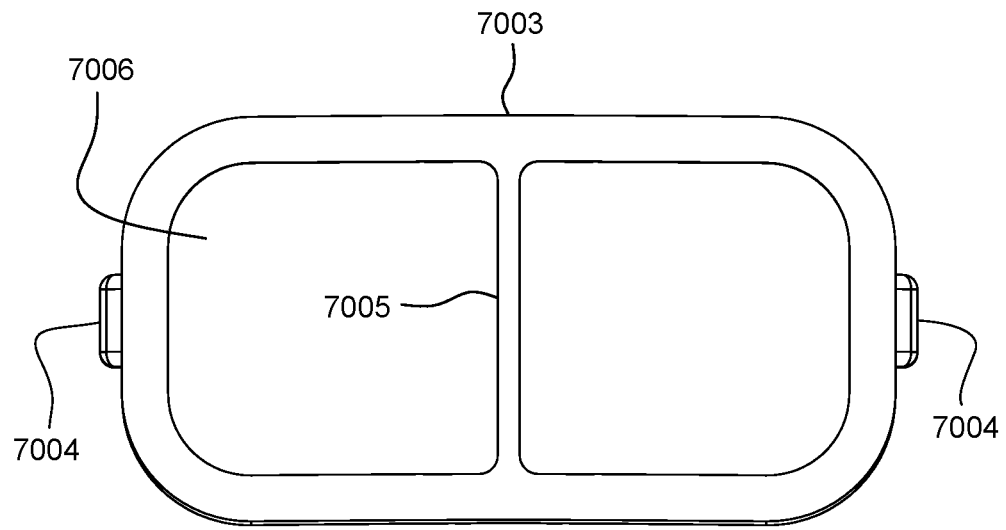

FIG. 10A shows an anterior view of the HME frame 7003 of the removable HME 7000.

Figure 10B:
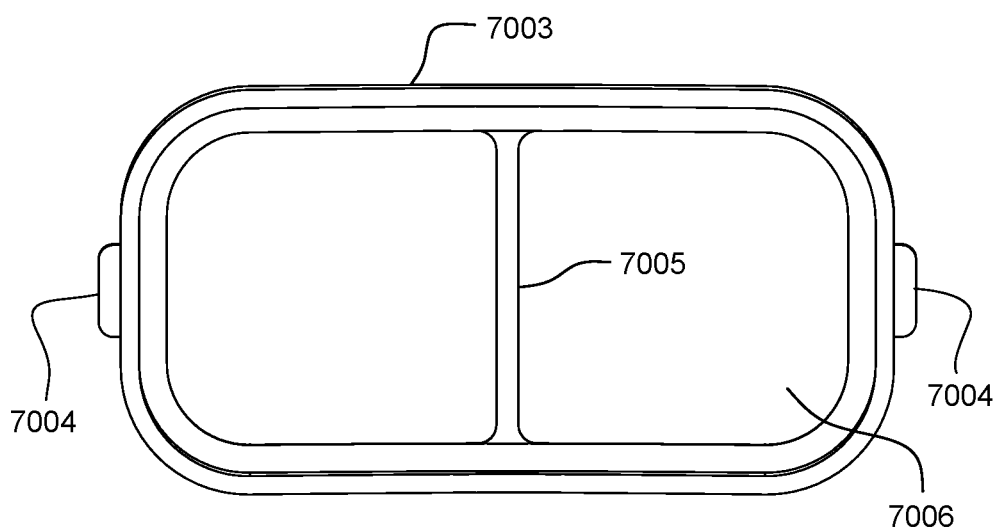

FIG. 10B shows a posterior view of the HME frame 7003 of the removable HME 7000.

Figure 10C:
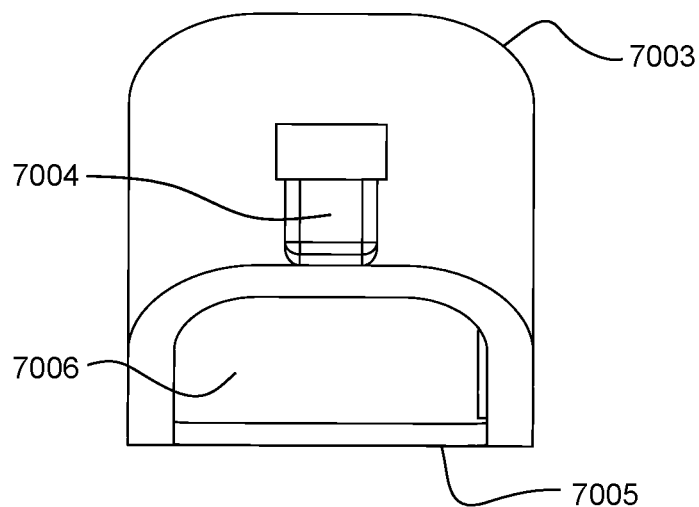

FIG. 10C shows a side view of the HME frame 7003 of the removable HME 7000.

Figure 10D:
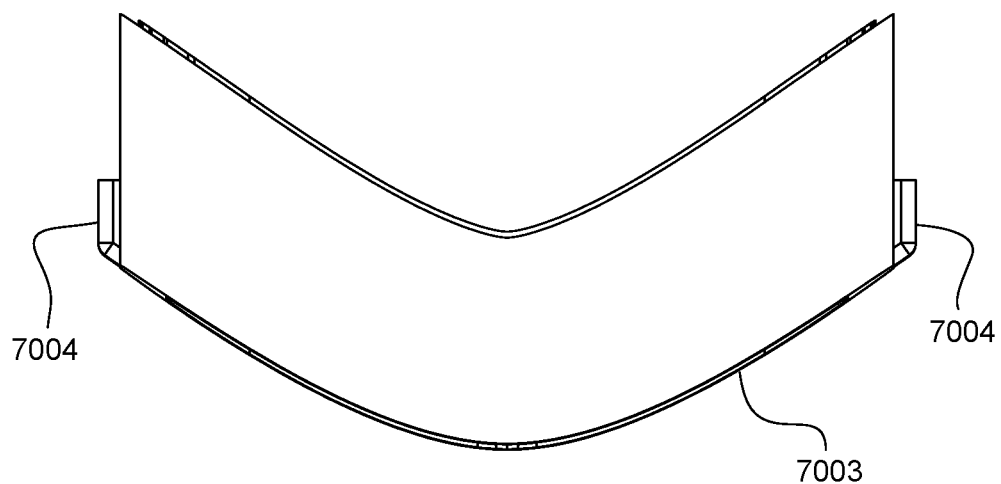

FIG. 10D shows a bottom view of the HME frame 7003 of the removable HME 7000.

Figure 10E:
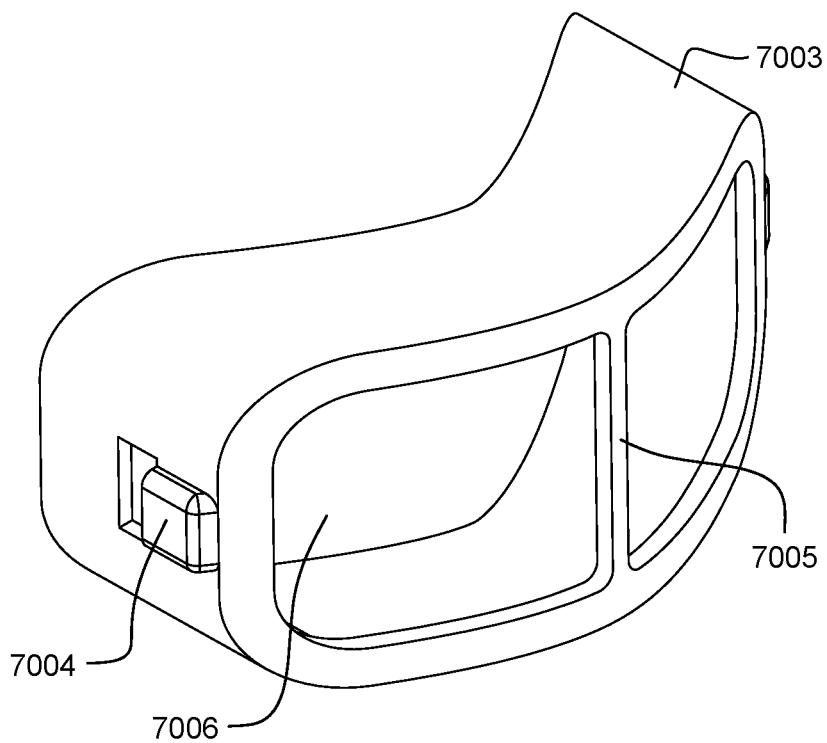

FIG. 10E shows a first perspective of the HME frame 7003 of the removable HME 7000.

Figure 10F:
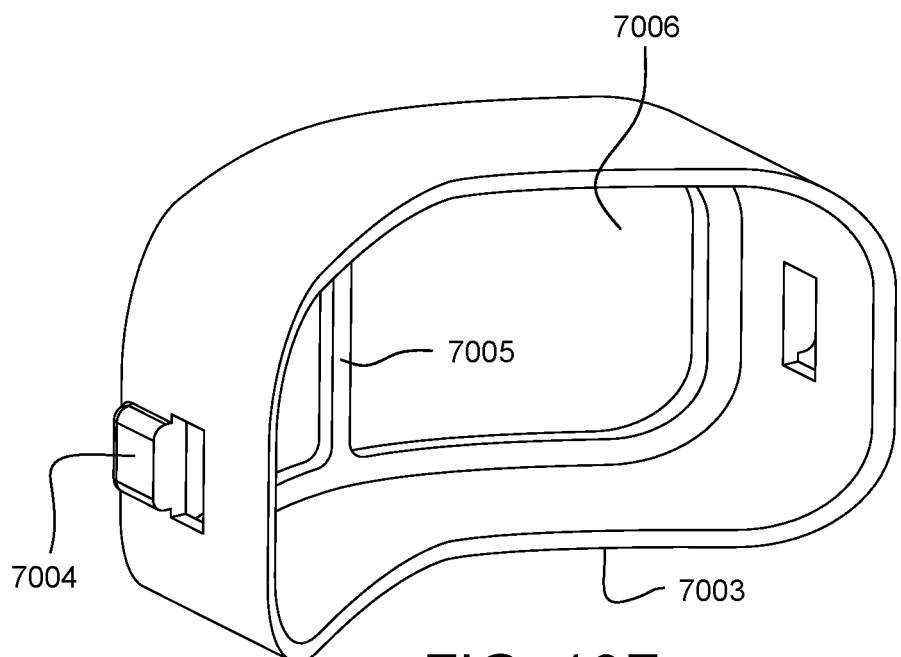

FIG. 10F shows a second perspective of the HME frame 7003 of the removable HME 7000.

Figure 11A:
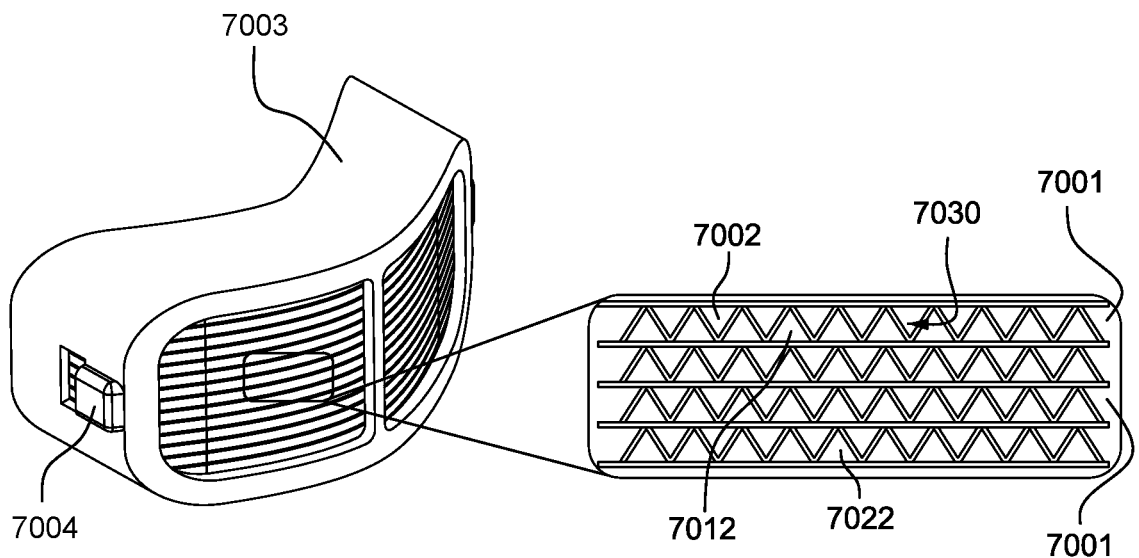

FIG. 11A shows the removable HME 7000 of the further example wherein a magnified view of the layers 7001 is shown.

Figure 11B:
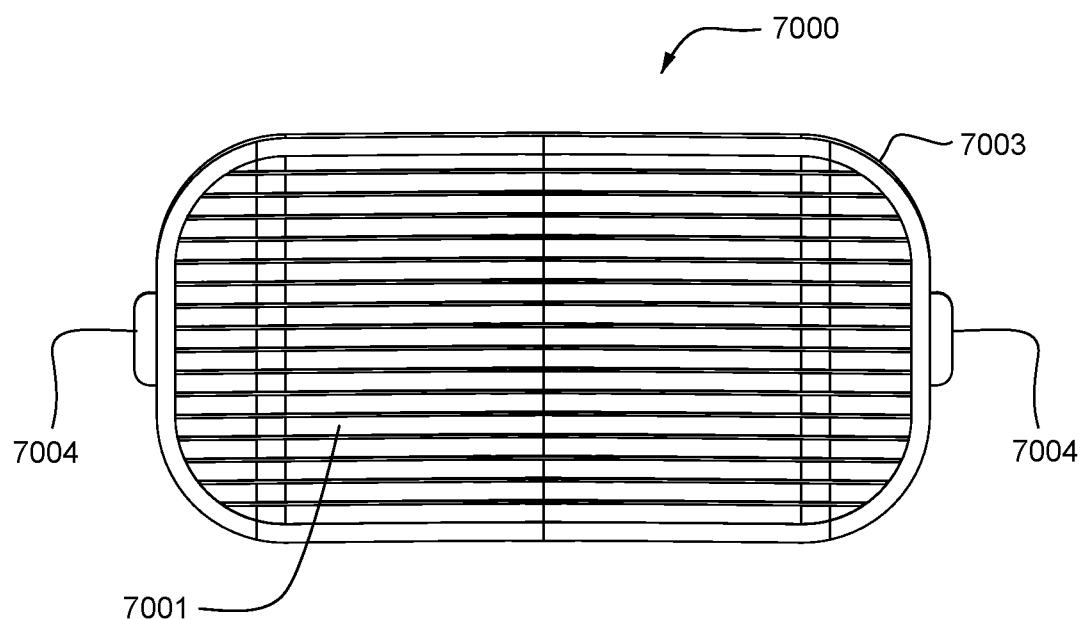

FIG. 11B shows an anterior view of the removable HME 7000.

Figure 11C:
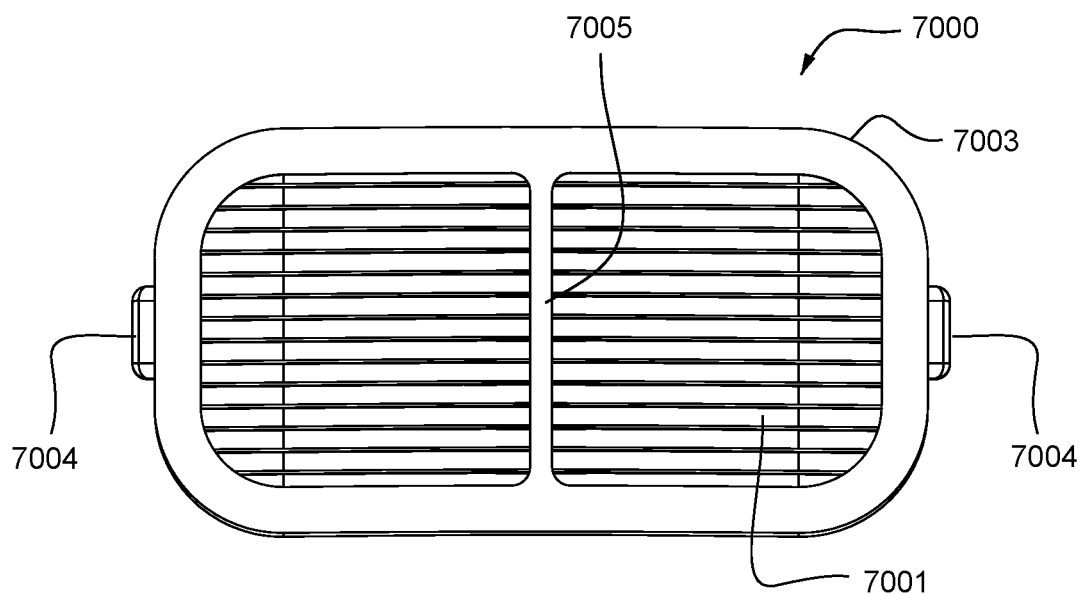

FIG. 11C shows a posterior view of the removable HME 7000.

Figure 11D:
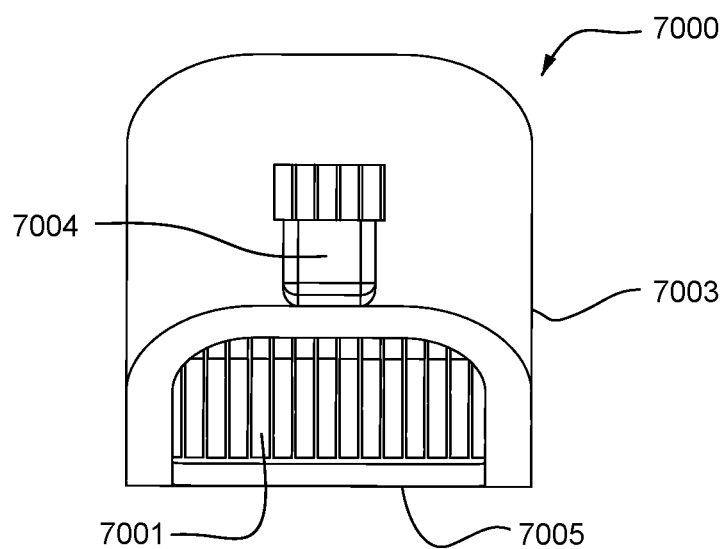

FIG. 11D shows a side view of the removable HME 7000.

Figure 11E:
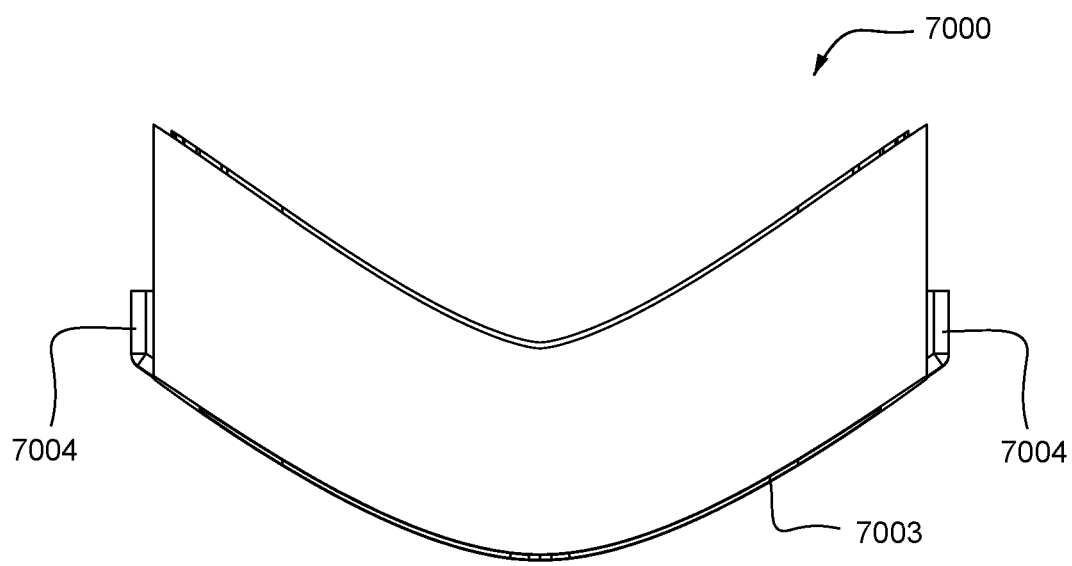

FIG. 11E shows a bottom view of the removable HME 7000.

Figure 11F:
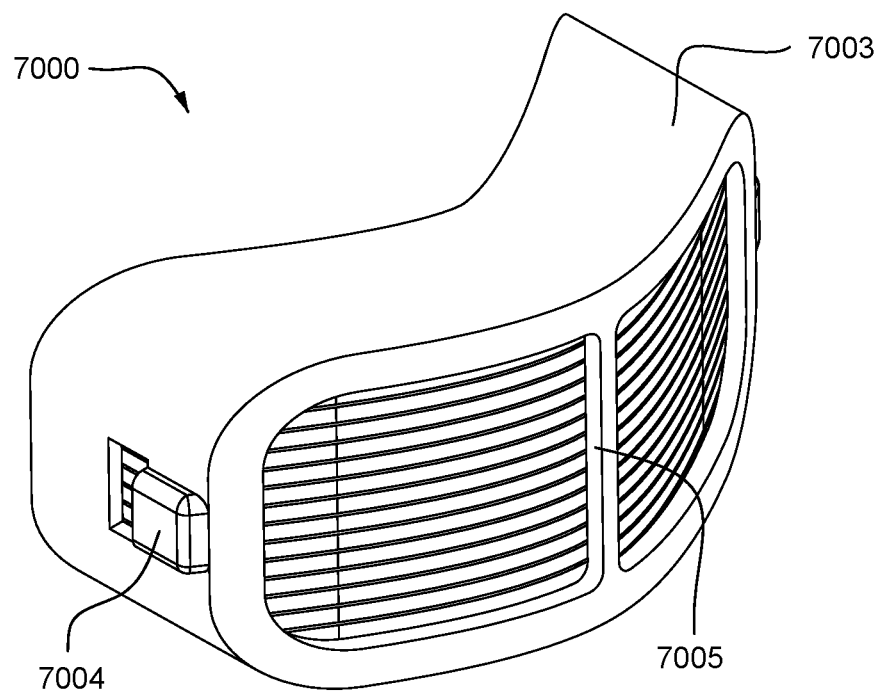

FIG. 11F shows a first perspective view of the removable HME 7000 of FIG. 71.

Figure 11G:
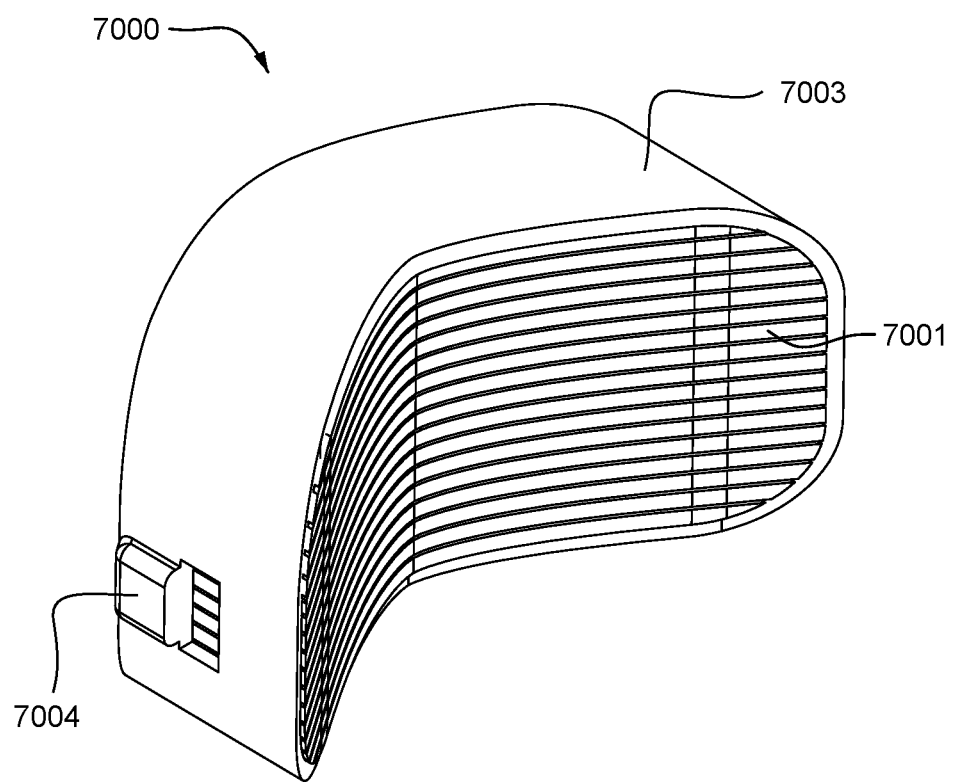

FIG. 11G shows a second perspective view of the removable HME 7000 of FIG. 71.

Figure 12A:
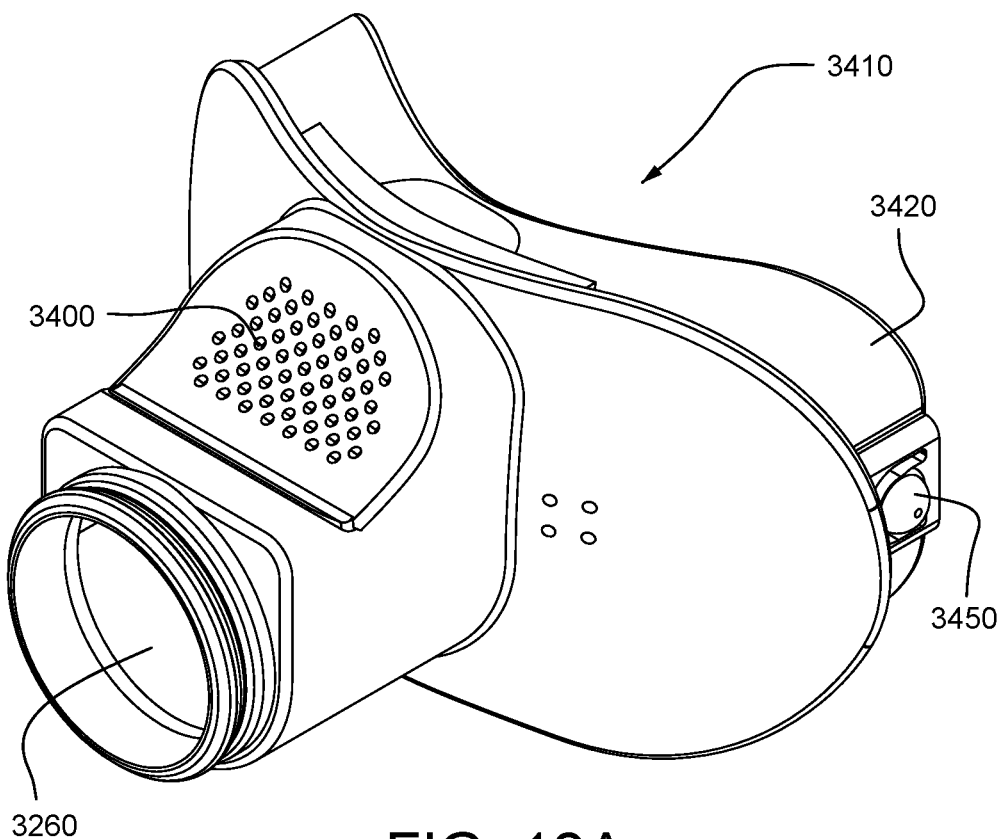

FIG. 12A shows an anterior perspective view of the HME housing portion 3410 of the patient interface 3000.

Figure 12B:
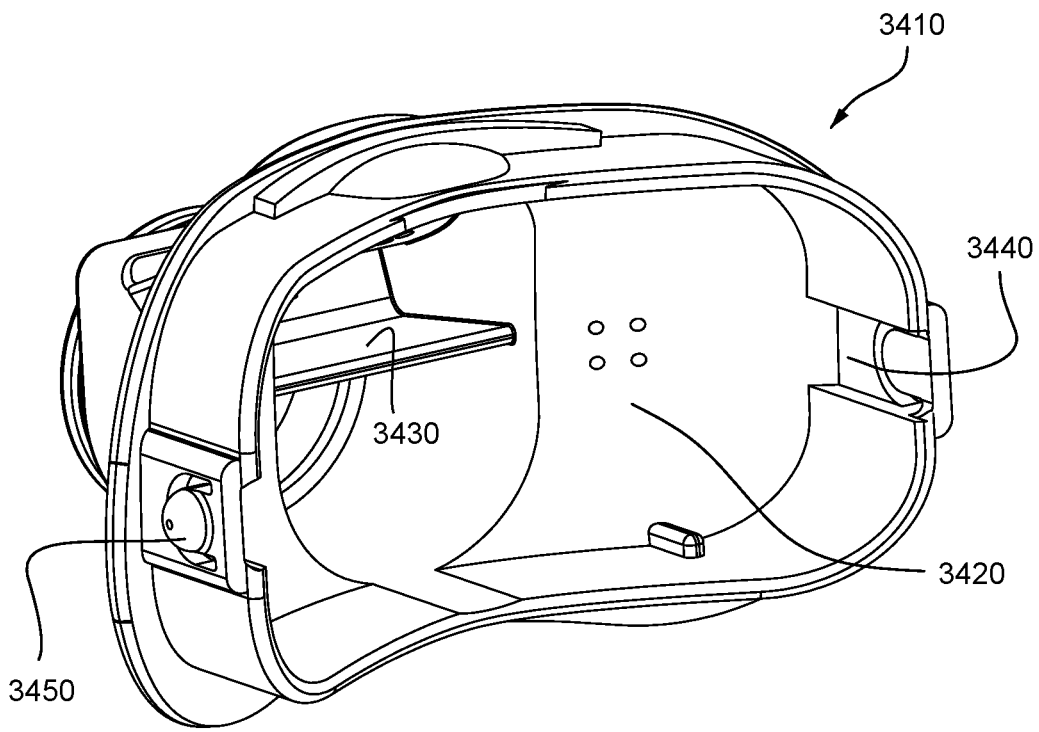

FIG. 12B shows a posterior perspective view of the HME housing portion 3410 of the patient interface 3000.

Figure 12C:
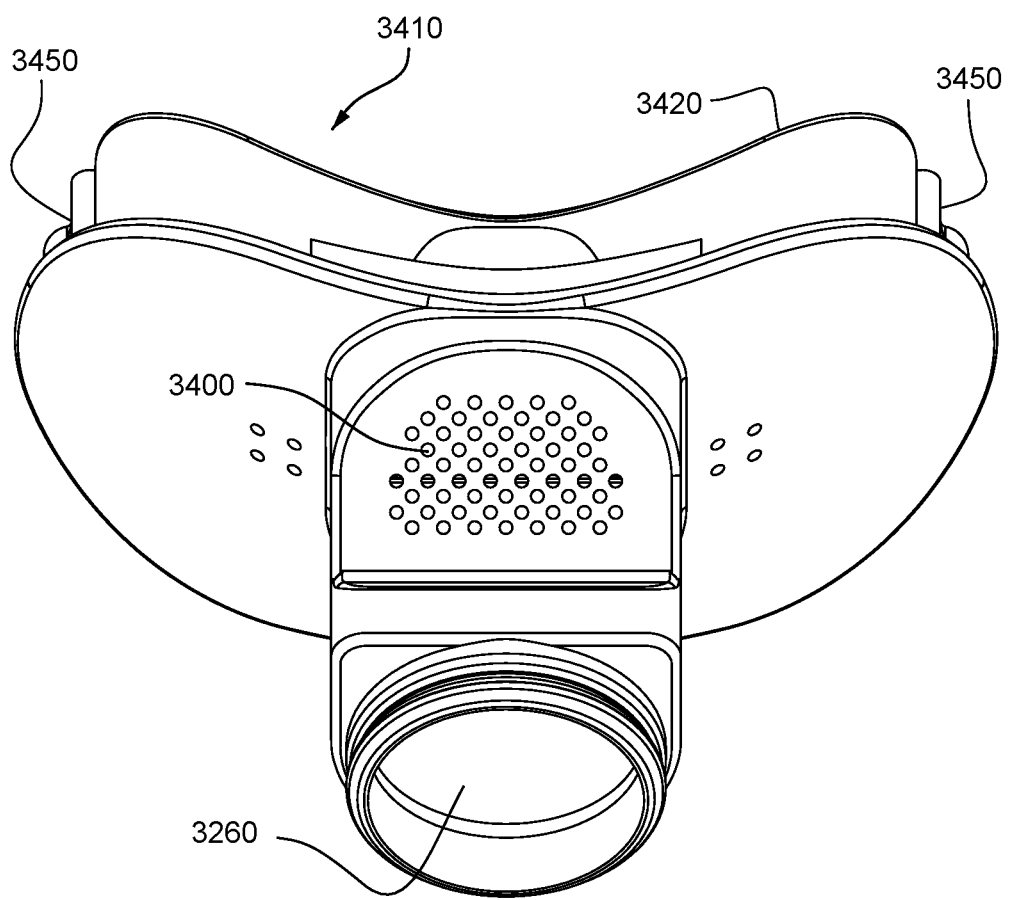

FIG. 12C shows a top perspective view of the HME housing portion 3410 of the patient interface 3000.

Figure 12D:
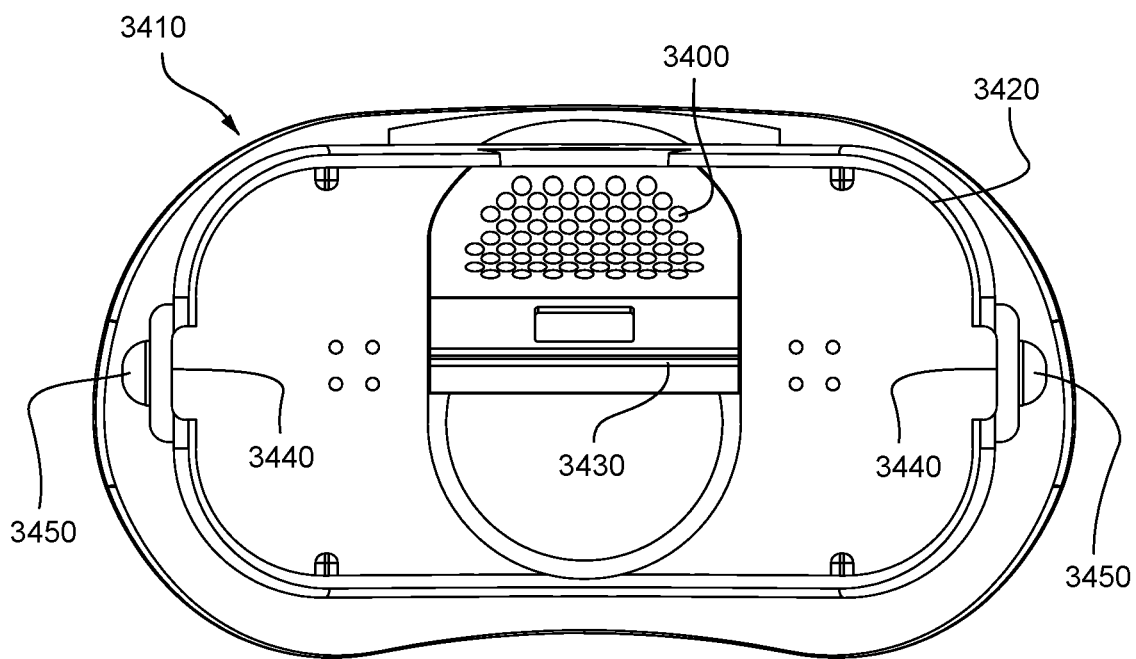

FIG. 12D shows a posterior view of the HME housing portion 3410 of the patient interface 3000.

Figure 13A:
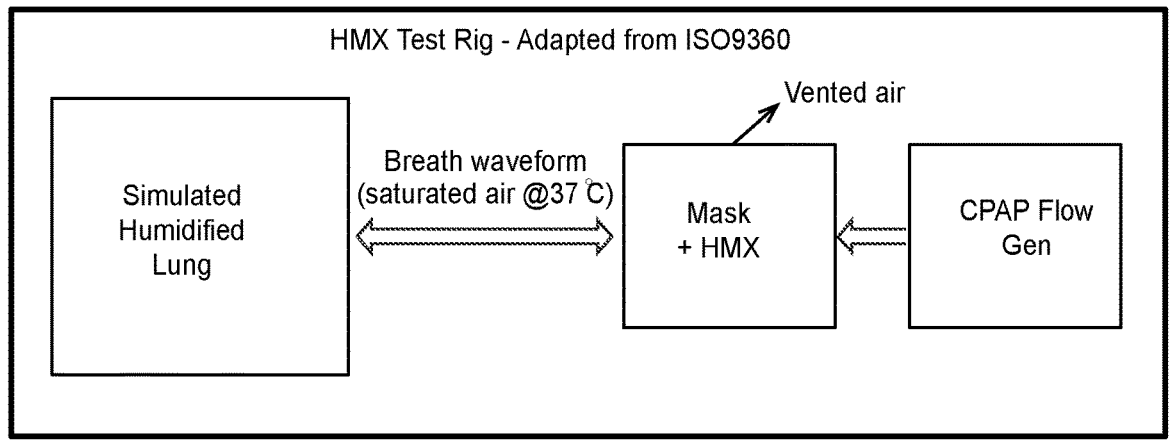

FIG. 13A shows a flow diagram of an exemplary process followed for selecting a suitable heat and moisture exchanger (HME or HMX).

Figure 13B:
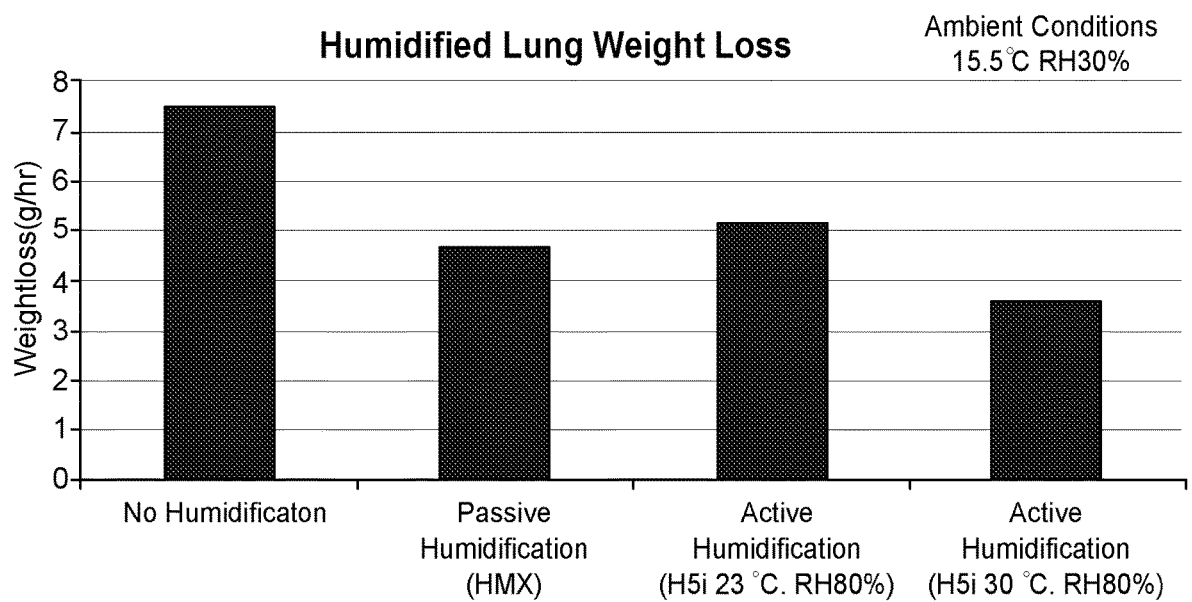

FIG. 13B shows a chart of humidified lung weight loss with various types of humidification.

FIG. 13C shows various examples of corrugations or flute configurations forming the corrugated structure that may be utilised in an HME according to examples of the present technology.

FIG. 13D shows the parameters of various exemplary corrugated structures according to examples of the present technology.

FIG. 13E shows the measurements used to provide the parameters listed in the chart of FIG. 13D.

Figure 14A:
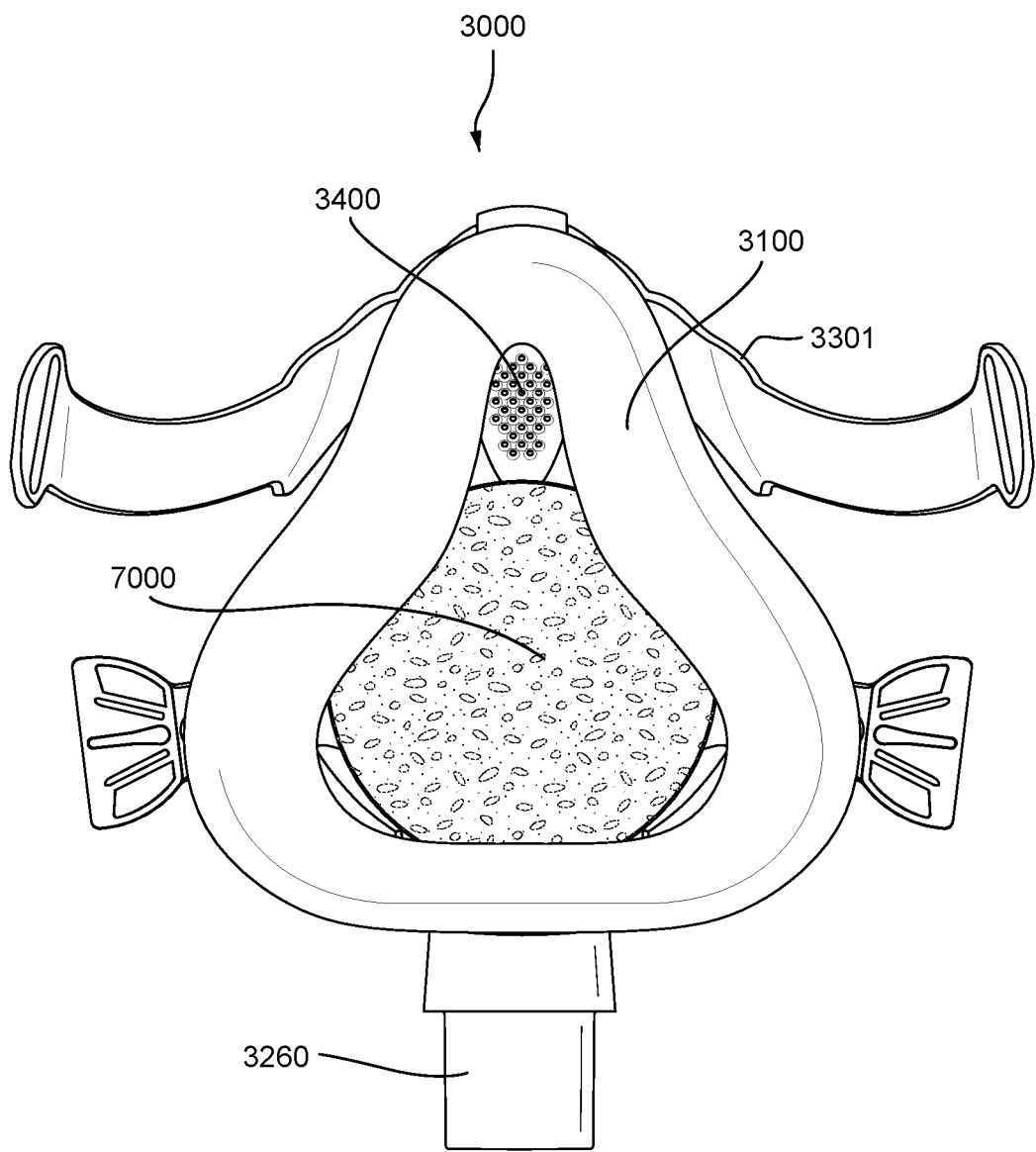

FIG. 14A shows a rear view of a patient interface with a HME according to an example of the present technology.

Figure 14B:
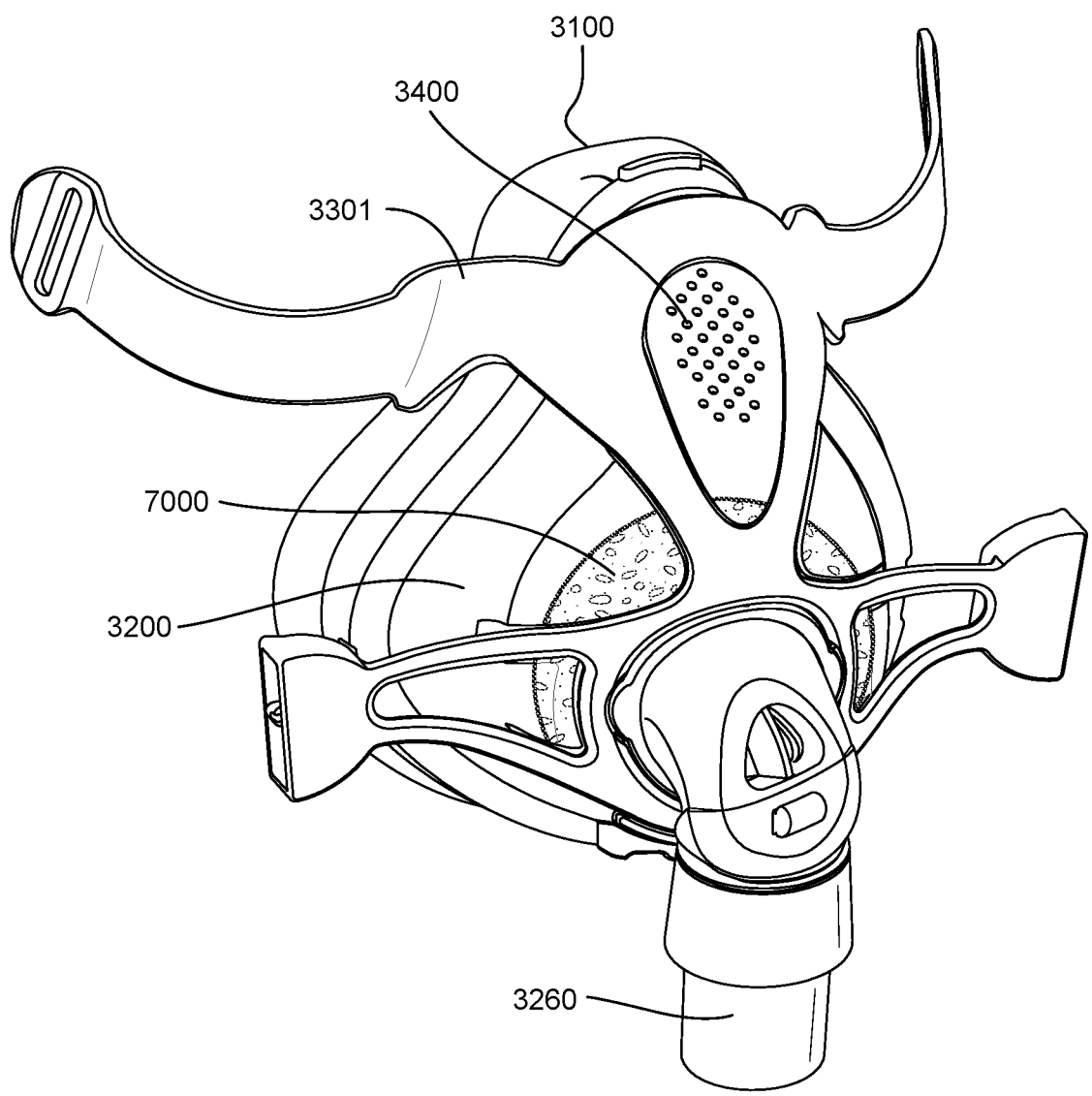

FIG. 14B shows a front perspective view of a patient interface with a HME according to an example of the present technology.

Figure 14C:
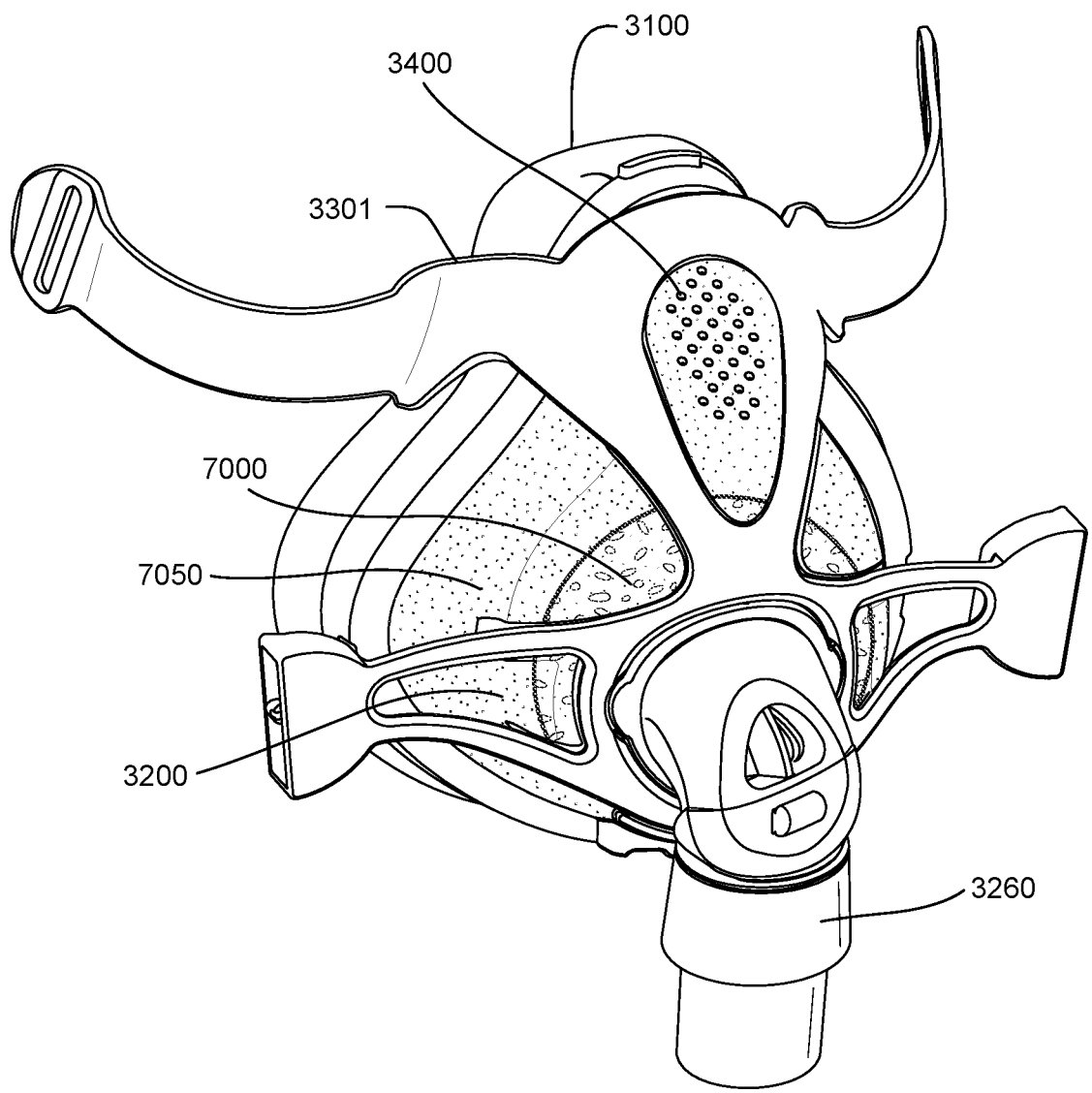

FIG. 14C shows a front perspective view of a patient interface with a HME and a supporting membrane according to an example of the present technology.

Figure 14D:
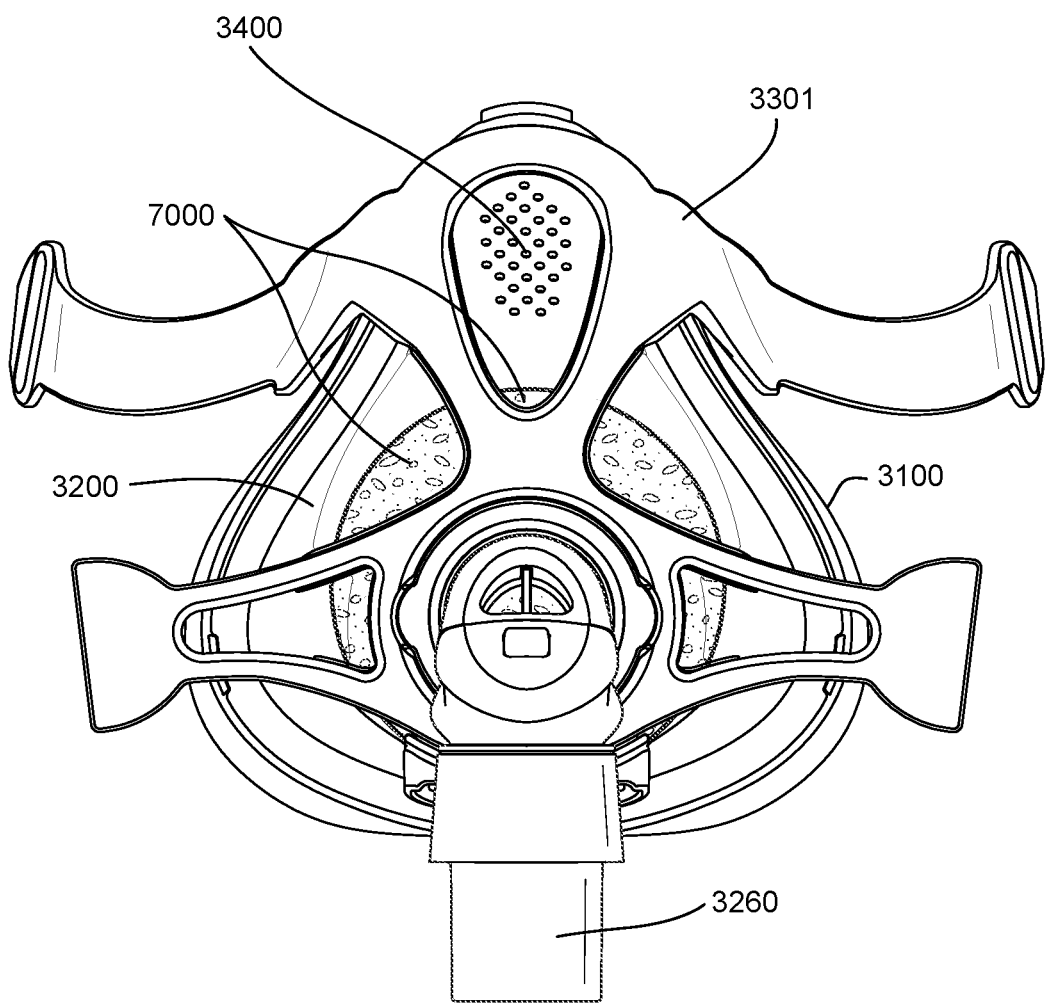

FIG. 14D shows a front view of a patient interface with a HME according to an example of the present technology.

Figure 14E:
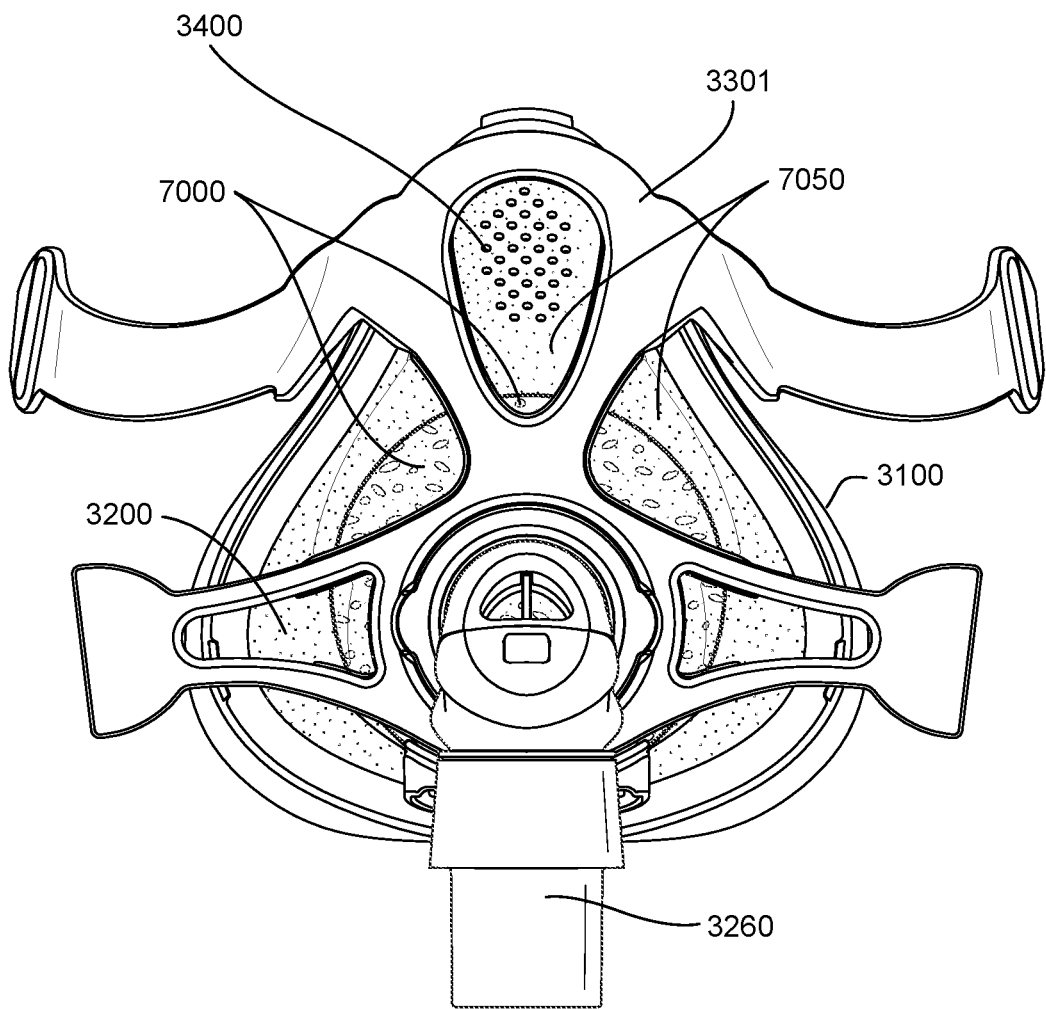

FIG. 14E shows a front view of a patient interface with a HME and a supporting membrane according to an example of the present technology.

Figure 14F:
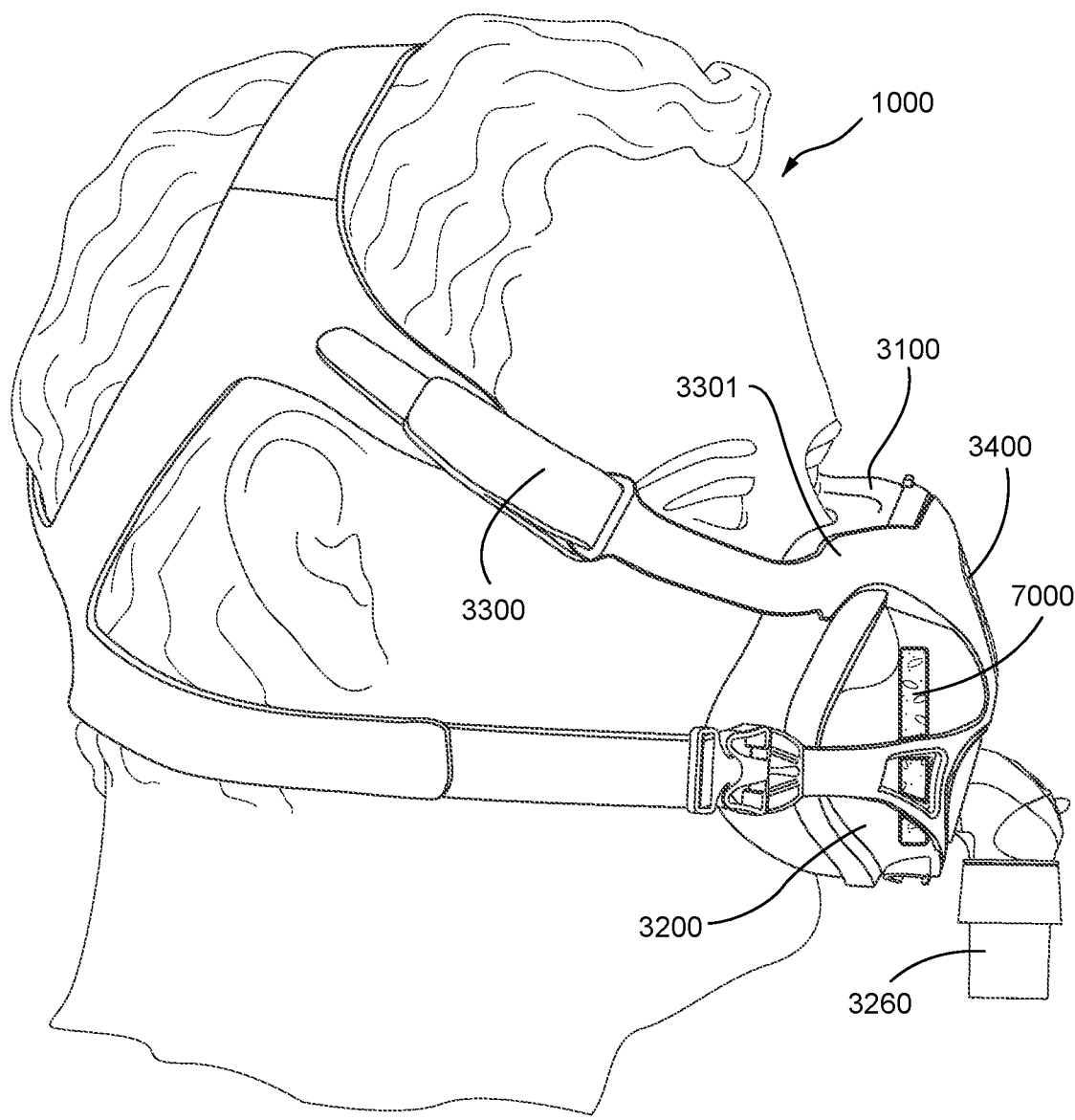

FIG. 14F shows a side view of a patient interface with a HME donned on a patient according to an example of the present technology.

Figure 15A:
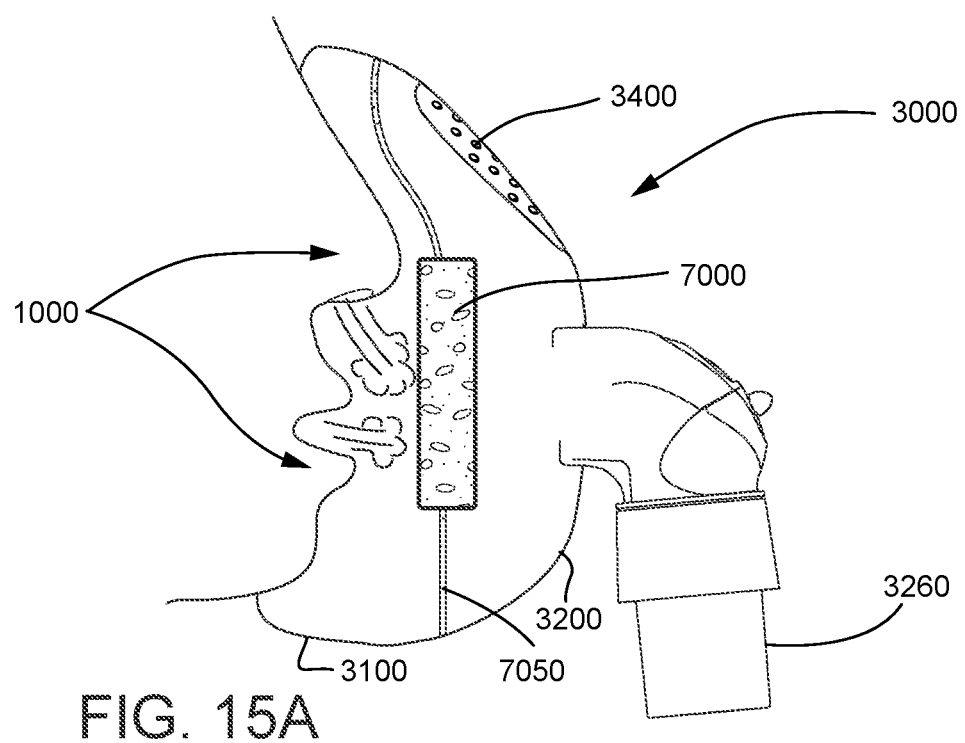

FIG. 15A shows a side view of a patient interface with a HME donned on a patient according to an example of the present technology.

Figure 15B:
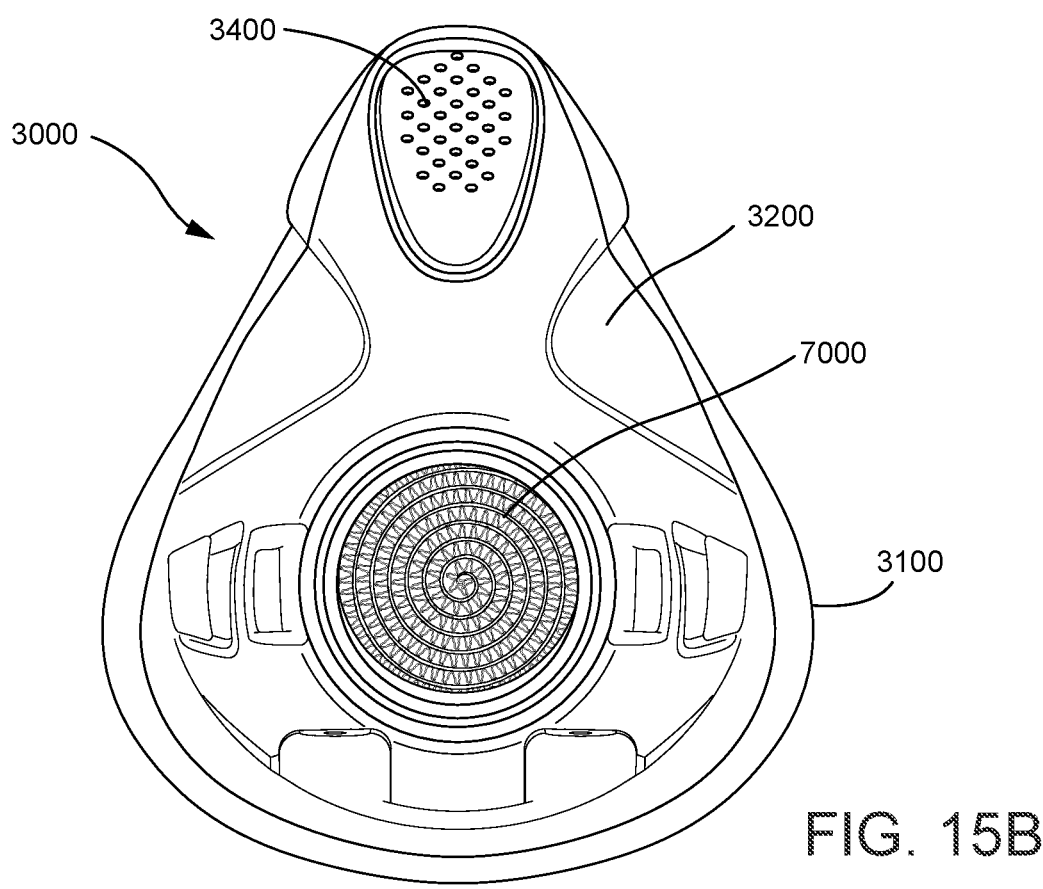

FIG. 15B shows a front view of a patient interface with a HME according to an example of the present technology.

Figure 15C:
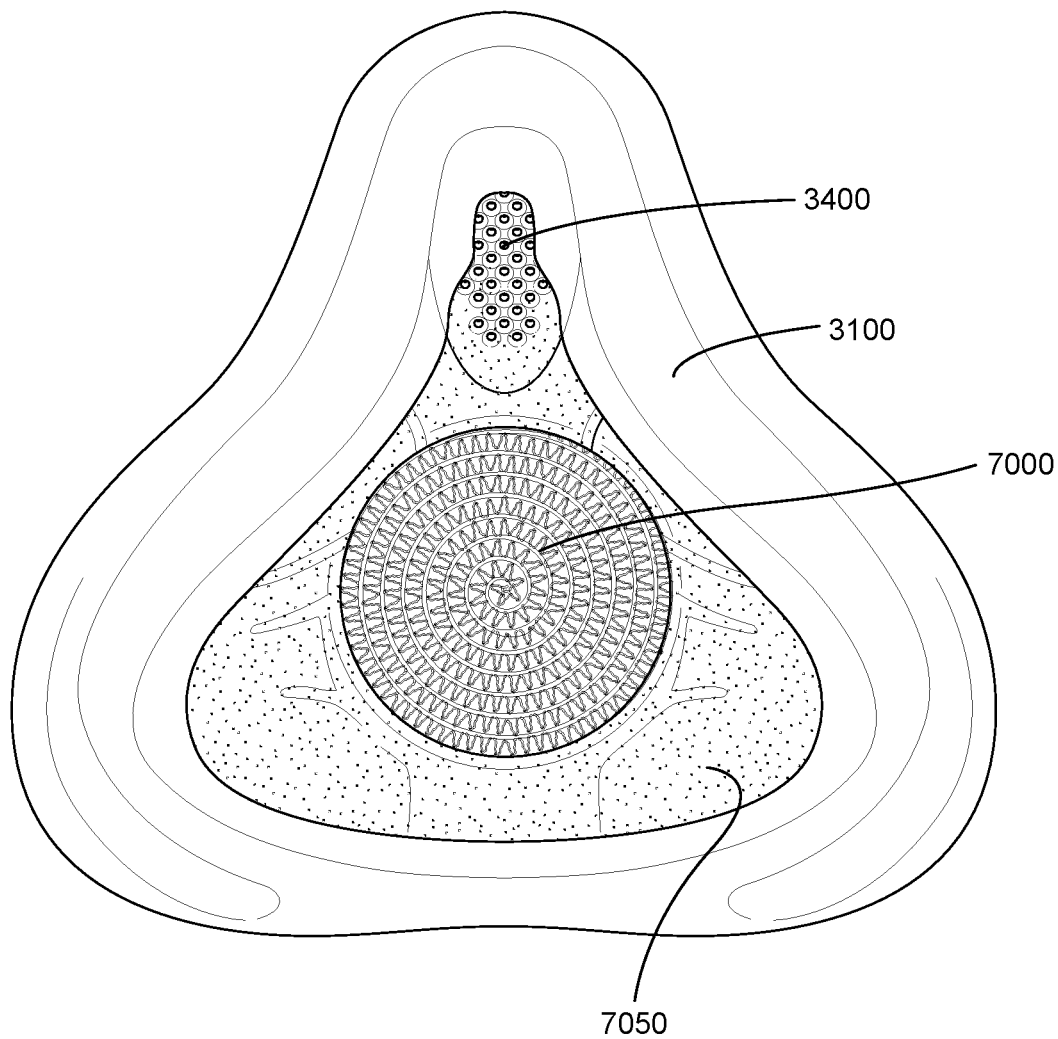

FIG. 15C shows a rear view of a patient interface with a HME and a supporting membrane according to an example of the present technology.

Figure 16:
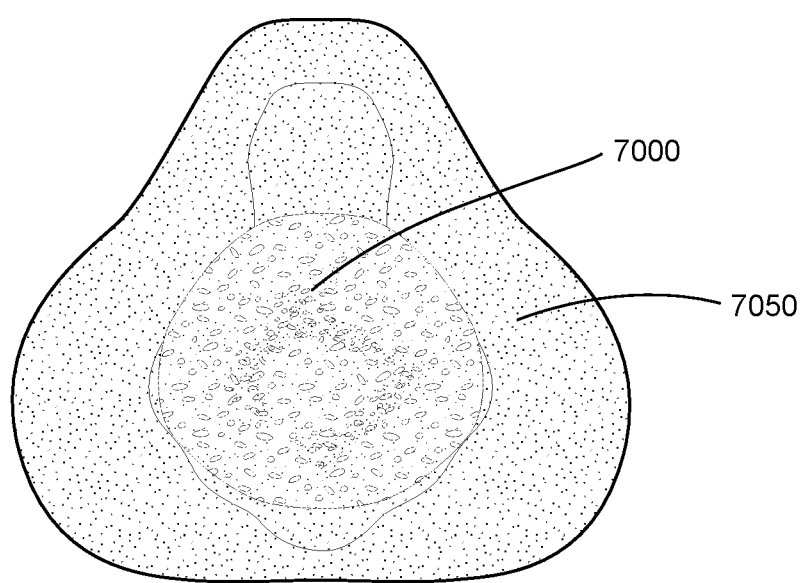

FIG. 16 shows a rear view of a HME and a supporting membrane according to an example of the present technology.

Figure 17:
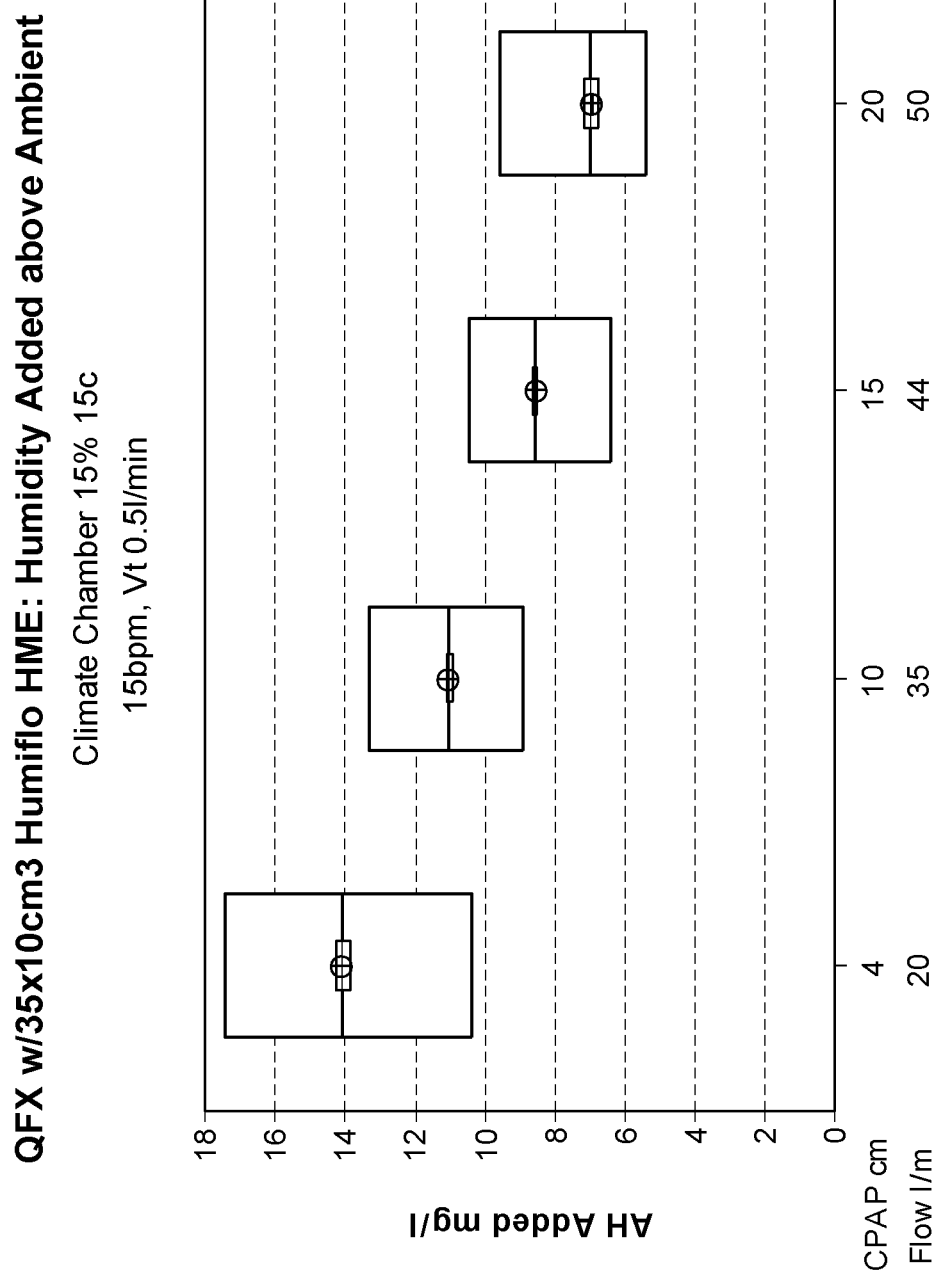

FIG. 17 a graph comparing the humidity added above ambient humidity at different therapeutic pressures and flow rates when a HME is placed in a known mask (ResMed Quattro FX).

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise a RPT device 4000 for supplying pressurised respiratory gas, such as air, to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange 3110 and a support flange 3120. The sealing flange 3110 may comprise a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge 3220 of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber

The plenum chamber 3200 may have a perimeter 3210 that is shaped to be complementary to the surface contour of the face of an average person in the region where a seal will form in use. In use, a marginal edge 3220 of the plenum chamber 3200 is positioned in close proximity to an adjacent surface of the face. Actual contact with the face is provided by the seal-forming structure 3100. The seal-forming structure 3100 extends in use about the entire perimeter 3210 of the plenum chamber 3200.

5.3.3 Positioning and Stabilising Structure

The seal-forming portion 3100 of the patient interface 3000 of the present technology is held in sealing position in use by the positioning and stabilising structure 3300.

5.3.4 Vent

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 is located in the plenum chamber 3200. Alternatively, the vent 3400 is located in a decoupling structure 3500, e.g. a swivel 3510.

5.3.5 Decoupling Structure(s)

In one form the patient interface 3000 includes at least one decoupling structure 3500, for example a swivel 3510 or a ball and socket 3520.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve 3800.

5.3.9 Ports

In one form of the present technology, a patient interface 3000 includes one or more ports, that allow access to the volume within the plenum chamber 3200. In one form this allows a clinician to supply supplemental oxygen. In one form this allows for the direct measurement of a property of gases within the plenum chamber 3200, such as the pressure.

5.4 RPT Device

A RPT device 4000 in accordance with one aspect of the present technology comprises mechanical and pneumatic components 4100, electrical components 4200 and is configured to execute one or more algorithms 4300. The RPT device may have an external housing 4010, which may be formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RT device 4000 may include a handle 4018.

The pneumatic path of the RPT device 4000 may comprise one or more air path items, e.g. an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow sensors 4274

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may include an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

A RPT device in accordance with one form of the present technology may include an air filter 4110, or a plurality of air filters 4110.

In one form, an inlet air filter 4112 is located at the beginning of the pneumatic path upstream of a pressure generator 4140. See FIG. 4B.

In one form, an outlet air filter 4114, for example an antibacterial filter, is located between an outlet of the pneumatic block 4020 and a patient interface 3000. See FIG. 4B.

5.4.1.2 Muffler(s)

In one form of the present technology, an inlet muffler 4122 is located in the pneumatic path upstream of a pressure generator 4140. See FIG. 4B.

In one form of the present technology, an outlet muffler 4124 is located in the pneumatic path between the pressure generator 4140 and a patient interface 3000. See FIG. 4B.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein in their entirety: U.S. Pat. Nos. 7,866,944; 8,638,014; 8,636,479; and PCT patent application publication number WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g. the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Transducer

A flow transducer 4274 in accordance with the present technology may be based on a differential pressure transducer, for example, an SDP600 Series differential pressure transducer from SENSIRION.

In one form, a signal representing a flow rate such as a total flow Qt from the flow transducer 4274 is received by the central controller 4230.

5.4.1.4.2 Pressure Transducer

A pressure transducer 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

5.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.4.2 RPT Device Electrical Components

5.4.2.1 Power Supply

A power supply 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, a RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.3 Central Controller

In one form of the present technology, the central controller 4230 is one or a plurality of processors suitable to control a RPT device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with a RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

The memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which are stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to remote external communication network 4282 and/or a local external communication network 4284. A remote external communication network 4282 may be connectable to remote external device 4286. A local external communication network 4284 may be connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

A local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

5.4.3.1 Pre-Processing Module

A pre-processing module 4310 in accordance with one form of the present technology receives as an input a signal from a transducer 4270, for example a flow transducer 4274 or pressure transducer 4272, and performs one or more process steps to calculate one or more output values that will be used as an input to another module, for example a therapy engine module 4320.

In one form of the present technology, the output values include the interface or mask pressure Pm, the respiratory flow Qr, and the unintentional leak flow Ql.

In various forms of the present technology, the pre-processing module 4310 comprises one or more of the following algorithms: pressure compensation 4312, vent flow 4314 (e.g. intentional leak), leak flow 4316 (e.g. unintentional leak), and respiratory flow 4318.

5.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.3.1.2 Vent Flow

In one form of the present technology, a vent flow calculation algorithm 4314 receives as an input an estimated pressure, Pm, in the patient interface 3000 and estimates a vent flow of air, Qv, from a vent 3400 in a patient interface 3000.

5.4.3.1.3 Leak Flow

In one form of the present technology, a leak flow algorithm 4316 receives as an input a total flow, Qt, and a vent flow Qv, and provides as an output an estimate of the unintentional leak, i.e. leak flow, Ql, by calculating an average of the difference between total flow Qt and vent flow Qv over a period sufficiently long to include several breathing cycles, e.g. about 10 seconds.

In one form, the leak flow algorithm 4316 receives as an input a total flow Qt, a vent flow Qv, and an estimated pressure, Pm, in the patient interface 3000, and provides as an output a leak flow Ql, by calculating a leak conductance, and determining a leak flow Ql to be a function of leak conductance and pressure, Pm. Leak conductance may be calculated as the quotient of low pass filtered non-vent flow equal to the difference between total flow Qt and vent flow Qv, and low pass filtered square root of pressure Pm, where the low pass filter time constant has a value sufficiently long to include several breathing cycles, e.g. about 10 seconds.

5.4.3.1.4 Respiratory Flow

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

5.4.3.2 Therapy Engine Module

In one form of the present technology, a therapy engine module 4320 receives as inputs one or more of a pressure, Pm, in a patient interface 3000, and a respiratory flow of air to a patient, Qr, and provides as an output, one or more therapy parameters.

In one form of the present technology, a therapy parameter is a CPAP treatment pressure Pt.

In one form of the present technology, therapy parameters are one or more of a level of pressure support, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, and therapy parameter determination 4328.

5.4.3.2.1 Phase Determination

In one form of the present technology, the RPT device 4000 does not determine phase.

In one form of the present technology, a phase determination algorithm 4321 receives as an input a signal indicative of respiratory flow, Qr, and provides as an output a phase Φ of a breathing cycle of a patient 1000.

In one form, the phase output is a discrete variable with values of either inhalation or exhalation. In one implementation of this form, the phase Φ is determined to have a discrete value of inhalation when a respiratory flow Qr has a positive value that exceeds a positive threshold, and the phase Φ is determined to have a discrete value of exhalation when a respiratory flow Qr has a value that is more negative than a negative threshold. By convention in this implementation, the phase value during inhalation may be set to 0, while the phase value during inhalation may be set to 1.

In one form, the phase output is a discrete variable with values of one of inhalation, mid-inspiratory pause, and exhalation.

In one form, the phase output is a continuous variable, for example varying from 0 to 1, or 0 to $2\pi$ radians.

5.4.3.2.2 Waveform Determination

In one form of the present technology, the therapy engine module 4320 provides an approximately constant treatment pressure throughout a respiratory cycle of a patient.

In one form of the present technology, the therapy engine module 4320 provides a treatment pressure that varies over the respiratory cycle according to a waveform of pressure vs phase.

In one form of the present technology, a waveform determination algorithm 4322 provides as an output the pressure-phase waveform P(Φ). The pressure-phase waveform P(Φ) may be valued between 0 and 1.

The predetermined waveform P(Φ) may be provided as a lookup table of values P as a function of phase values Φ. The predetermined waveform P(Φ) may alternatively be provided as one or more parameters that characterise the waveform P(Φ) according to a predetermined parametric description.

In one form, the waveform is maintained at an approximately constant level for all values of phase.

In one form, the waveform is a square wave, having a constant higher value for some values of phase, and a constant lower level for other values of phase. In this form, the returned parameter may be a threshold value of phase above which the waveform rises from the lower level to the higher level.

In one form, the waveform P(Φ) has two exponential portions, an exponential rise according to one time constant for values of phase up to a threshold, and an exponential decay for values of phase above the threshold. In this form, the returned parameters may be the two time constants and the threshold.

5.4.3.2.3 Ventilation Determination

In one form of the present technology, a ventilation determination algorithm 4323 receives an input a respiratory flow Qr, and determines a measure indicative of patient ventilation, Vent.

In one form ventilation determination algorithm 4323 determines a current value of patient ventilation, Vent, as half the low-pass filtered absolute value of respiratory flow, Qr.

5.4.3.2.4 Determination of Inspiratory Flow Limitation

In one form of the present technology, the central controller 4230 executes one or more algorithms 4324 for the detection of inspiratory flow limitation.

In one form the algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can other than those described.

5.4.3.2.5 Determination of Apneas and Hypopneas

In one form of the present technology, the central controller 4230 executes one or more algorithms 4325 for the determination of the presence of apneas and/or hypopneas.

The one or more algorithms 4325 may receive as an input a respiratory flow signal Qr and provide as an output a flag that indicates that an apnea or a hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

5.4.3.2.6 Determination of Snore

In one form of the present technology, the central controller 4230 executes one or more snore algorithms 4326 for the detection of snore.

In one form the snore algorithm 4326 receives as an input a respiratory flow signal Qr and provides as an output a metric of the extent to which snoring is present.

The algorithm 4326 may comprise the step of determining the intensity of the flow signal in the range of 30-300 Hz. Further, algorithm 4326 may comprise a step of filtering the respiratory flow signal Qr to reduce background noise, e.g. the sound of airflow in the system from the blower.

5.4.3.2.7 Determination of Airway Patency

In one form of the present technology, the central controller 4230 executes one or more algorithms 4327 for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency algorithm 4327 receives as an input a respiratory flow signal Qr, and determines the presence or absence of a cardiogenic signal. The absence of a cardiogenic signal is taken to be an indication of a closed airway.

5.4.3.2.8 Determination of Therapy Parameters

In one form of the present technology, the central controller 4230 executes one or more algorithms 4328 for the determination of one or more therapy parameters using the values returned by one or more of the other algorithms in the therapy engine module 4320.

In one form of the present technology, the therapy parameter is an instantaneous treatment pressure Pt. In one implementation of this form, the treatment pressure Pt is given by $$Pt = AP(\Phi) + P_0 \qquad (1)$$

where:

A is the pressure support,

P($\Phi$) is the pressure-phase waveform value (in the range 0 to 1) at the current value $\Phi$ of phase, and P$_0$ is a base pressure.

Various therapy modes may be defined depending on the values of the parameters A and P$_0$. In some implementations of this form of the present technology, the pressure support A is identically zero, so the treatment pressure Pt is identically equal to the base pressure P$_0$ throughout the respiratory cycle. Such implementations are generally grouped under the heading of CPAP therapy.

The base pressure P$_0$ may be a constant value that is prescribed and/or manually entered to the PAP device 4000. This alternative is sometimes referred to as constant CPAP therapy. Alternatively, the base pressure P$_0$ may be continuously computed as a function of indices or measures of one or more of sleep disordered breathing events such as flow limitation, apnea, hypopnea, patency, and snore returned by the respective algorithms in the therapy engine module 4320. This alternative is sometimes referred to as APAP therapy.

In other implementations of this form, referred to as positive-pressure ventilation, the pressure support A is non-zero. In some such implementations, in which the RPT device 4000 acts as a servo-ventilator, the therapy parameter determination algorithm 4328 takes as input the current measure Vent of ventilation and a target ventilation value Vtgt and calculates a value of pressure support A to bring the current measure Vent of ventilation towards the target value Vtgt of ventilation. In such implementations, the pressure-phase waveform P (Φ) is configured so as to attain a higher value during the inspiration portion of the respiratory cycle, and a lower value during the expiration portion of the respiratory cycle.

In such implementations, the therapy parameter determination algorithm 4328 may apply a continuous control methodology to compute the pressure support A. One such continuous control methodology is Proportional-Integral (PI) control, according to which the pressure support is computed as:

$$A = G \int (\text{Vent} - \text{Vtgt}) dt \quad (2)$$

where G is the gain of the PI control.

Other continuous control methodologies that may be applied by the therapy parameter determination algorithm 4328 include proportional (P), proportional-differential (PD), and proportional-integral-differential (PID).

Other control methodologies, referred to as discrete control methodologies, return a pressure support A that is one of a discrete set of predetermined values.

FIG. 4E is a flow chart illustrating a method 4500 carried out by the central controller 4230 as one implementation of the algorithm 4328. The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the treatment pressure Pt by a predetermined pressure increment ΔP, provided the increased treatment pressure Pt would not exceed an upper limit Pmax. In one implementation, the predetermined pressure increment ΔP and upper limit Pmax are 1 $cmH_2O$ and 20 $cmH_2O$ respectively. The method 4500 then returns to step 4520.

At step 4560, the central controller 4230 decreases the treatment pressure Pt by a decrement, provided the decreased treatment pressure Pt would not fall below a lower limit Pmin. The method 4500 then returns to step 4520. In one implementation, the decrement is proportional to the value of Pt−Pmin, so that the decrease in Pt to the lower limit Pmin in the absence of any detected events is exponential. In one implementation, the constant of proportionality is set such that the time constant τ of the exponential decrease of Pt is 60 minutes, and the lower limit Pmin is 4 $cmH_2O$. In other implementations, the time constant τ could be as low as 1 minute and as high as 300 minutes, or as low as 5 minutes and as high as 180 minutes. Alternatively, the decrement in Pt could be predetermined, so the decrease in Pt to the lower limit Pmin in the absence of any detected events is linear.

5.4.3.3 Control Module

Therapy control module 4330 in accordance with one aspect of the present technology receives as inputs the therapy parameters from the therapy engine module 4320, and controls the pressure generator 4140 to deliver a flow of gas in accordance with the therapy parameters.

In one form of the present technology, the therapy parameter is a treatment pressure Pt, and the therapy control module 4330 controls the therapy device 4245 to deliver a flow of gas whose mask pressure Pm at the patient interface 3000 is equal to the treatment pressure Pt.

5.4.3.4 Detection of Fault Conditions

In one form of the present technology, the central controller 4230 executes one or more methods for the detection of fault conditions. The fault conditions detected by the one or more methods may include at least one of the following:

Power failure (no power, or insufficient power)

Transducer fault detection

Failure to detect the presence of a component

Operating parameters outside recommended ranges (e.g. pressure, flow, temperature, $PaO_2$)

Failure of a test alarm to generate a detectable alarm signal.

Upon detection of the fault condition, the corresponding algorithm signals the presence of the fault by one or more of the following:

Initiation of an audible, visual &or kinetic (e.g. vibrating) alarm

Sending a message to an external device

Logging of the incident 5.5 Humidifier 5.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.5.2 Humidifier Mechanical Components 5.5.2.1 Water Reservoir

According to one arrangement, the humidifier 5000 may comprise a water reservoir 5110 configured to hold, or retain, a volume of liquid (e.g. water) to be used for humidification of the flow of air. The water reservoir 5110 is configured to hold a predetermined maximum volume of water in order to provide adequate humidification for at least the duration of respiratory therapy, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.5.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.5.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the reservoir dock 5130.

5.5.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.5.3 Humidifier Electrical & Thermal Components

The humidifier 5000 may comprise a number of electrical and/or thermal components such as those listed below.

5.5.3.1 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow sensor 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.5.3.1.1 Pressure Transducer

One or more pressure transducers 5212 may be provided to the humidifier 5000 in addition to, or instead of, a pressure transducer 4272 provided in the RPT device 4000.

5.5.3.1.2 Flow Transducer

One or more flow transducers 5214 may be provided to the humidifier 5000 in addition to, or instead of, a flow transducer 4274 provided in the RPT device 4000.

5.5.3.1.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.5.3.1.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.5.3.2 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication Number WO 2012/171072, the entire document of which is incorporated herewithin by reference.

In some forms, the heating element 5240 may be provided in the humidifier base 5006 where heat may be provided to the humidifier reservoir 5110 primarily by conduction as shown in FIG. 5B.

5.5.3.3 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.6 Breathing Waveforms

FIG. 6A shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Tot, is about 4 s. The person typically breathes at a rate of about 15 breaths per minute (BPM), with Ventilation, Vent, about 7.5 L/minute. A typical duty cycle, the ratio of Ti to Tot is about 40%.

FIG. 6B shows a patient during Non-REM sleep breathing normally over a period of about ninety seconds, with about 34 breaths, being treated with Automatic PAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electro-cardiogram. The seventh channel shows pulse oximetry (SpO$_2$) with repetitive desaturations to below 70% from about 90%. The eighth channel is respiratory airflow using nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

FIG. 6D shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

5.7 Heat and Moisture Exchanger (HME)

5.7.1 HME Overview

FIGS. 7A to 7D show examples of a HME according to the present technology. FIG. 7A shows a cross section of a HME 7000 comprising a corrugated structure 7002 comprising a plurality of corrugations 7030 between a substantially planar substrate top structure 7010 and a substantially planar substrate base structure 7020 to form a concertina layer 7001. The layer 7001 comprises a plurality of superior channels 7012 formed between a superior surface of the corrugated structure 7002 and the top structure 7010. In addition, the layer 7001 comprises a plurality of inferior channels 7022 between an inferior surface of the corrugated structure 7002 and the base structure 7020. The HME 7000 allows for a flow of breathable gas and expiratory gas to flow through the plurality of superior 7012 and inferior 7022 channels along a surface of the corrugated structure to exchange heat and moisture. Moisture is absorbed from the expiratory gas exhaled from a patient and retained in the material of the corrugated structure 7002. The material of the corrugations 7030, the top structure 7010, and/or the base structure 7020 may comprise paper or a paper based material that is able to absorb water and/or heat. The material of the corrugations 7030, the top structure 7010, and/or the base structure 7020 may be porous, water-permeable, and/or air-permeable. The retained moisture may subsequently be redelivered to the patient by humidifying a flow of breathable gas delivered to the patient's airways. In other words, the flow of breathable gas delivered to the patient's airways may absorb moisture from the HME 7000. FIG. 7B depicts the various dimensions of a HME according to these examples. A thickness of the top structure 7010 and/or the base structure 7020 may be between 0.03-0.12 mm.

The plurality of corrugations 7030 increase the surface area of the corrugated structure 7002 that allows for an increase in active surface area for the exchange of heat and moisture occurring between the corrugated structure 7002 and the surrounding volume provided by the plurality of superior 7012 and inferior 7022 channels. The top structure 7010 and the base structure 7020 may also be formed from the same heat and moisture exchanging material as the corrugated structure 7030. Alternatively, the top structure 7010 and/or the base structure 7020 may be formed of a rigid or semi-rigid material that does not absorb moisture to support the corrugated structure 7002.

The humidification performance of the HME 7000 is dependent on the effective surface area of the HME 7000 provided in a fixed volume of space. The effective surface area is the surface area of the HME 7000 that is exposed to the flow of breathable gas flowing along the surface of the HME where heat and moisture exchange occurs. The surface area per unit volume of the HME 7000 can be adjusted by providing corrugations 7030 within the heat and moisture exchange portion of the HME 7000. Furthermore, the surface area per unit volume may also be adjusted by modifying at least one of the fin thickness, pitch or height of the corrugations or flutes, which have an impact on the surface area per unit volume of the HME 7000.

The HME 7000 may comprise a plurality of layers 7001 stacked along a vertical axis of the HME 7000, as shown in FIG. 7C. The layers 7001 may be vertically stacked such that the base structure 7020 is stacked on top of the corrugated structure 7002 of an underlying adjacent layer 7001. There may be also several layers 7001 of HME stacked in the horizontal direction. Having a number of layers 7001 comprising corrugated structures 7002 that are stacked along a vertical axis of the HME 7000 further increases the surface area per unit volume of the HME. This increased surface area within a predefined volume allows for increased efficiency in heat and moisture exchange of the HME 7000. Furthermore, the layers 7001 may be compressed under a preload, as depicted in FIG. 7D, to increase the number of layers within a fixed volume to increase the surface area per unit volume. The preload is calculated by the formula:

$$P = 1 - \left(\frac{h_{final}}{h_{start}}\right)$$

where P is the Preload and $h_{start}$ is the corrugation or flute height prior to compression and wherein $h_{final}$ is the height of the corrugation post-compression.

Alternatively, the final three-dimensional shape of the HME 7000 may be formed by combining layers 7001 of different sizes and shapes to produce a HME 7000 of irregular shape adapted to fit within a plenum chamber 3200 of the patient interface 3000. The layers 7001 may be laser cut to form the desired shape and size.

As shown in FIG. 8A to 8D, displaying an alternative example, the HME 7000 may be rolled from a single strip layer 7001 comprising a corrugated structure 7002 extending from the surface of the base structure 7020 to form a plurality of corrugations 7030. The single strip layer 7001 may be rolled such that the upper folded portion 7031 of the corrugations 7030 engages the inferior surface of the base structure 7020. This configuration ensures that the plurality of channels 7012 is maintained between each roll of the single strip layer 7001. The HME 7000 may be positioned within a plenum chamber 3200 of the patient interface 3000.

FIGS. 9A to 9J, illustrate another example of the technology. The patient interface 3000 in this example has a removably engageable cushion assembly 3130 comprising a plurality of cushion assembly engagement members 3135 in the form of a clip comprising a resilient flange that removably engages to a mask frame 3250. The mask frame 3250 comprises a mask frame engagement member 3255 in the form of a recess or hole that allows for the resilient flange of the cushion assembly engagement member 3135 to pass and removably engage thereto. Alternatively, the cushion assembly 3130 may engage to the mask frame by other methods such as hook, adhesive, interference or frictional engagement. The cushion assembly 3130 comprises a seal forming structure 3100. The seal forming structure 3100 may form a seal with the entrance of a patient's airways. In addition, the seal-forming structure 3100 of the patient interface 3000 may comprise a pair of nasal puffs, or nasal pillows, each nasal puff or nasal pillow being constructed and arranged to form a seal with a respective naris of the nose of a patient. Alternatively, the seal forming structure may form a seal with the nares and the mouth.

The exemplary patient interface 3000 further comprises a removable HME 7000 that removably engages with the patient interface 3000 and the HME 7000 may be located within a HME housing portion 3420 of a vent adaptor 3410. The HME 7000 may comprise at least one HME engagement member 7004 positioned on the HME frame 7003. The at least one HME engagement member 7004 may comprise a clip and each of which may removably engage a corresponding vent adaptor engagement member 3415. The vent adaptor 3410 may comprise a vent 3400 and a mask inlet 3260 positioned on its anterior side. The vent adaptor 3410 may be adapted to removably engage to the remainder of the patient interface 3000 and locate the removably engageable HME 7000 within its HME housing portion 3420. The vent adaptor 3410 may locate the HME 7000 in a flow path of breathable gas within a plenum chamber 3200 of the patient interface 3000 and may orient the plurality of channels 7012 and 7022 of the HME to be substantially in line with or parallel to a flow path of the flow of breathable gas, thereby allowing flow through the HME via the channels 7012 and 7022. The positioning of the HME 7000 in close proximity to the entrance of the patient's airways may maximise the capture and retention of humidity that is provided to the material of the HME 7000 during exhalation. Moreover, the orientation of the channels 7012, 7022 may also allow the flow of humidified gas exhaled from the patient to flow through the channels 7012 and 7022 of the HME in the opposing direction.

The vent adaptor 3410, shown in FIGS. 12A to 12D, may locate the HME 7000 within the plenum chamber 3200 and may divide said plenum chamber 3200 into an anterior plenum chamber 3240 and a posterior plenum chamber 3230. This positioning of the HME 7000 may position the vent 3400 and inlet 3260 on an anterior side of the HME 7000 as part of the anterior plenum chamber 3240 with the entrance of the patient's airways on a posterior side of the HME 7000, adjacent to the posterior plenum chamber 3230. This configuration may allow the flow of exhaled gas from the patient to flow into the posterior plenum chamber 3240 prior to venting, which allows any humidity to be retained in the HME 7000 prior to losses out of the vent 3400. Furthermore, the configuration also may allow the flow of breathable gas to flow through the HME 7000 prior to redelivery of the captured humidity to the patient. Thus, the housing portion 3410 may provide a configuration for redelivering humidified air to a patient via a HME 7000 positioned in the flow path of the patient interface 3000.

The vent adaptor 3410 may also include receiving portions 3440 to receive respective engagement members 7004 of the HME frame 7003. The receiving portions 3440 may releasably join with the engagement members 7004 in a snap-fit. The vent adaptor 3410 may also include attachment members 3450 to releasably join the vent adaptor 3410 to the mask frame 3250. The attachment members 3450 may attach the vent adaptor 3410 to the mask frame with snap-fit.

It is also possible to position an auxiliary vent 3401 on the posterior side of the HME in the posterior plenum chamber 3240 to offset $CO_2$ build up within this volume. For example, in the case of a full face mask, the additional volume in the posterior plenum chamber 3240 (i.e., dead space volume) in comparison to smaller masks, may lead to unwanted and/or excessive $CO_2$ build up occurring within this space. To mitigate this effect, it is possible to position an auxiliary vent 3401 proximal to the patient's airways, on the posterior or patient side of the HME 7000. Positioning an auxiliary vent 3401 on the posterior side of the HME 7000 will result in some venting of the humidified flow of breathable gases prior to delivery to the patient. To compensate for this venting of humidified air, the overall humidification performance may be maintained by increasing the ability of the HME 7000 to humidify the flow of breathable gas within a predetermined volume of the plenum chamber 3400.

The vent adaptor 3410 may also include a baffle 3430 to separate the incoming flow of breathable gas from the flow of $CO_2$ washout. The baffle 3430 may separate these flows of gas from one another such that these flows of gas do not interfere with one another. U.S. Pat. No. 7,934,501, which is incorporated herein by reference in its entirety, describes further examples and features of baffles that may be applicable to the exemplary patient interface 3000.

FIGS. 10 to 10F depict examples of the HME frame 7003 according to the present technology. The HME frame 7003 may include one or more engagement member 7004. The engagement members 7004 may be releasably engage with the vent adaptor 3410. Alternatively, the engagement members 7004 may also allow the HME frame 7003 to be direct and releasably engaged with the plenum chamber 3200 of the patient interface 3000 or the mask frame 3250. The HME frame may include one or more frame apertures 7006 to allow the flow of breathable gas and/or the flow of exhaled gas to pass through the frame apertures 7006 and through the HME layers 7001. The HME frame 7003 may also include one or more HME retention members 7005. The HME retention members 7005 may be hold the HME layers 7001 in place and the HME retention members 7005 may also provide structural support for the HME frame 7003. The HME retention members 7005 may be provided to the front and/or the rear of the HME frame 7003. In the front and rear views shown in FIGS. 10A and 10B, respectively, the HME frame 7003 has a generally rectangular shape. It should be understood that the HME frame 7003 have other shapes as well to provide for the most effective utilization of space within the patient interface 3000. For example, the HME frame 7003 may have a square, oval, circular, triangular, or other polygonal shape. Accordingly, the HME layers 7001 may be shaped to conform to the interior shape of the HME frame 7003 depending on the shape of the HME frame 7003. FIG. 10D shows a top view of the HME frame 7003 and in this view it can be seen that the HME frame 7003 according to this example of the present technology is swept backwards at its lateral ends to account for the shape of the patient interface 3000. It should be understood that the HME frame 7003 may also have profile that is flat from this view as well, or swept forwards, depending on the shape of the patient interface 3000.

As is illustrated in FIGS. 1A to 11G, the HME 7000 may be stacked in layers 7001 and further comprise a rigid supporting HME frame 7003. The HME layers 7001 may be retained within the HME frame 7003 by one or more HME retaining members 7005. The HME frame 7003 may comprise a frame aperture 7006 that is aligned with the plurality of channels 7012 and 7022 that are defined by corrugations 7030 and run through the layers 7001 of the HME 7000. The frame aperture 7006 allows the flow of gas to flow through the HME in both directions, which allows the exchange of heat and moisture to be retained and redelivered to the patient. The inwardly curved predetermined three-dimensional shape of the HME frame 7003 is adapted to fit within the plenum chamber 3200 of the patient interface 3000 and avoid contact with the patient's face when the patient interface 3000 is positioned on the face. Other predetermined three-dimensional shapes may be provided to avoid contact with the patient's face while maintaining the ability of the HME 7000 fit within the plenum chamber 3200 of the patient interface 3000.

FIG. 13A shows a flow diagram of an exemplary process that may be followed for selecting a suitable heat and moisture exchanger (HME or HMX). The exemplary process may be used to test whether the HME is able to attain desired parameters in relation to humidification performance. The process is adapted from ISO9360. The process involves simulating a humidified lung and placing said lung in fluid communication with a patient interface under various testing conditions. The testing conditions may include:
 i) No humidification
 ii) Passive humidification using an in mask HME. A corrugated HME comprising a plurality of layers was used comprising a corrugated structure of F-Flute as shown in FIG. 13C with the properties listed in FIG. 13D under 'Tested HME (Flute F)'.
 iii) Active humidification using a powered humidifier H5i at 23° C., RH80%
 iv) Active humidification using a powered humidifier H5i at 30° C., RH80%

As shown in the exemplary results displayed in FIG. 13B, humidified lung weight loss was used as an indicator for simulating humidity lost in a patient's lungs under RPT therapy. As expected, no humidification i) showed the highest weight loss, simulating humidity lost by a patient under RPT therapy without any added humidification. This may ultimately lead to breathing discomfort. Passive humidification performed better than active humidification by a H5i at 23° C., RH80%. Passive humidification was also close in performance to extreme humidification using a powered humidifier H5i at 30° C., RH80%. Testing was conducted under ambient conditions of 15.5° C., RH30%. The HME used for testing was under a preload of 6% with a surface area per unit volume of 5.4 $m^2/m^3$ as per the properties listed in FIG. 13D under 'Tested HME (Flute F)'.

FIG. 13C illustrates various corrugation or flute configurations forming the corrugated structure comprised in the HME that are under no preload. The F-Flute may be used to form the corrugated structure comprising a plurality of corrugated layers of the HME. In a non-preloaded and assembled configuration, the corrugated structure may be formed of corrugated paper with a height of 0.9 mm and a paper grade of 65 gsm.

FIG. 13D shows the parameters of various corrugated structures according to examples of the present technology. The 'Tested HME' comprising a plurality of layers in an Flute F configuration was under a preload of 6%. This configuration provided a HME with a total volume of 8360 $mm^3$ and a total surface area per unit volume of 5.42 $m^2/m^3$. The total flow impedance was found to be 0.47 $cmH_2O$. The HME under optimal conditions may comprise 26 layers stacked under 32% preload to give a total volume of 4560 $mm^3$ and a surface area per unit volume of 7.5 $m^2/m^3$. The HME has a flow impedance of 1.6 $cmH_2O$, which may provide a smaller HME with improved humidification performance within an acceptable impedance range. FIG. 13E illustrates the dimensions measured to provide the parameters listed in FIG. 13D. The corrugation perimeter is the length of paper material that forms a single corrugation or flute. As listed in FIG. 13D, this length is maintained between the tested HME and the optimal HME as the preload is increased to compress the corrugation into a smaller volume. The compressive force under preload is applied to the folded portion of the corrugation to reduce the flute height while maintaining the flute pitch. The stack represents the plurality of layers vertically stacked into the illustrated three-dimensional shape, wherein the stack height is reduced as the preload is increased, thereby increasing the surface area per unit volume of the HME.

Examples of the technology are directed towards an HME 7000 positioned within the functional dead space of various full face patient interfaces 3000 (see FIG. 14A to FIG. 14F, FIG. 15A to FIG. 15, and FIG. 16). The HME 7000 may be positioned in the plenum chamber 3200 such that it remains between the patient's 1000 airways and the mask vent 3400/inlet 3260 of the patient interface 3000. The HME 7000 may be supported and held in position by a supporting membrane 7050 that may be connected to the inside walls of the plenum chamber 3200. The HME 7000 in these examples is circular in form and has a thickness of approximately 5-10 mm. Alternatively, the HME material is moulded into a profiled shape which directly assembles to the interior profile of the plenum chamber 3200, wherein the HME make take on a shape complementary to the interior of the plenum chamber 3200. In this case the shape may be a three dimensional surface with a thickness of approximately 1-10 mm.

In an example of a non-invasive patient interface 3000 in accordance with one aspect of the present technology, the patient interface 3000 may comprises the following functional aspects: a seal-forming structure 3100, a plenum chamber 3200, a HME 6000 positioned in the functional dead space within the plenum chamber 3200, a supporting membrane 7050 structure to hold the HME 7000 in position, a positioning and stabilising structure 3300 and a connection port or inlet 3260 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

A positioning and stabilising structure 3300 may also be provided to releasably secure the patient interface 3000 to the patient 1000. The positioning and stabilising structure 3300 may include a plurality of straps that are adjustable in length to allow the patient interface to be comfortably and securely fitted to the patient 1000 such that a pneumatic seal is formed around the patient's airways by the seal-forming structure 3100. A strap connector 3301 may also be provided to releasably secure the straps of the positioning and stabilising structure 3300 to the patient interface 3000. The straps of the positioning and stabilising structure 3300 may include hook and loop material for length adjustment and to allow the straps of the positioning and stabilising structure 3300 to be attached to and detached from the strap connector 3301. It should be understood that the strap connector 3301 may be releasably attached to the patient interface 3000 or it may be integrally formed therewith.

The positioning of the HME 7000 within the patient interface may be altered to adjust the hygroscopic performance. For example the distance between the HME and the airways of a patient 1000 may be adjusted. Moreover, the distance between the HME 7000 and the vent 3400 and/or inlet 3260 may also be adjusted. Adjusting the positioning of the HME 7000 may alter the hygroscopic performance of the HME by adjusting the position of the HME 7000 relative to the patient's 1000 airways. That is, the closer the HME 7000 is positioned to the patient's 1000 airways the closer it is to the source of humidity during exhalation and to the target of humidification during inhalation. However, the HME 7000 may be positioned such that it avoids contact with the patient's face. Similarly, adjusting the position of the HME 7000 may also impact impedance on flow due to the positioning relative to the inlet 3260 and the effect on $CO_2$ washout, impacted by relative position the vent 3400. By positioning the HME 7000 in the functional dead space of the patient interface 3000, the HME may occupy a larger volume compared to the volume the HME 7000 would occupy inside an air delivery conduit or elbow. This in turn may allow for more flexibility to position the HME 7000 in a larger volume to minimise impedance on therapy flow and $CO_2$ washout, while allowing for the maximisation of hygroscopic performance. While all the above benefits also apply to a moulded HME insert, the HME insert concept may provide greater design control and may reduce the trade-off between contradictory functions. Similarly, the thickness and area of the HME 7000 may also be varied to adjust these properties. For example, a HME 7000 with an increased surface area can have an increased hygroscopic performance. Moreover, a HME 7000 that is thinner can increase its permeability and therefore reduce impedance.

In these examples, the flexible supporting membrane 7050 may be positioned to connect within the inside walls of the plenum chamber 3200 and support the HME 7000 within the functional dead space of the patient interface 3000. The flexible supporting membrane 7050 may be made of a flexible material such as silicone but could also be made from HME material. The flexibility allows for easily manipulating and moving the flexible supporting membrane 7050 holding the HME 7000. Furthermore, the flexible supporting membrane 7050 may be impermeable to humidified air exhaled from the patient's 1000 airways to avoid any loss in humidification thorough the vent 3400. Impermeability of the flexible supporting membrane 7050 may ensure that the exhaled humidified air passes through the HME 7000 for maximised hygroscopic performance.

In another example, a HME 7000 may be positioned in the functional dead space within the plenum chamber 3200 of patient interface 3000 in the form of a nasal mask supported by a supporting membrane 7050.

In one example of the technology, the added humidity above ambient humidity is measured using a Humiflo HME, as shown in FIG. 17, having a diameter of 35 cm with a volume of 10 cm$^3$. The HME is positioned in the functional dead space of a ResMed Quattro FX patient interface. It is noted that leak at the patient interface can result in the increase of average an flow rate through the plenum chamber of the patient interface, ultimately having a negative impact by reducing the humidity within the patient interface due to loses though the system. The added humidity was measured at therapeutic pressures ranging from 4 cm of $H_2O$ to 20 cm of $H_2O$ (flow rates ranging from 20 L/min to 50 L/min). FIG. 17 shows an addition of approximately 5 mg/L to 18 mg/L of added absolute humidity. More specifically, the graph shows an added absolute humidity of 9.5 mg/L to 17.5 mg/L at the same flow rates. The humidity over time at a particular pressure ranges from a minimum humidity occurring during inhalation and a maximum humidity during exhalation. The average humidity was measured across the breath cycle as a comparative metric.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by a RPT device or emanating from a mask or patient interface. Ambient noise may be generated by sources outside the room.

Continuous Positive Airway Pressure (CPAP): CPAP treatment will be taken to mean the application of a supply of air to the entrance to the airways at a pressure that is continuously positive with respect to atmosphere, and approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.8.2 Aspects of the Respiratory Cycle

Apnea: Apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: A hypopnea will be taken to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow (Qpeak): The maximum value of flow during the inspiratory portion of the respiratory flow waveform.

Respiratory flow, airflow, patient airflow, respiratory airflow (Qr): These synonymous terms may be understood to refer to the RPT device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

5.8.3 RPT Device Parameters

Flow rate (orflow): The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. Total flow, Qt, is the flow rate of air leaving the RPT device. Vent flow, Qv, is the flow rate of air leaving a vent to allow washout of exhaled gases. Leak flow, Ql, is the flow rate of unintentional leak from a patient interface system. Respiratory flow, Qr, is the flow rate of air that is received into the patient's respiratory system.

Leak: The word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2$. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

5.8.4 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (ST)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator A mechanical device that provides pressure support to a patient to perform some or all of the work of breathing.

5.8.5 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bonyframework: The bony framework of the nose comprises the nasal bones, the frontal process of the maxillae and the nasal part of the frontal bone.

(nose) Cartilaginousframework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labialfold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.8.6 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, theforamen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.7 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx. The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.8 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.8.9 Aspects of a Patient Interface

Anti-asphyxia valve (AA V): The component or subassembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Mask Frame: Mask frame will be taken to mean a mask structure that bears the load of tension between two or more points of connection with a headgear. A mask frame may be a non-airtight load bearing structure in the mask. However, some forms of mask frame may also be air-tight.

Headgear. Headgear will be taken to mean a form of positioning and stabilizing structure designed for use on a head. The headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has substantially no resistance to bending, but has resistance to being stretched.

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved two-dimensional structure having bending, tensile and compressive stiffness, for example, a portion of a mask that forms a curved structural wall of the mask. Compared to its overall dimensions, it is relatively thin. In some forms, a shell may be faceted. Such walls may be airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, independently, and under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components comprises a matched pair of cylindrical conduits. There is little or no leak flow of air from the swivel in use.

Tie: A tie will be taken to be a structural component designed to resist tension.

Vent: (noun) the structure that allows an intentional flow of air from an interior of the mask, or conduit to ambient air, e.g. to allow washout of exhaled gases.

5.8.10 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:
Readily conforming to finger pressure.
Unable to retain its shape when caused to support its own weight.
Not rigid.
Able to be stretched or bent elastically with little effort.
The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

5.9 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A patient interface for sealed delivery of a flow of air at a continuously positive pressure with respect to ambient air pressure to an entrance to a patient's airways including at least the patient's nares, the patient interface being configured to maintain a therapeutic pressure in a range of about 4 cmH2O to about 30 cmH2O above ambient air pressure in use, throughout the patient's respiratory cycle, while the patient is sleeping, to ameliorate sleep disordered breathing, said patient interface comprising:
   a plenum chamber configured to be pressurised at the therapeutic pressure in use;
   a seal forming structure connected to the plenum chamber and configured to seal with an area around the entrance to the patient's airways including at least the patient's nares, and the seal forming structure being constructed from a soft, flexible, resilient material;
   a positioning and stabilising structure comprising a plurality of straps configured to maintain the seal forming structure in sealing contact with the area surrounding the entrance to the patient's airways while maintaining the therapeutic pressure at the entrance to the patient's airways;
   a connection port configured to connect to an air circuit to receive the flow of air and direct the flow of air into the plenum chamber;
   a heat and moisture exchanger (HME) including an HME material configured to absorb and retain moisture from a first portion of a flow of patient-exhaled gas and release moisture into the flow of air during use;
   a gas washout vent configured to be positioned opposite the patient relative to the HME in use to allow the first portion of the flow of patient-exhaled gas to escape to ambient air after passing through the HME to minimise rebreathing of carbon dioxide by the patient; and
   an auxiliary vent configured to allow a second portion of the flow of patient-exhaled gas to escape to ambient air without passing through the HME to minimise rebreathing of carbon dioxide by the patient.

2. The patient interface of claim 1, wherein the HME includes a rigid frame, the HME material being positioned within the rigid frame.

3. The patient interface of claim 2, wherein the rigid frame further comprises at least one retention member configured to hold the HME material within the rigid frame.

4. The patient interface of claim 3, wherein the at least one retention member is configured to structurally support the rigid frame.

5. The patient interface of claim 3, further comprising a first retention member positioned on a front side of the rigid frame and a second retention member positioned on a rear side of the rigid frame.

6. The patient interface of claim 2, wherein the rigid frame includes at least one engagement member configured to releasably attach the rigid frame to the patient interface.

7. The patient interface of claim 6, wherein the at least one engagement member is configured to releasably attach the rigid frame to the patient interface with a snap-fit.

8. The patient interface of claim 2, wherein the rigid frame further comprises at least one frame aperture oriented to allow the flow of air and/or the first portion of the flow of patient-exhaled gas to reach the HME material.

9. The patient interface of claim 8, wherein the HME material includes a plurality of channels configured to allow the flow of air and the first portion of the flow of patient-exhaled gas to pass through the HME material along a flow path, and
   wherein the at least one frame aperture is aligned with the flow path such that the flow of air and the first portion of the flow of patient-exhaled gas pass through the at least one frame aperture during use.

10. The patient interface of claim 2, wherein the HME material is positioned such that during use:
    the flow of air travels in a first direction from the connection port, through the HME material, and to the patient's airways; and
    the first portion of the flow of patient-exhaled gas travels in a second direction, opposite the first direction, from the patient's airways, through the HME material, and exits to atmosphere through the gas washout vent.

11. The patient interface of claim 10, further comprising a baffle configured to separate the flow of air traveling in the first direction from the first portion of the flow of patient-exhaled gas traveling in the second direction.

12. The patient interface of claim 2, wherein the HME material consists of foam.

13. The patient interface of claim 2, wherein the HME material consists of paper.

14. The patient interface of claim 13, wherein the paper HME material includes corrugations and the paper HME material is rolled into a coil.

15. The patient interface of claim 2, wherein the HME material comprises at least one of foam and paper.

16. The patient interface of claim 1, wherein the HME material comprises a plurality of layers arranged into a predetermined three-dimensional shape.

17. The patient interface of claim 1, wherein the HME material comprises a corrugated structure comprising a plurality of corrugations, the plurality of corrugations forming a plurality of channels to allow the flow of air along a surface of the corrugated structure for moisture exchange.

18. The patient interface of claim 17, wherein the HME is oriented such that the plurality of channels are substantially parallel to a flow path of the flow of air.

19. The patient interface of claim 1, wherein the auxiliary vent is formed on the plenum chamber.

20. The patient interface of claim 1, wherein the HME is positioned inside of the plenum chamber.

21. The patient interface of claim 1, wherein the gas washout vent comprises a plurality of vent holes and the auxiliary vent comprises a plurality of auxiliary vent holes.

22. The patient interface of claim 1, wherein the gas washout vent is positioned in the plenum chamber.

23. The patient interface of claim 1, further comprising a decoupling structure, the gas washout vent being positioned in the decoupling structure.

24. The patient interface of claim 1, wherein the auxiliary vent is configured to be positioned between the HME and the patient in use.

25. The respiratory therapy system of claim 24, wherein the respiratory therapy system does not include a humidifier.

26. A respiratory therapy system to provide respiratory therapy to a patient, the respiratory therapy system comprising:
- a respiratory therapy device including a pressure generator configured to generate the flow of air at the continuously positive pressure with respect to ambient air pressure in the range of about 4 cmH2O to about 30 cmH2O above ambient air pressure in use;
- the patient interface of claim 1; and
- an air circuit configured to direct the flow of air from the respiratory therapy device to the patient interface.

* * * * *